United States Patent [19]

Takematsu et al.

[11] Patent Number: 4,838,924
[45] Date of Patent: Jun. 13, 1989

[54] AROMATIC UREA DERIVATIVES AND THEIR USE AS HERBICIDE

[75] Inventors: Tetsuo Takematsu, Utsunomiya; Daisuke Fukuoka, Iwakuni; Katsuya Takahashi, Ohtake; Isao Hashimoto, Iwakuni, all of Japan

[73] Assignee: Mitsui Petrochemical Industries, Ltd., Tokyo, Japan

[21] Appl. No.: 39,457
[22] PCT Filed: Aug. 4, 1986
[86] PCT No.: PCT/JP86/00398
 § 371 Date: Apr. 1, 1987
 § 102(e) Date: Apr. 1, 1987
[87] PCT Pub. No.: WO87/00840
 PCT Pub. Date: Feb. 12, 1987

[30] Foreign Application Priority Data

Aug. 5, 1985 [JP] Japan .................................. 60-171025
Mar. 25, 1986 [JP] Japan .................................. 61-64757

[51] Int. Cl.⁴ ..................... C07D 307/79; A01N 43/12
[52] U.S. Cl. ............................................ 71/88; 71/94; 549/331; 549/333; 549/334; 549/385; 549/386; 549/399; 549/400; 549/408; 549/445; 549/458; 549/460; 549/462; 549/464; 549/466; 546/15; 546/270; 546/269
[58] Field of Search .......................... 546/15, 269, 270; 549/333, 331, 334, 386, 385, 399, 400, 408, 460, 458, 466, 462, 464, 445; 71/88, 94

[56] References Cited

U.S. PATENT DOCUMENTS 3,707,557 12/1972 Brown ..................................... 71/120
3,773,491 11/1973 Cruickshank ........................... 71/88
4,376,646 3/1983 Rohr et al. .............................. 71/88
4,426,385 1/1984 Cain ...................................... 549/408

FOREIGN PATENT DOCUMENTS 0105735 4/1984 European Pat. Off. .
2016010 9/1979 United Kingdom .

OTHER PUBLICATIONS

Sirrenberg et al., CA 105 : 60616b.
Patent Cooperation Treaty International Search Report.

Primary Examiner—Jane T. Fan
Attorney, Agent, or Firm—Sherman and Shalloway

[57] ABSTRACT

This invention relates to novel compounds of formula [I], a process for their production, and their use as a herbicide.

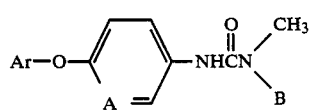

wherein
A represents the bond

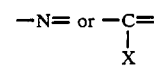

in which X is a hydrogen atom, a chlorine atom, a nitro group or a trifluoromethyl group;
B represents a hydrogen atom, a methyl group or a methoxy group; and
Ar represents one member selected from the group consisting of

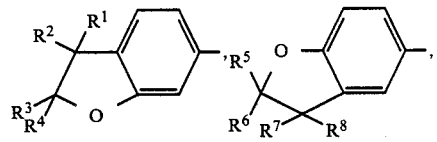

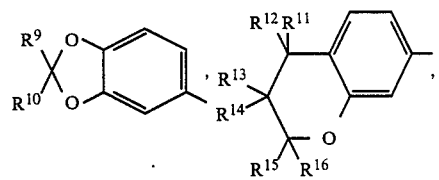

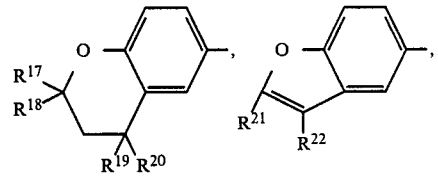

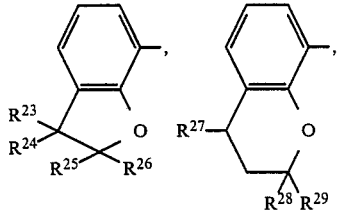

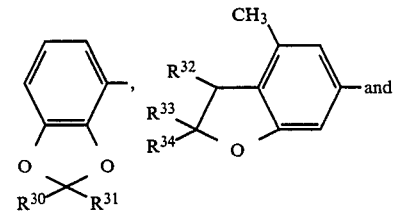

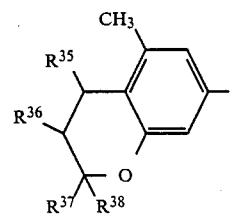

in which $R^1$ to $R^{38}$ are as defined hereinafter.

24 Claims, No Drawings

AROMATIC UREA DERIVATIVES AND THEIR USE AS HERBICIDE

TECHNOLOGICAL FIELD

This invention relates to novel urea derivatives having herbicidal activity and being useful as a herbicide, processes for production thereof and a herbicide comprising such a urea derivative.

BACKGROUND TECHNOLOGY

Wheat, corn, rice and soybean are important crops, and many herbicides have been used to increase the harvest of these crops. Conventional herbicides, however, have not proved to be entirely satisfactory in regard to herbicidal activity or safety on crops, and it has been desired to develop herbicides which kill hazardous weeds in low dosages and do not cause phytotoxicity to crops.

It is an object of this invention to provide herbicidally active urea derivatives which are not described in the prior literature and can meet the aforesaid desire, processes for production thereof, a herbicide comprising such a urea derivative as an active ingredient, and a method of controlling weeds.

DISCLOSURE OF THE INVENTION

The present inventors have made investigations in order to develop a herbicidally active compound which is not likely to cause unnegligible phytotoxicity to useful crops and can control hazardous weeds in low dosages. These investigations have led to the successful synthesis of urea derivatives represented by the following formula [I] not described in the prior literature, and also to the discovery that the compounds of formula [I] are useful for controlling hazardous weeds at reduced dosages, have low phytotoxicity on useful crops, and are very superior compounds in herbicide applications.

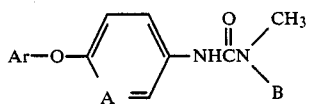

wherein

A represents the bond

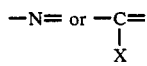

in which X is a hydrogen atom, a chlorine atom, a nitro group or a trifluoromethyl group;

B represents a hydrogen atom, a methyl group or a methoxy group; and

Ar represents one member selected from the group consisting of

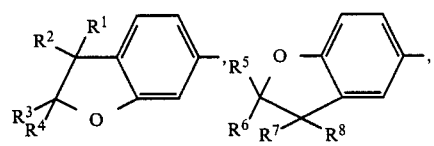

-continued

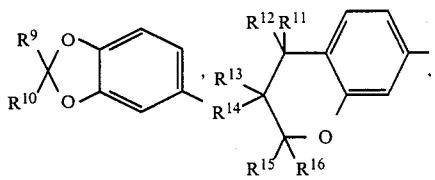

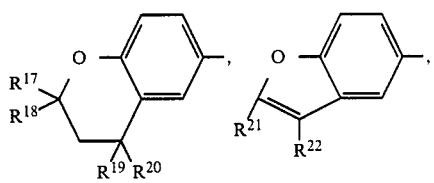

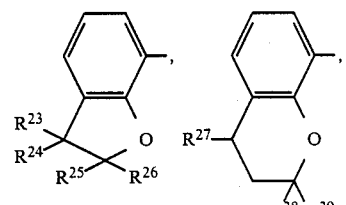

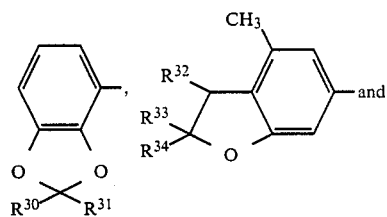

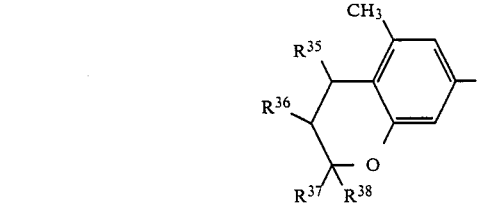

in which $R^1$ to $R^{38}$, independently from each other, represent a hydrogen atom, a lower alkyl group or a lower alkoxy group; $R^{16}$ may further represent a hydroxyl group; a pair of $R^2$ and $R^3$, and a pair of $R^6$ and $R^7$ each, taken together, may represent an alkylene linkage and may form a 5- or 6-membered ring together with the two adjacent carbon atoms to which they are bonded; a pair of $R^9$ and $R^{10}$, taken together, may represent an alkylene linkage and may form a 5- or 6-membered ring together with the carbon atom to which they are bonded; $R^{11}$ and $R^{12}$, taken together, may form an ethylenedioxy linkage $-O-(CH_2)_2-O-$, or $R^{11}$ and $R^{15}$, taken together, may form an alkylene linkage and form a 5- or 6-membered ring together with the carbon atoms to which they are bonded, or $R^{15}$ and $R^{16}$, taken together, may represent an alkylene linkage and form a 5- or 6-membered ring together with one carbon atom to which they are bonded, or $R^{14}$ and $R^{15}$, taken together, may form a dichloromethylene linkage.

When in general formula [I], $R^1$ to $R^{38}$ represent a lower alkyl group or a lower alkoxy group, they usually contain 1 to 4 carbon atoms, preferably 1 to 3 carbon atoms. Specific examples include methyl, ethyl, n-propyl, isopropyl, n-butyl, isobutyl, sec-butyl, tert-butyl, methoxy, ethoxy, n-propoxy, isopropoxy, n-butoxy, isobutoxy and sec-butoxy groups.

When $R^2$ and $R^3$ are bonded to each other to form an alkylene group, the total number of carbon atoms of the alkylene group is usually 3 or 4. Examples of the alkylene group are $-(CH_2)_3-$ and $-(CH_2)_4-$.

When $R^6$ and $R^7$ are bonded to each other to form an alkylene group, the total number of carbon atoms of the alkylene group are usually 3 to 5. Examples include

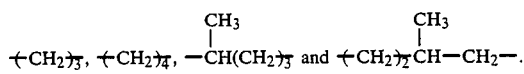

When $R^9$ and $R^{10}$ are bonded to each other to form an alkylene group, the total number of carbon atoms of the alkylene group is usually 4 or 5. Examples include $-(CH_2)_4-$ and $-(CH_2)_5-$.

When $R^{11}$ and $R^{15}$ are bonded to each other to form an alkylene group, the total number of carbon atoms of the alkylene group is usually 2 or 3. Examples include $-(CH_2)_2-$ and $-(CH_2)_3-$.

When $R^{15}$ and $R^{16}$ are bonded to each other to form an alkylene group, the total number of carbon atoms is usually 4 or 5. Examples include $-(CH_2)_4-$ and $-(CH_2)_5-$.

Examples of the Ar group are listed below.

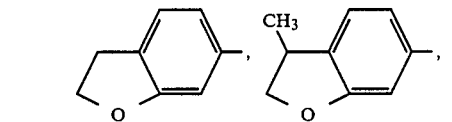

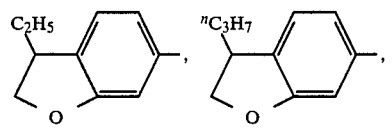

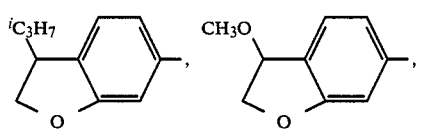

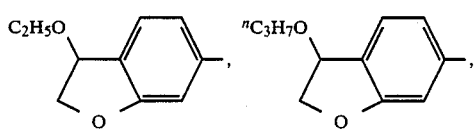

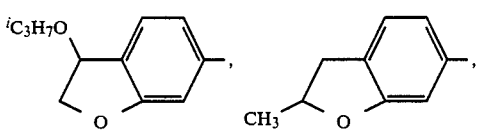

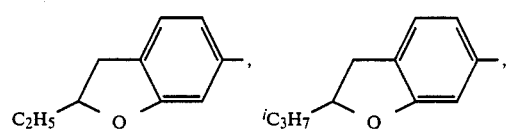

-continued

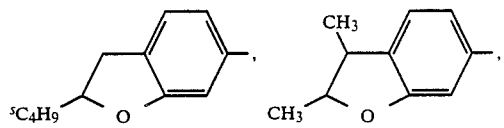

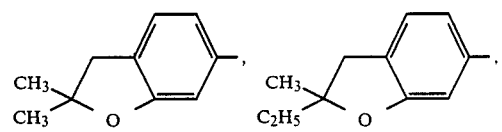

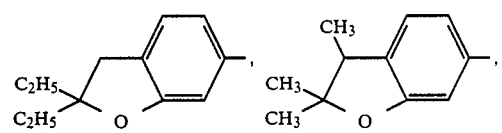

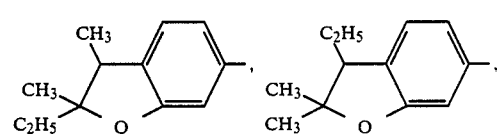

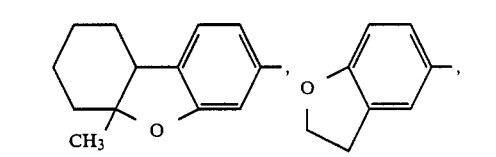

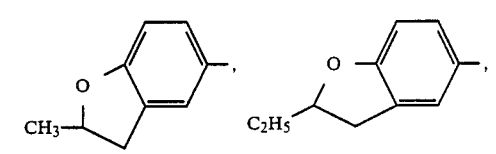

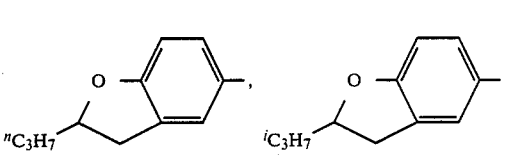

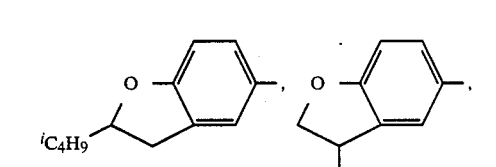

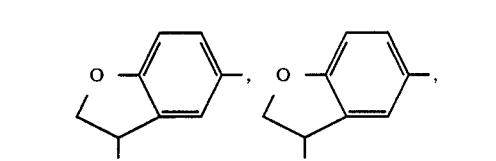

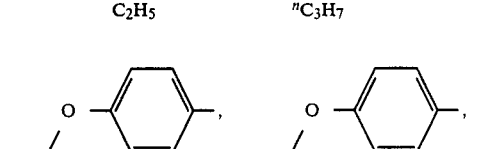

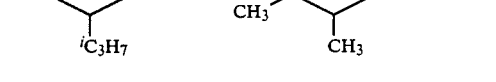

-continued

-continued
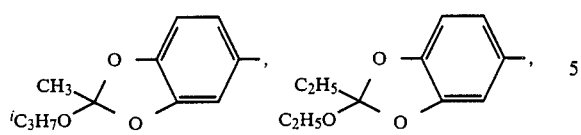
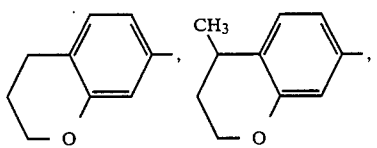
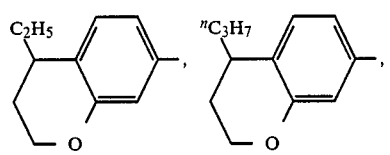
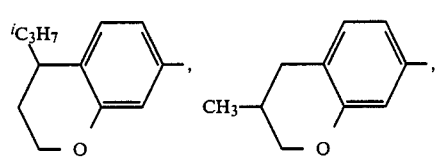
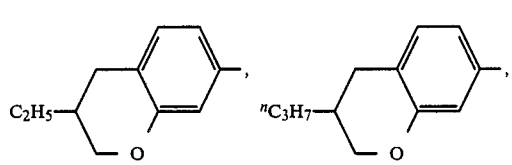
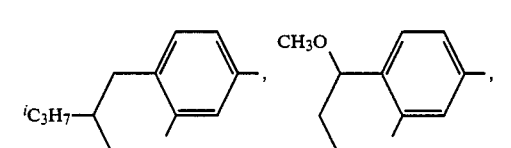
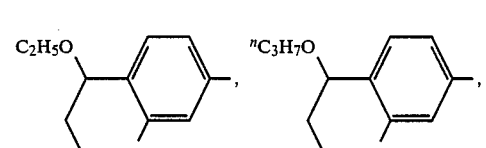
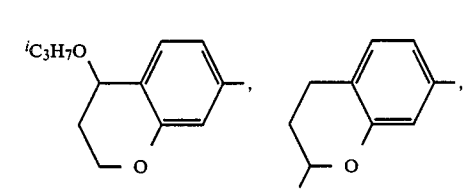
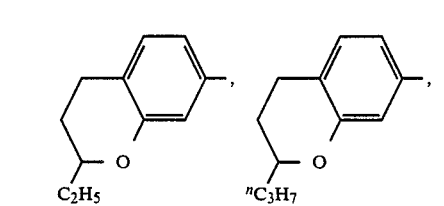
-continued
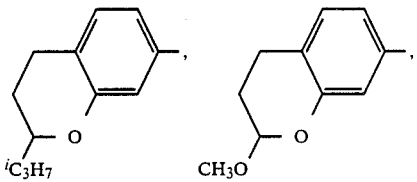
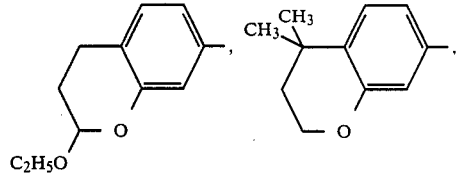
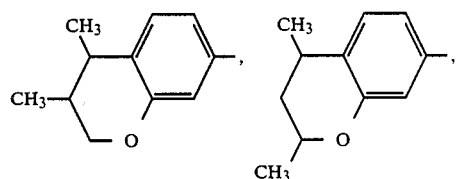
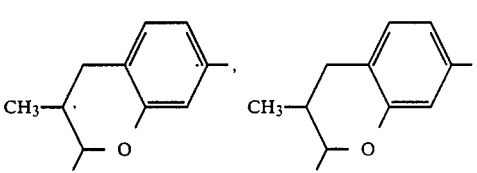
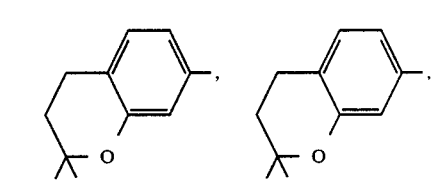
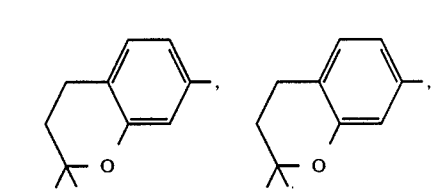
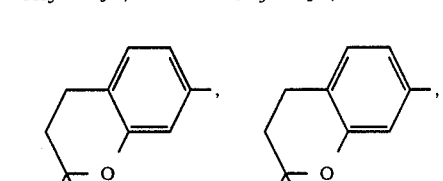
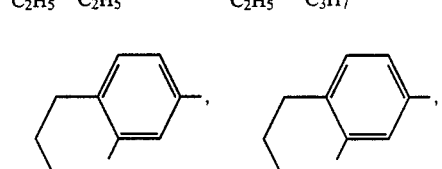

-continued

-continued
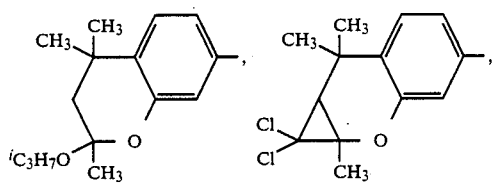
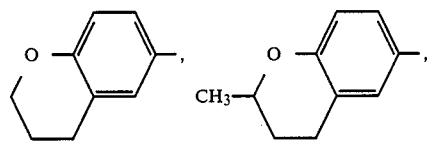
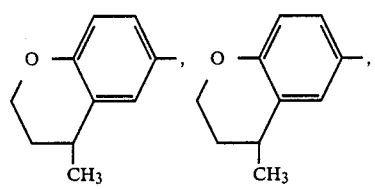
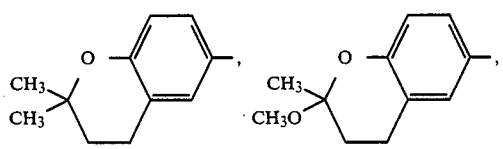
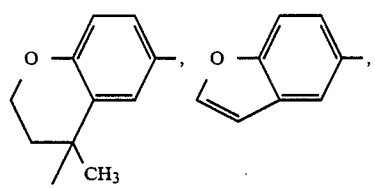
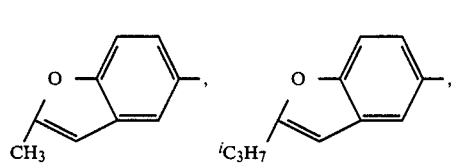
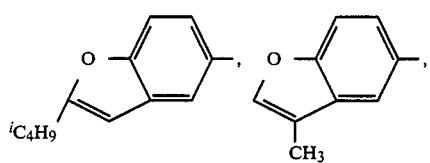
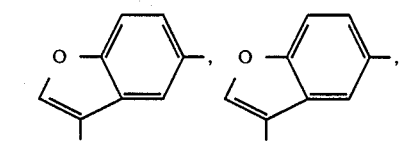
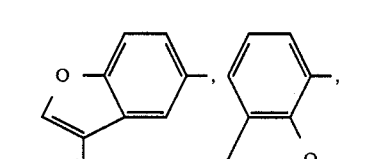
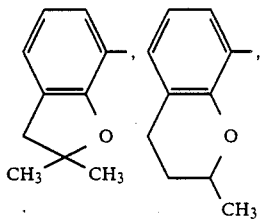
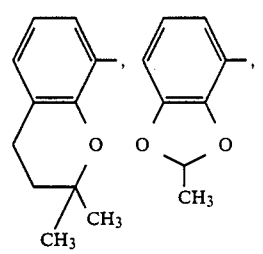
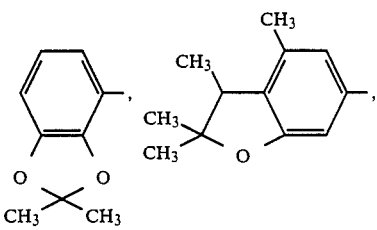
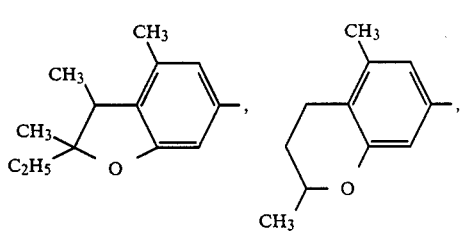
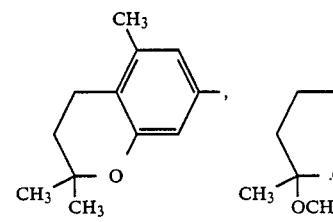
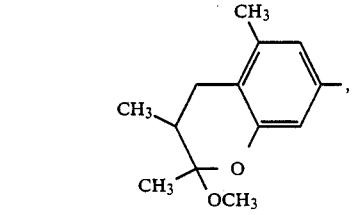
Among these urea derivatives of this invention, preferred specific examples are shown in Tables 1 to 11.

TABLE 1

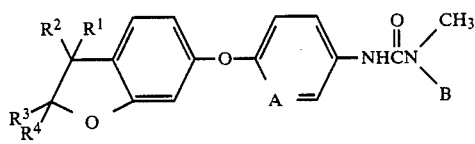

| Compound No. | R¹ | R² | R³ | R⁴ | A | B |
|---|---|---|---|---|---|---|
| 1 | CH$_3$ | H | H | H | pyridine-2,5-diyl (N at position shown) | CH$_3$ |
| 2 | CH$_3$ | H | H | H | pyridine-2,5-diyl | OCH$_3$ |
| 3 | CH$_3$ | H | H | H | 1,4-phenylene | H |
| 4 | CH$_3$ | H | H | H | 1,4-phenylene | CH$_3$ |
| 5 | CH$_3$ | H | H | H | 1,4-phenylene | OCH$_3$ |
| 6 | CH$_3$ | H | CH$_3$ | CH$_3$ | pyridine-2,5-diyl | CH$_3$ |
| 7 | CH$_3$ | H | CH$_3$ | CH$_3$ | pyridine-2,5-diyl | OCH$_3$ |
| 8 | CH$_3$ | H | CH$_3$ | CH$_3$ | 1,4-phenylene | H |
| 9 | CH$_3$ | H | CH$_3$ | CH$_3$ | 1,4-phenylene | CH$_3$ |
| 10 | CH$_3$ | H | CH$_3$ | CH$_3$ | 1,4-phenylene | OCH$_3$ |
| 11 | H | H | H | H | 1,4-phenylene | CH$_3$ |
| 12 | H | H | H | H | 1,4-phenylene | OCH$_3$ |
| 13 | C$_2$H$_5$ | H | H | H | 1,4-phenylene | CH$_3$ |
| 14 | C$_2$H$_5$ | H | H | H | 1,4-phenylene | OCH$_3$ |
| 15 | $^n$C$_3$H$_7$ | H | H | H | 1,4-phenylene | CH$_3$ |
| 16 | $^n$C$_3$H$_7$ | H | H | H | 1,4-phenylene | OCH$_3$ |
| 17 | CH$_3$ | H | CH$_3$ | H | 1,4-phenylene | CH$_3$ |
| 18 | CH$_3$ | H | CH$_3$ | H | 1,4-phenylene | OCH$_3$ |
| 19 | H | H | CH$_3$ | H | 1,4-phenylene | H |
| 20 | H | H | CH$_3$ | H | 1,4-phenylene | CH$_3$ |
| 21 | H | H | CH$_3$ | H | 1,4-phenylene | OCH$_3$ |
| 22 | H | H | C$_2$H$_5$ | H | 1,4-phenylene | H |

TABLE 1-continued

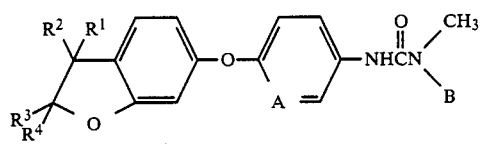

| Compound No. | R¹ | R² | R³ | R⁴ | A | B |
|---|---|---|---|---|---|---|
| 23 | H | H | C₂H₅ | H | (p-phenylene) | CH₃ |
| 24 | H | H | C₂H₅ | H | (p-phenylene) | OCH₃ |
| 25 | H | H | iC₃H₇ | H | (p-phenylene) | H |
| 26 | H | H | iC₃H₇ | H | (p-phenylene) | CH₃ |
| 27 | H | H | iC₃H₇ | H | (p-phenylene) | OCH₃ |
| 28 | H | H | sC₄H₉ | H | (p-phenylene) | H |
| 29 | H | H | sC₄H₉ | H | (p-phenylene) | CH₃ |
| 30 | H | H | sC₄H₉ | H | (p-phenylene) | OCH₃ |
| 31 | H | H | CH₃ | CH₃ | (p-phenylene) | H |
| 32 | H | H | CH₃ | CH₃ | (p-phenylene) | CH₃ |
| 33 | H | H | CH₃ | CH₃ | (p-phenylene) | OCH₃ |

TABLE 1-continued

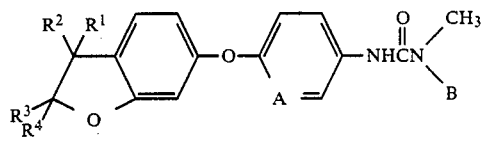

| Compound No. | R¹ | R² | R³ | R⁴ | A | B |
|---|---|---|---|---|---|---|
| 34 | H | H | CH₃ | C₂H₅ | (p-phenylene) | H |
| 35 | H | H | CH₃ | C₂H₅ | (p-phenylene) | CH₃ |
| 36 | H | H | CH₃ | C₂H₅ | (p-phenylene) | OCH₃ |
| 37 | H | H | C₂H₅ | C₂H₅ | (p-phenylene) | H |
| 38 | H | H | C₂H₅ | C₂H₅ | (p-phenylene) | CH₃ |
| 39 | H | H | C₂H₅ | C₂H₅ | (p-phenylene) | OCH₃ |
| 40 | CH₃ | H | CH₃ | C₂H₅ | (pyridine-2,5-diyl) | H |
| 41 | CH₃ | H | CH₃ | C₂H₅ | (pyridine-2,5-diyl) | CH₃ |
| 42 | CH₃ | H | CH₃ | C₂H₅ | (pyridine-2,5-diyl) | OCH₃ |
| 43 | CH₃ | H | CH₃ | C₂H₅ | (p-phenylene) | CH₃ |
| 44 | CH₃ | H | CH₃ | C₂H₅ | (p-phenylene) | OCH₃ |

TABLE 1-continued

Structure: R²R¹-substituted benzofuran-O-A-NHC(O)N(CH₃)-B-phenyl

| Compound No. | R¹ | R² | R³ | R⁴ | A | B-phenyl substituent |
|---|---|---|---|---|---|---|
| 45 | CH₃ | H | CH₃ | C₂H₅ | (phenyl) | 3-Cl, 4-H |
| 46 | CH₃ | H | CH₃ | C₂H₅ | (phenyl) | 3-Cl, 4-CH₃ |
| 47 | CH₃ | H | CH₃ | C₂H₅ | (phenyl) | 3-Cl, 4-OCH₃ |
| 48 | CH₃ | H | CH₃ | C₂H₅ | (phenyl) | 3-NO₂, 4-H |
| 49 | CH₃ | H | CH₃ | C₂H₅ | (phenyl) | 3-NO₂, 4-CH₃ |
| 50 | CH₃ | H | CH₃ | C₂H₅ | (phenyl) | 3-NO₂, 4-OCH₃ |
| 51 | CH₃ | H | CH₃ | C₂H₅ | (phenyl) | 3-CF₃, 4-H |
| 52 | CH₃ | H | CH₃ | C₂H₅ | (phenyl) | 3-CF₃, 4-CH₃ |
| 53 | CH₃ | H | CH₃ | C₂H₅ | (phenyl) | 3-CF₃, 4-OCH₃ |
| 54 | C₂H₅ | H | CH₃ | CH₃ | (phenyl) | 4-H |
| 55 | C₂H₅ | H | CH₃ | CH₃ | (phenyl) | 4-CH₃ |
| 56 | C₂H₅ | H | CH₃ | CH₃ | (phenyl) | 4-OCH₃ |
| 57 | H | —(CH₂)₄— | | CH₃ | (phenyl) | 4-CH₃ |
| 58 | H | —(CH₂)₄— | | CH₃ | (phenyl) | 4-OCH₃ |

TABLE 2
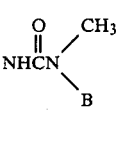
| Compound No. | R⁵ | R⁶ | R⁷ | R⁸ | A | B |
|---|---|---|---|---|---|---|
| 59 | CH₃ | H | H | H | pyridine | CH₃ |
| 60 | CH₃ | H | H | H | pyridine | OCH₃ |
| 61 | CH₃ | H | H | H | phenyl | CH₃ |
| 62 | CH₃ | H | H | H | phenyl | OCH₃ |
| 63 | H | H | CH₃ | H | phenyl | CH₃ |
| 64 | H | H | CH₃ | H | phenyl | OCH₃ |
| 65 | H | H | C₂H₅ | H | phenyl | CH₃ |
| 66 | H | H | C₂H₅ | H | phenyl | OCH₃ |
| 67 | H | H | ⁿC₃H₇ | H | phenyl | CH₃ |
| 68 | H | H | ⁿC₃H₇ | H | phenyl | OCH₃ |
| 69 | H | H | ⁱC₃H₇ | H | phenyl | H |

TABLE 2-continued

Structure:
$$R^5R^6C(R^7R^8)\text{-}(phenyl\text{-}O)\text{-}(phenyl\text{-}O)\text{-}A\text{-}NHC(O)N(CH_3)(B)$$

with ortho-O-alkyl phenyl—O—phenyl—O—A—NHC(=O)N(CH₃)B

| Compound No. | $R^5$ | $R^6$ | $R^7$ | $R^8$ | A | B |
|---|---|---|---|---|---|---|
| 70 | H | H | $^iC_3H_7$ | H | phenylene | $CH_3$ |
| 71 | H | H | $^iC_3H_7$ | H | phenylene | $OCH_3$ |
| 72 | $^iC_4H_9$ | H | H | H | phenylene | H |
| 73 | $^iC_4H_9$ | H | H | H | phenylene | $CH_3$ |
| 74 | $^iC_4H_9$ | H | H | H | phenylene | $OCH_3$ |
| 75 | $OCH_3$ | H | $C_2H_5$ | H | phenylene | H |
| 76 | $OCH_3$ | H | $C_2H_5$ | H | phenylene | $CH_3$ |
| 77 | $OCH_3$ | H | $C_2H_5$ | H | phenylene | $OCH_3$ |
| 78 | $CH_3$ | H | $CH_3$ | H | pyridylene (N) | $CH_3$ |
| 79 | $CH_3$ | H | $CH_3$ | H | pyridylene (N) | $OCH_3$ |
| 80 | $CH_3$ | H | $CH_3$ | H | phenylene | H |

TABLE 2-continued

| Compound No. | R⁵ | R⁶ | R⁷ | R⁸ | A | B |
|---|---|---|---|---|---|---|
| 81 | CH₃ | H | CH₃ | H | phenyl | CH₃ |
| 82 | CH₃ | H | CH₃ | H | phenyl | OCH₃ |
| 83 | CH₃ | CH₃ | H | H | pyridyl (N) | CH₃ |
| 84 | CH₃ | CH₃ | H | H | pyridyl (N) | OCH₃ |
| 85 | CH₃ | CH₃ | H | H | phenyl | CH₃ |
| 86 | CH₃ | CH₃ | H | H | phenyl | OCH₃ |
| 87 | H | H | CH₃ | CH₃ | phenyl | H |
| 88 | H | H | CH₃ | CH₃ | phenyl | CH₃ |
| 89 | H | H | CH₃ | CH₃ | phenyl | OCH₃ |
| 90 | OC₂H₅ | H | CH₃ | H | phenyl | CH₃ |
| 91 | OC₂H₅ | H | CH₃ | H | phenyl | OCH₃ |

TABLE 2-continued

Structure:

R⁵R⁶R⁷R⁸-C- attached to phenyl-O-phenyl-O-(A)-NHC(O)N(CH₃)(B)

| Compound No. | R⁵ | R⁶ | R⁷ | R⁸ | A | B |
|---|---|---|---|---|---|---|
| 92 | OCH₃ | H | CH₃ | CH₃ | pyridine | CH₃ |
| 93 | OCH₃ | H | CH₃ | CH₃ | pyridine | OCH₃ |
| 94 | OCH₃ | H | CH₃ | CH₃ | phenyl | H |
| 95 | OCH₃ | H | CH₃ | CH₃ | phenyl | CH₃ |
| 96 | OCH₃ | H | CH₃ | CH₃ | phenyl | OCH₃ |
| 97 | OCH₃ | H | CH₃ | CH₃ | 3-Cl-phenyl | CH₃ |
| 98 | OCH₃ | H | CH₃ | CH₃ | 3-Cl-phenyl | OCH₃ |
| 99 | OCH₃ | H | CH₃ | C₂H₅ | phenyl | H |
| 100 | OCH₃ | H | CH₃ | C₂H₅ | phenyl | CH₃ |
| 101 | OCH₃ | H | CH₃ | C₂H₅ | phenyl | OCH₃ |
| 102 | OCH₃ | H | C₂H₅ | C₂H₅ | phenyl | H |

TABLE 2-continued

[Structure: phenyl ring with O-CR5R6-CR7R8 substituent, linked via O to ring A, with NHC(=O)N(CH3)(B) group]

| Compound No. | R⁵ | R⁶ | R⁷ | R⁸ | A | B |
|---|---|---|---|---|---|---|
| 103 | OCH₃ | H | C₂H₅ | C₂H₅ | para-phenylene | CH₃ |
| 104 | OCH₃ | H | C₂H₅ | C₂H₅ | para-phenylene | OCH₃ |
| 105 | OCH₃ | H | iC₃H₇ | H | para-phenylene | CH₃ |
| 106 | OCH₃ | H | iC₃H₇ | H | para-phenylene | OCH₃ |
| 107 | OC₂H₅ | H | C₂H₅ | H | para-phenylene | CH₃ |
| 108 | OC₂H₅ | H | C₂H₅ | H | para-phenylene | OCH₃ |
| 109 | OC₂H₅ | H | iC₃H₇ | H | para-phenylene | H |
| 110 | OC₂H₅ | H | iC₃H₇ | H | para-phenylene | CH₃ |
| 111 | OC₂H₅ | H | iC₃H₇ | H | para-phenylene | OCH₃ |
| 112 | OC₂H₅ | H | CH₃ | CH₃ | para-phenylene | CH₃ |
| 113 | OC₂H₅ | H | CH₃ | CH₃ | para-phenylene | OCH₃ |

TABLE 2-continued

Structure:

$$R^5R^6R^7R^8\text{-substituted} \cdot \text{O-phenyl-O-A-NHC(=O)N(CH}_3\text{)B}$$

| Compound No. | R⁵ | R⁶ | R⁷ | R⁸ | A | B |
|---|---|---|---|---|---|---|
| 114 | OC₃H₇i | H | CH₃ | CH₃ | —⟨phenyl⟩— | CH₃ |
| 115 | OC₃H₇i | H | CH₃ | CH₃ | —⟨phenyl⟩— | OCH₃ |
| 116 | H | —(CH₂)₄— | | H | —⟨phenyl⟩— | H |
| 117 | H | —(CH₂)₄— | | H | —⟨phenyl⟩— | CH₃ |
| 118 | H | —(CH₂)₄— | | H | —⟨phenyl⟩— | OCH₃ |
| 119 | H | —CH(CH₃)—(CH₂)₃— | | H | —⟨phenyl⟩— | H |
| 120 | H | —CH(CH₃)—(CH₂)₃— | | H | —⟨phenyl⟩— | CH₃ |
| 121 | H | —CH(CH₃)—(CH₂)₃— | | H | —⟨phenyl⟩— | OCH₃ |
| 122 | H | —(CH₂)₂—CH(CH₃)—CH₂— | | H | —⟨phenyl⟩— | H |
| 123 | H | —(CH₂)₂—CH(CH₃)—CH₂— | | H | —⟨phenyl⟩— | CH₃ |
| 124 | H | —(CH₂)₂—CH(CH₃)—CH₂— | | H | —⟨phenyl⟩— | OCH₃ |

TABLE 3

| Compound No. | R⁹ | R¹⁰ | A | B |
|---|---|---|---|---|
| 125 | H | H | phenyl | H |
| 126 | H | H | phenyl | CH₃ |
| 127 | H | H | phenyl | OCH₃ |
| 128 | C₂H₅ | CH₃ | phenyl | H |
| 129 | C₂H₅ | CH₃ | phenyl | CH₃ |
| 130 | C₂H₅ | CH₃ | phenyl | OCH₃ |
| 131 | CH₃ | CH₃ | pyridyl | CH₃ |
| 132 | CH₃ | CH₃ | pyridyl | OCH₃ |
| 133 | CH₃ | CH₃ | phenyl | CH₃ |
| 134 | CH₃ | CH₃ | phenyl | OCH₃ |
| 135 | OCH₃ | CH₃ | phenyl | H |
| 136 | OCH₃ | CH₃ | phenyl | CH₃ |
| 137 | OCH₃ | CH₃ | phenyl | OCH₃ |
| 138 | OC₂H₅ | CH₃ | phenyl | CH₃ |
| 139 | OC₂H₅ | CH₃ | phenyl | OCH₃ |
| 140 | OC₂H₅ | C₂H₅ | phenyl | CH₃ |
| 141 | OC₂H₅ | C₂H₅ | phenyl | OCH₃ |
| 142 | OCH₃ | H | phenyl | CH₃ |
| 143 | OCH₃ | H | phenyl | OCH₃ |
| 144 | OC₂H₅ | H | phenyl | CH₃ |
| 145 | OC₂H₅ | H | phenyl | OCH₃ |
| 146 | CH₃ | iC₃H₇ | phenyl | H |

TABLE 3-continued
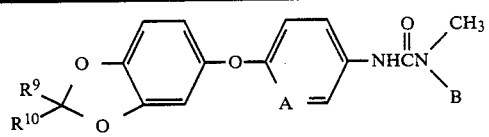
| Compound No. | R⁹ | R¹⁰ | A | B |
|---|---|---|---|---|
| 147 | CH₃ | ⁱC₃H₇ | (phenyl) | CH₃ |
| 148 | CH₃ | ⁱC₃H₇ | (phenyl) | OCH₃ |
| 149 | C₂H₅ | C₂H₅ | (phenyl) | H |
| 150 | C₂H₅ | C₂H₅ | (phenyl) | CH₃ |
| 151 | C₂H₅ | C₂H₅ | (phenyl) | OCH₃ |
| 152 | —(CH₂)₄— | | (phenyl) | H |
| 153 | —(CH₂)₄— | | (phenyl) | CH₃ |
| 154 | —(CH₂)₄— | | (phenyl) | OCH₃ |
TABLE 4
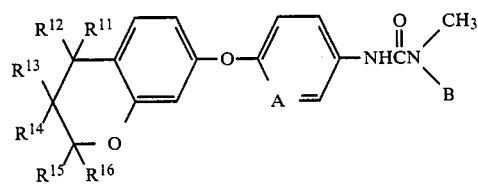
| Compound No. | R¹¹ | R¹² | R¹³ | R¹⁴ | R¹⁵ | R¹⁶ | A | B |
|---|---|---|---|---|---|---|---|---|
| 155 | H | H | H | H | H | H | (pyridyl) | CH₃ |
| 156 | H | H | H | H | H | H | (phenyl) | OCH₃ |
| 157 | CH₃ | H | H | H | H | H | (pyridyl) | CH₃ |
| 158 | CH₃ | H | H | H | H | H | (pyridyl) | OCH₃ |

TABLE 4-continued
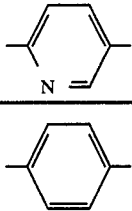
| Compound No. | R11 | R12 | R13 | R14 | R15 | R16 | A | B |
|---|---|---|---|---|---|---|---|---|
| 159 | CH$_3$ | H | H | H | H | H | (phenyl) | CH$_3$ |
| 160 | CH$_3$ | H | H | H | H | H | (phenyl) | OCH$_3$ |
| 161 | H | H | H | H | CH$_3$ | H | (pyridyl) | CH$_3$ |
| 162 | H | H | H | H | CH$_3$ | H | (pyridyl) | OCH$_3$ |
| 163 | H | H | H | H | CH$_3$ | H | (phenyl) | H |
| 164 | H | H | H | H | CH$_3$ | H | (phenyl) | CH$_3$ |
| 165 | H | H | H | H | CH$_3$ | H | (phenyl) | OCH$_3$ |
| 166 | CH$_3$ | CH$_3$ | H | H | H | H | (phenyl) | CH$_3$ |
| 167 | CH$_3$ | CH$_3$ | H | H | H | H | (phenyl) | OCH$_3$ |
| 168 | H | H | H | H | CH$_3$ | CH$_3$ | (pyridyl) | H |
| 169 | H | H | H | H | CH$_3$ | CH$_3$ | (pyridyl) | CH$_3$ |

TABLE 4-continued
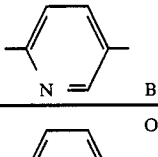
| Compound No. | R11 | R12 | R13 | R14 | R15 | R16 | A | B |
|---|---|---|---|---|---|---|---|---|
| 170 | H | H | H | H | CH3 | CH3 | 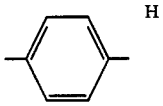 | OCH3 |
| 171 | H | H | H | H | CH3 | CH3 | 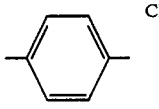 | H |
| 172 | H | H | H | H | CH3 | CH3 | 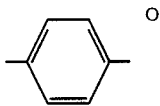 | CH3 |
| 173 | H | H | H | H | CH3 | CH3 | 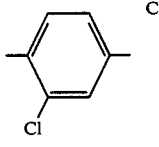 | OCH3 |
| 174 | H | H | H | H | CH3 | CH3 | 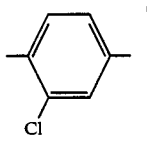 | CH3 |
| 175 | H | H | H | H | CH3 | CH3 | 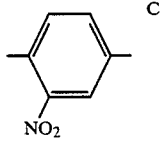 | OCH3 |
| 176 | H | H | H | H | CH3 | CH3 | 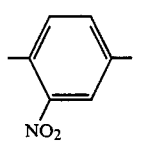 | CH3 |
| 177 | H | H | H | H | CH3 | CH3 | 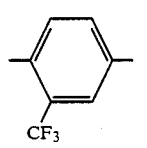 | OCH3 |
| 178 | H | H | H | H | CH3 | CH3 |  | CH3 |

TABLE 4-continued

[Structure: R12,R11 on carbon with R13,R14,R15,R16 chain with O, attached to phenyl-O-pyridyl(A)-NHC(O)N(CH3)(B)]

| Compound No. | R11 | R12 | R13 | R14 | R15 | R16 | A | B |
|---|---|---|---|---|---|---|---|---|
| 179 | H | H | H | H | CH₃ | CH₃ | pyridyl (N) | OCH₃ |
| | | | | | | | phenyl-CF₃ | |
| 180 | CH₃ | CH₃ | H | H | CH₃ | H | pyridyl (N) | CH₃ |
| 181 | CH₃ | CH₃ | H | H | CH₃ | H | pyridyl (N) | OCH₃ |
| 182 | CH₃ | CH₃ | H | H | CH₃ | H | phenyl | CH₃ |
| 183 | CH₃ | CH₃ | H | H | CH₃ | H | phenyl | OCH₃ |
| 184 | CH₃ | H | H | H | CH₃ | CH₃ | pyridyl (N) | OCH₃ |
| 185 | CH₃ | H | H | H | CH₃ | CH₃ | phenyl | CH₃ |
| 186 | CH₃ | H | H | H | CH₃ | CH₃ | phenyl | OCH₃ |
| 187 | OCH₃ | H | H | H | CH₃ | CH₃ | phenyl | CH₃ |
| 188 | OCH₃ | H | H | H | CH₃ | CH₃ | phenyl | OCH₃ |

TABLE 4-continued

| Compound No. | R11 | R12 | R13 | R14 | R15 | R16 | A | B |
|---|---|---|---|---|---|---|---|---|
| 189 | CH3 | CH3 | H | H | CH3 | OCH3 | pyridine | H |
| 190 | CH3 | CH3 | H | H | CH3 | OCH3 | pyridine | CH3 |
| 191 | CH3 | CH3 | H | H | CH3 | OCH3 | pyridine | OCH3 |
| 192 | CH3 | CH3 | H | H | CH3 | OCH3 | phenyl | H |
| 193 | CH3 | CH3 | H | H | CH3 | OCH3 | phenyl | CH3 |
| 194 | CH3 | CH3 | H | H | CH3 | OCH3 | phenyl | OCH3 |
| 195 | CH3 | CH3 | H | H | CH3 | OCH3 | 2-Cl-phenyl | H |
| 196 | CH3 | CH3 | H | H | CH3 | OCH3 | 2-Cl-phenyl | CH3 |
| 197 | CH3 | CH3 | H | H | CH3 | OCH3 | 2-Cl-phenyl | OCH3 |
| 198 | CH3 | CH3 | H | H | CH3 | OCH3 | 2-NO2-phenyl | H |

TABLE 4-continued

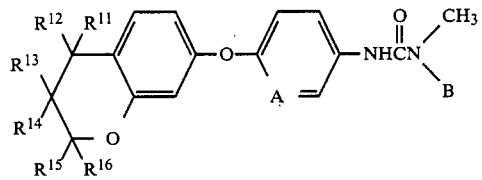

| Compound No. | $R^{11}$ | $R^{12}$ | $R^{13}$ | $R^{14}$ | $R^{15}$ | $R^{16}$ | A | B |
|---|---|---|---|---|---|---|---|---|
| 199 | $CH_3$ | $CH_3$ | H | H | $CH_3$ | $OCH_3$ | 2-NO$_2$-phenyl | $CH_3$ |
| 200 | $CH_3$ | $CH_3$ | H | H | $CH_3$ | $OCH_3$ | 2-NO$_2$-phenyl | $OCH_3$ |
| 201 | $CH_3$ | $CH_3$ | H | H | $CH_3$ | $OCH_3$ | 2-CF$_3$-phenyl | H |
| 202 | $CH_3$ | $CH_3$ | H | H | $CH_3$ | $OCH_3$ | 2-CF$_3$-phenyl | $CH_3$ |
| 203 | $CH_3$ | $CH_3$ | H | H | $CH_3$ | $OCH_3$ | 2-CF$_3$-phenyl | $OCH_3$ |
| 204 | $CH_3$ | $CH_3$ | H | H | $CH_3$ | $OC_2H_5$ | phenyl | $CH_3$ |
| 205 | $CH_3$ | $CH_3$ | H | H | $CH_3$ | $OC_2H_5$ | phenyl | $OCH_3$ |
| 206 | $CH_3$ | $CH_3$ | H | H | $CH_3$ | $OC_3H_7-n$ | phenyl | $CH_3$ |
| 207 | $CH_3$ | $CH_3$ | H | H | $CH_3$ | $OC_3H_7-n$ | phenyl | $OCH_3$ |

TABLE 4-continued

[Structure: R12, R11 on carbon attached to benzene ring with R13, R14, R15, R16, O forming ring; benzene-O-A(pyridine)-NHC(=O)N(CH3)-B]

| Compound No. | R¹¹ | R¹² | R¹³ | R¹⁴ | R¹⁵ | R¹⁶ | A | B |
|---|---|---|---|---|---|---|---|---|
| 208 | CH₃ | CH₃ | H | H | CH₃ | OC₃H₇—i | pyridine | H |
| 209 | CH₃ | CH₃ | H | H | CH₃ | OC₃H₇—i | phenyl | CH₃ |
| 210 | CH₃ | CH₃ | H | H | CH₃ | OC₃H₇—i | phenyl | OCH₃ |
| 211 | OCH₃ | H | H | H | H | H | phenyl | CH₃ |
| 212 | OCH₃ | H | H | H | H | H | phenyl | OCH₃ |
| 213 | H | H | H | H | C₂H₅ | H | phenyl | CH₃ |
| 214 | H | H | H | H | C₂H₅ | H | phenyl | OCH₃ |
| 215 | H | H | H | H | ⁱC₃H₇ | H | phenyl | H |
| 216 | H | H | H | H | ⁱC₃H₇ | H | phenyl | CH₃ |
| 217 | H | H | H | H | ⁱC₃H₇ | H | phenyl | OCH₃ |
| 218 | H | H | H | H | OCH₃ | H | phenyl | H |

TABLE 4-continued
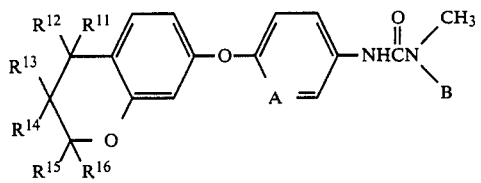
| Compound No. | $R^{11}$ | $R^{12}$ | $R^{13}$ | $R^{14}$ | $R^{15}$ | $R^{16}$ | A | B |
|---|---|---|---|---|---|---|---|---|
| 219 | H | H | H | H | OCH$_3$ | H | | CH$_3$ |
| 220 | H | H | H | H | OCH$_3$ | H | | OCH$_3$ |
| 221 | H | H | H | H | OC$_2$H$_5$ | H | | CH$_3$ |
| 222 | H | H | H | H | OC$_2$H$_5$ | H | | OCH$_3$ |
| 223 | C$_2$H$_5$ | H | H | H | H | H | | H |
| 224 | C$_2$H$_5$ | H | H | H | H | H | | CH$_3$ |
| 225 | C$_2$H$_5$ | H | H | H | H | H | | OCH$_3$ |
| 226 | CH$_3$ | H | CH$_3$ | H | H | H | | H |
| 227 | CH$_3$ | H | CH$_3$ | H | H | H | | CH$_3$ |
| 228 | CH$_3$ | H | CH$_3$ | H | H | H | | OCH$_3$ |
| 229 | CH$_3$ | H | H | H | CH$_3$ | H | | H |

TABLE 4-continued

| Compound No. | R11 | R12 | R13 | R14 | R15 | R16 | A | B |
|---|---|---|---|---|---|---|---|---|
| 230 | CH3 | H | H | H | CH3 | H | pyridine | CH3 |
| 231 | CH3 | H | H | H | CH3 | H | pyridine | OCH3 |
| 232 | CH3 | H | H | H | OCH3 | H | pyridine | CH3 |
| 233 | CH3 | H | H | H | OCH3 | H | pyridine | OCH3 |
| 234 | CH3 | H | H | H | OC2H5 | H | pyridine | CH3 |
| 235 | CH3 | H | H | H | OC2H5 | H | pyridine | OCH3 |
| 236 | OCH3 | H | H | H | CH3 | H | pyridine | CH3 |
| 237 | OCH3 | H | H | H | CH3 | H | pyridine | OCH3 |
| 238 | OCH3 | H | H | H | C2H5 | H | pyridine | OCH3 |
| 239 | H | H | CH3 | H | CH3 | H | pyridine | CH3 |
| 240 | H | H | CH3 | H | CH3 | H | pyridine | OCH3 |

TABLE 4-continued

Structure:
R12, R11 on carbon; R13 on carbon; R14 on carbon; R15, R16 on carbon attached to O; aryl-O-A-NHC(=O)N(CH3)(B), where A is a pyridine ring (N top-left, connection at 2 and 5 positions)

| Compound No. | $R^{11}$ | $R^{12}$ | $R^{13}$ | $R^{14}$ | $R^{15}$ | $R^{16}$ | A | B |
|---|---|---|---|---|---|---|---|---|
| 241 | H | H | CH$_3$ | H | C$_2$H$_5$ | H | phenylene | CH$_3$ |
| 242 | H | H | CH$_3$ | H | C$_2$H$_5$ | H | phenylene | OCH$_3$ |
| 243 | H | H | H | H | CH$_3$ | C$_2$H$_5$ | phenylene | CH$_3$ |
| 244 | H | H | H | H | CH$_3$ | C$_2$H$_5$ | phenylene | OCH$_3$ |
| 245 | H | H | H | H | CH$_3$ | $^n$C$_3$H$_7$ | phenylene | CH$_3$ |
| 246 | H | H | H | H | CH$_3$ | $^n$C$_3$H$_7$ | phenylene | OCH$_3$ |
| 247 | H | H | H | H | CH$_3$ | $^i$C$_3$H$_7$ | phenylene | CH$_3$ |
| 248 | H | H | H | H | CH$_3$ | $^i$C$_3$H$_7$ | phenylene | OCH$_3$ |
| 249 | H | H | H | H | C$_2$H$_5$ | C$_2$H$_5$ | phenylene | CH$_3$ |
| 250 | H | H | H | H | C$_2$H$_5$ | C$_2$H$_5$ | phenylene | OCH$_3$ |
| 251 | H | H | H | H | C$_2$H$_5$ | $^n$C$_3$H$_7$ | phenylene | CH$_3$ |

TABLE 4-continued

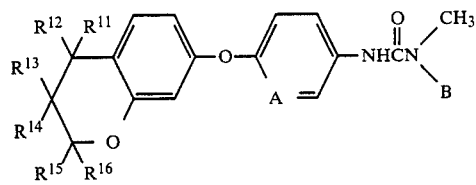

| Compound No. | R¹¹ | R¹² | R¹³ | R¹⁴ | R¹⁵ | R¹⁶ | A | B |
|---|---|---|---|---|---|---|---|---|
| 252 | H | H | H | H | C₂H₅ | ⁿC₃H₇ | para-phenylene | OCH₃ |
| 253 | H | H | H | H | —(CH₂)₅— | | para-phenylene | H |
| 254 | H | H | H | H | —(CH₂)₅— | | para-phenylene | CH₃ |
| 255 | H | H | H | H | —(CH₂)₅— | | para-phenylene | OCH₃ |
| 256 | H | H | H | H | CH₃ | OCH₃ | para-phenylene | H |
| 257 | H | H | H | H | CH₃ | OCH₃ | para-phenylene | CH₃ |
| 258 | H | H | H | H | CH₃ | OCH₃ | para-phenylene | OCH₃ |
| 259 | H | H | H | H | CH₃ | OC₂H₃ | para-phenylene | CH₃ |
| 260 | H | H | H | H | CH₃ | OC₂H₅ | para-phenylene | OCH₃ |
| 261 | H | H | H | H | CH₃ | OC₃H₇—i | para-phenylene | CH₃ |
| 262 | H | H | H | H | CH₃ | OC₃H₇—i | para-phenylene | OCH₃ |

TABLE 4-continued

Structure: aryl with R11, R12, R13, R14, R15, R16 substituents on chromane-like system connected via O to ring A, then NHC(O)N(CH3)(B)

| Compound No. | R11 | R12 | R13 | R14 | R15 | R16 | A | B |
|---|---|---|---|---|---|---|---|---|
| 263 | H | H | H | H | C₂H₅ | OCH₃ | pyridyl | H |
| 264 | H | H | H | H | C₂H₅ | OCH₃ | phenyl | CH₃ |
| 265 | H | H | H | H | C₂H₅ | OCH₃ | phenyl | OCH₃ |
| 266 | CH₃ | H | H | H | CH₃ | OCH₃ | phenyl | H |
| 267 | CH₃ | H | H | H | CH₃ | OCH₃ | phenyl | CH₃ |
| 268 | CH₃ | H | H | H | CH₃ | OCH₃ | phenyl | OCH₃ |
| 269 | CH₃ | H | H | H | C₂H₅ | OCH₃ | phenyl | H |
| 270 | CH₃ | H | H | H | C₂H₅ | OCH₃ | phenyl | CH₃ |
| 271 | CH₃ | H | H | H | C₂H₅ | OCH₃ | pyridyl | OCH₃ |
| 272 | OCH₃ | H | CH₃ | H | CH₃ | H | phenyl | CH₃ |
| 273 | OCH₃ | H | CH₃ | H | CH₃ | H | phenyl | OCH₃ |

TABLE 4-continued

Structure: (R12)(R11)C-C(R13)(R14)-C(R15)(R16)-O attached to phenyl ring bearing -O- linkage to pyridine ring (A) connected to -NHC(=O)N(CH3)(B)

| Compound No. | R11 | R12 | R13 | R14 | R15 | R16 | A (pyridine) | B |
|---|---|---|---|---|---|---|---|---|
| 274 | H | H | CH3 | H | CH3 | CH3 | pyridyl | H |
| 275 | H | H | CH3 | H | CH3 | CH3 | pyridyl | CH3 |
| 276 | H | H | CH3 | H | CH3 | CH3 | pyridyl | OCH3 |
| 277 | H | H | CH3 | H | CH3 | OCH3 | pyridyl | H |
| 278 | H | H | CH3 | H | CH3 | OCH3 | pyridyl | CH3 |
| 279 | H | H | CH3 | H | CH3 | OCH3 | pyridyl | OCH3 |
| 280 | OCH3 | H | H | H | CH3 | C2H5 | pyridyl | CH3 |
| 281 | OCH3 | H | H | H | CH3 | C2H5 | pyridyl | OCH3 |
| 282 | OCH3 | H | H | H | CH3 | $^{i}C_3H_7$ | pyridyl | CH3 |
| 283 | OCH3 | H | H | H | CH3 | $^{i}C_3H_7$ | pyridyl | OCH3 |
| 284 | OCH3 | H | H | H | C2H5 | C2H5 | pyridyl | CH3 |

TABLE 4-continued
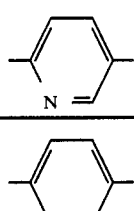
| Compound No. | $R^{11}$ | $R^{12}$ | $R^{13}$ | $R^{14}$ | $R^{15}$ | $R^{16}$ | A | B |
|---|---|---|---|---|---|---|---|---|
| 285 | $OCH_3$ | H | H | H | $C_2H_5$ | $C_2H_5$ | 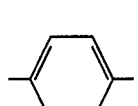 | $OCH_3$ |
| 286 | $OCH_3$ | H | H | H | $C_2H_5$ | $^nC_3H_7$ | 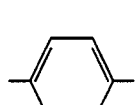 | H |
| 287 | $OCH_3$ | H | H | H | $C_2H_5$ | $^nC_3H_7$ | 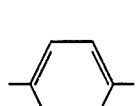 | $CH_3$ |
| 288 | $OCH_3$ | H | H | H | $C_2H_5$ | $^nC_3H_7$ | 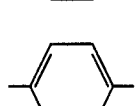 | $OCH_3$ |
| 289 | —O(CH$_2$)$_2$O— | | H | H | $CH_3$ | H | 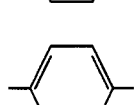 | $CH_3$ |
| 290 | —O(CH$_2$)$_2$O— | | H | H | $C_2H_5$ | H | 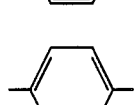 | $CH_3$ |
| 291 | —O(CH$_2$)$_2$O— | | H | H | $C_2H_5$ | H | 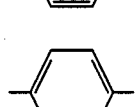 | $OCH_3$ |
| 292 | —O(CH$_2$)$_2$O— | | H | H | $^iC_3H_7$ | H | 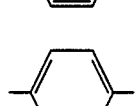 | H |
| 293 | —O(CH$_2$)$_2$O— | | H | H | $^iC_3H_7$ | H | 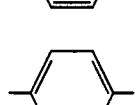 | $CH_3$ |
| 294 | —O(CH$_2$)$_2$O— | | H | H | $^iC_3H_7$ | H | 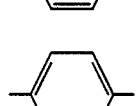 | $OCH_3$ |
| 295 | —O(CH$_2$)$_2$O— | | $CH_3$ | H | $CH_3$ | H | | $CH_3$ |

TABLE 4-continued

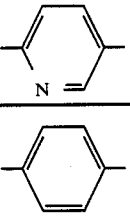

| Compound No. | $R^{11}$, $R^{12}$ | $R^{13}$ | $R^{14}$ | $R^{15}$ | $R^{16}$ | A | B |
|---|---|---|---|---|---|---|---|
| 296 | —O(CH$_2$)$_2$O— | CH$_3$ | H | CH$_3$ | H |  | OCH$_3$ |
| 297 | —O(CH$_2$)$_2$O— | H | H | CH$_3$ | CH$_3$ | 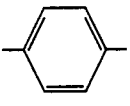 | CH$_3$ |
| 298 | —O(CH$_2$)$_2$O— | H | H | CH$_3$ | CH$_3$ | | OCH$_3$ |
| 299 | —O(CH$_2$)$_2$O— | H | H | CH$_3$ | C$_2$H$_5$ | 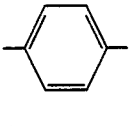 | H |
| 300 | —O(CH$_2$)$_2$O— | H | H | CH$_3$ | C$_2$H$_5$ | 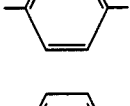 | CH$_3$ |
| 301 | —O(CH$_2$)$_2$O— | H | H | CH$_3$ | C$_2$H$_5$ | 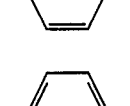 | OCH$_3$ |
| 302 | —O(CH$_2$)$_2$O— | H | H | CH$_3$ | $^i$C$_3$H$_7$ | 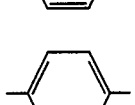 | CH$_3$ |
| 303 | —O(CH$_2$)$_2$O— | H | H | CH$_3$ | $^i$C$_3$H$_7$ | 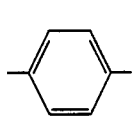 | OCH$_3$ |
| 304 | —O(CH$_2$)$_2$O— | H | H | C$_2$H$_5$ | C$_2$H$_5$ | 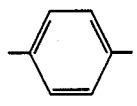 | CH$_3$ |
| 305 | —O(CH$_2$)$_2$O— | H | H | C$_2$H$_5$ | C$_2$H$_5$ | 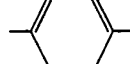 | OCH$_3$ |
| 306 | —O(CH$_2$)$_2$O— | H | H | C$_2$H$_5$ | $^n$C$_3$H$_7$ | 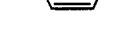 | H |

TABLE 4-continued

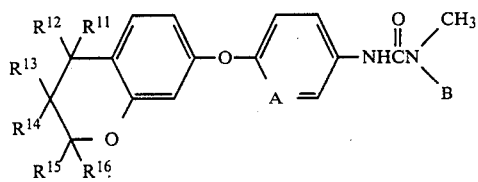

| Compound No. | $R^{11}$ | $R^{12}$ | $R^{13}$ | $R^{14}$ | $R^{15}$ | $R^{16}$ | A | B |
|---|---|---|---|---|---|---|---|---|
| 307 | —O(CH$_2$)$_2$O— | | H | H | C$_2$H$_5$ | $^n$C$_3$H$_7$ | pyridine | CH$_3$ |
| 307 | | | | | | | phenyl | |
| 308 | —O(CH$_2$)$_2$O— | | H | H | C$_2$H$_5$ | $^n$C$_3$H$_7$ | phenyl | OCH$_3$ |
| 309 | CH$_3$ | CH$_3$ | H | —CCl$_2$— | | CH$_3$ | phenyl | CH$_3$ |
| 310 | CH$_3$ | CH$_3$ | H | —CCl$_2$— | | CH$_3$ | phenyl | OCH$_3$ |
| 311 | spiro cyclobutane-cyclohexane with OCH$_3$ | | | | | | phenyl | H |
| 312 | spiro cyclobutane-benzofused with OCH$_3$ | | | | | | phenyl | CH$_3$ |
| 313 | spiro cyclobutane-benzofused with OCH$_3$ | | | | | | phenyl | OCH$_3$ |
| 314 | spiro cyclopropane-benzofused with OCH$_3$ | | | | | | phenyl | H |

TABLE 4-continued
| Compound No. | R11 | R12 | R13 | R14 | R15 | R16 | A | B |
|---|---|---|---|---|---|---|---|---|
| 315 | | | | | | |  | CH3 |
| | 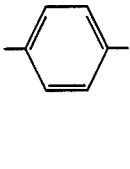 | | | | | | | |
| 316 | | | | | | |  | OCH3 |
| | 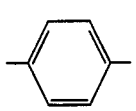 | | | | | | | |
| 317 | CH3 | CH3 | H | H | CH3 | OH | 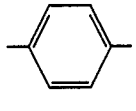 | H |
| 318 | CH3 | CH3 | H | H | CH3 | OH | 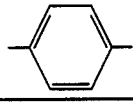 | CH3 |
| 319 | CH3 | CH3 | H | H | CH3 | OH | 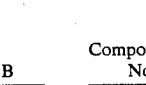 | OCH3 |
TABLE 5
| Compound No. | R17 | R18 | R19 | R20 | A | B |
|---|---|---|---|---|---|---|
| 320 | CH3 | H | H | H |  | CH3 |
TABLE 5-continued
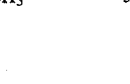
| Compound No. | R17 | R18 | R19 | R20 | A | B |
|---|---|---|---|---|---|---|
| 321 | CH3 | H | H | H | 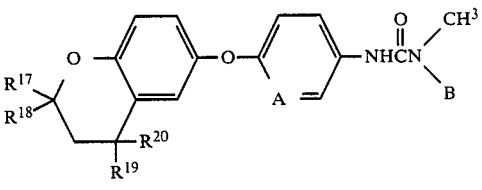 | OCH3 |

TABLE 5-continued

Structure:
R17, R18 on carbon with R19, R20; O-linked chroman attached via O to phenyl-O-A-NHC(=O)N(CH3)B

| Compound No. | R17 | R18 | R19 | R20 | A | B |
|---|---|---|---|---|---|---|
| 322 | CH3 | H | H | H | (phenyl) | H |
| 323 | CH3 | H | H | H | (phenyl) | CH3 |
| 324 | CH3 | H | H | H | (phenyl) | OCH3 |
| 325 | CH3 | CH3 | H | H | (pyridyl, N) | CH3 |
| 326 | CH3 | CH3 | H | H | (pyridyl, N) | OCH3 |
| 327 | CH3 | CH3 | H | H | (phenyl) | CH3 |
| 328 | CH3 | CH3 | H | H | (phenyl) | OCH3 |
| 329 | H | H | CH3 | CH3 | (phenyl) | CH3 |
| 330 | H | H | CH3 | CH3 | (phenyl) | OCH3 |
| 331 | CH3 | OCH3 | H | H | (phenyl) | H |
| 332 | CH3 | OCH3 | H | H | (phenyl) | CH3 |
| 333 | CH3 | OCH3 | H | H | (phenyl) | OCH3 |

TABLE 6

Structure: benzofuran with R21, R22 substituents; O-linked to phenyl-O-A-NHC(=O)N(CH3)B

| Compound No. | R21 | R22 | A | B |
|---|---|---|---|---|
| 334 | $^i$C3H7 | H | (phenyl) | H |
| 335 | $^i$C3H7 | H | (phenyl) | CH3 |
| 336 | $^i$C3H7 | H | (phenyl) | OCH3 |
| 337 | $^i$C4H9 | H | (phenyl) | CH3 |
| 338 | $^i$C4H9 | H | (phenyl) | OCH3 |
| 339 | H | C2H5 | (phenyl) | CH3 |
| 340 | H | C2H5 | (phenyl) | OCH3 |

TABLE 6-continued

[Structure: benzofuran-O-A-NHC(O)N(CH3)B with R21, R22]

| Compound No. | R21 | R22 | A | B |
|---|---|---|---|---|
| 341 | H | nC3H7 | phenyl | H |
| 342 | H | nC3H7 | phenyl | CH3 |
| 343 | H | nC3H7 | phenyl | OCH3 |
| 344 | H | iC3H7 | phenyl | CH3 |
| 345 | H | iC3H7 | phenyl | OCH3 |

TABLE 7

[Structure with R23, R24, R25, R26]

| Compound No. | R23 | R24 | R25 | R26 | A | B |
|---|---|---|---|---|---|---|
| 346 | H | H | CH3 | H | pyridyl | CH3 |
| 347 | H | H | CH3 | H | pyridyl | OCH3 |
| 348 | H | H | CH3 | H | phenyl | CH3 |

TABLE 7-continued

[Structure with R23, R24, R25, R26]

| Compound No. | R23 | R24 | R25 | R26 | A | B |
|---|---|---|---|---|---|---|
| 349 | H | H | CH3 | H | phenyl | OCH3 |
| 350 | H | H | CH3 | CH3 | phenyl | H |
| 351 | H | H | CH3 | CH3 | phenyl | CH3 |
| 352 | H | H | CH3 | CH3 | phenyl | OCH3 |

TABLE 8

[Structure with R27, R28, R29]

| Compound No. | R27 | R28 | R29 | A | B |
|---|---|---|---|---|---|
| 353 | H | CH3 | CH3 | phenyl | CH3 |
| 354 | H | CH3 | CH3 | phenyl | OCH3 |

TABLE 9

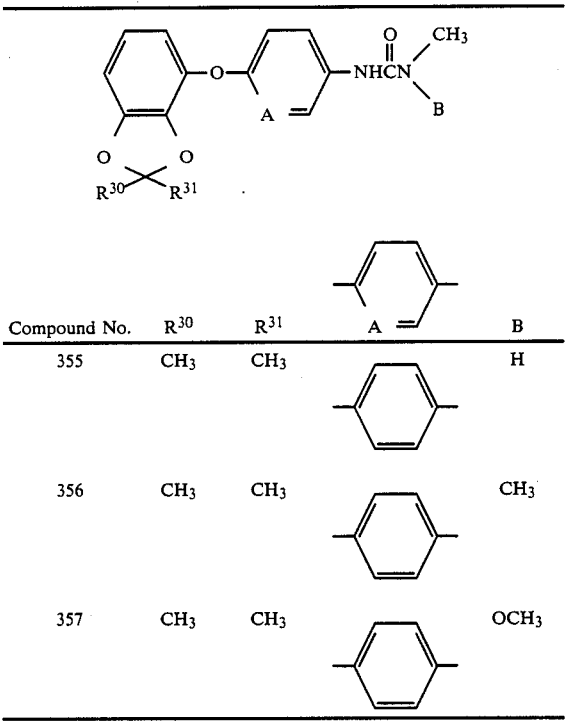

| Compound No. | $R^{30}$ | $R^{31}$ | A | B |
|---|---|---|---|---|
| 355 | CH₃ | CH₃ | (1,4-phenylene) | H |
| 356 | CH₃ | CH₃ | (1,4-phenylene) | CH₃ |
| 357 | CH₃ | CH₃ | (1,4-phenylene) | OCH₃ |

TABLE 10

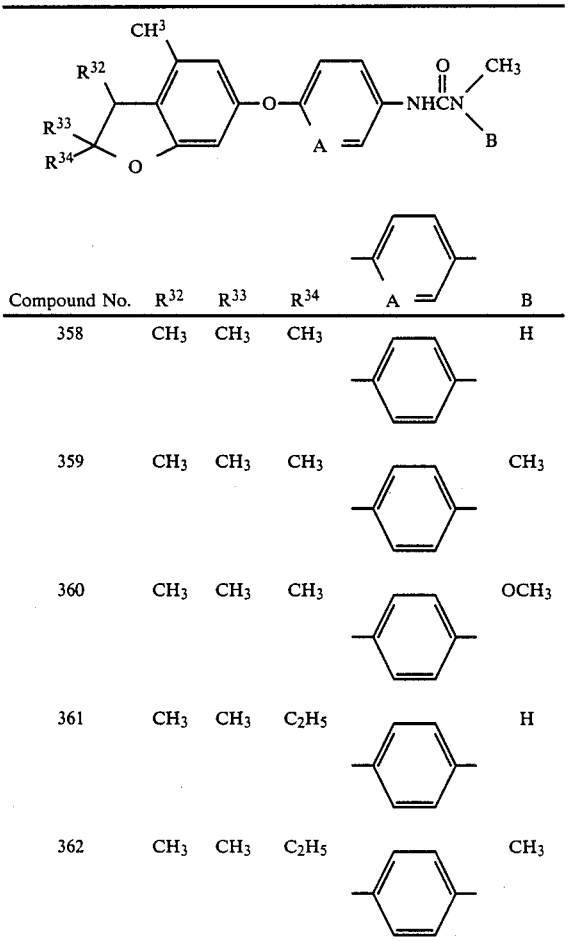

| Compound No. | $R^{32}$ | $R^{33}$ | $R^{34}$ | A | B |
|---|---|---|---|---|---|
| 358 | CH₃ | CH₃ | CH₃ | (1,4-phenylene) | H |
| 359 | CH₃ | CH₃ | CH₃ | (1,4-phenylene) | CH₃ |
| 360 | CH₃ | CH₃ | CH₃ | (1,4-phenylene) | OCH₃ |
| 361 | CH₃ | CH₃ | C₂H₅ | (1,4-phenylene) | H |
| 362 | CH₃ | CH₃ | C₂H₅ | (1,4-phenylene) | CH₃ |

TABLE 10-continued

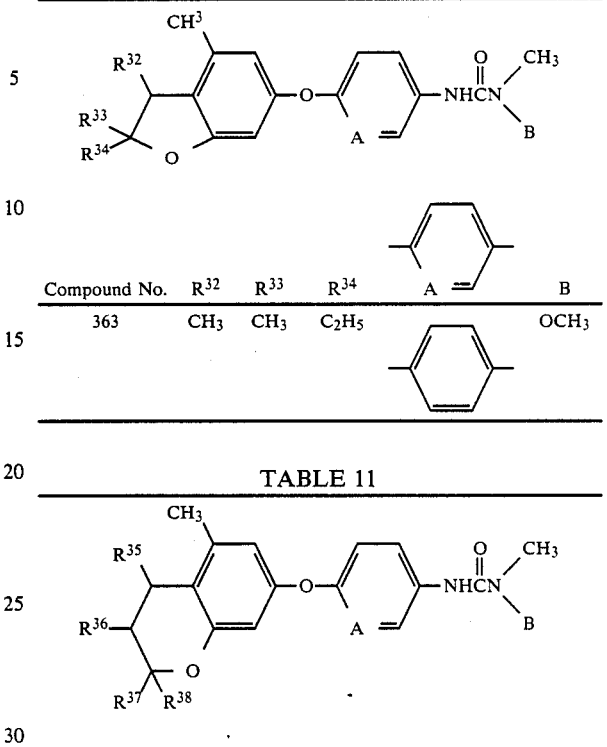

| Compound No. | $R^{32}$ | $R^{33}$ | $R^{34}$ | A | B |
|---|---|---|---|---|---|
| 363 | CH₃ | CH₃ | C₂H₅ | (1,4-phenylene) | OCH₃ |

TABLE 11

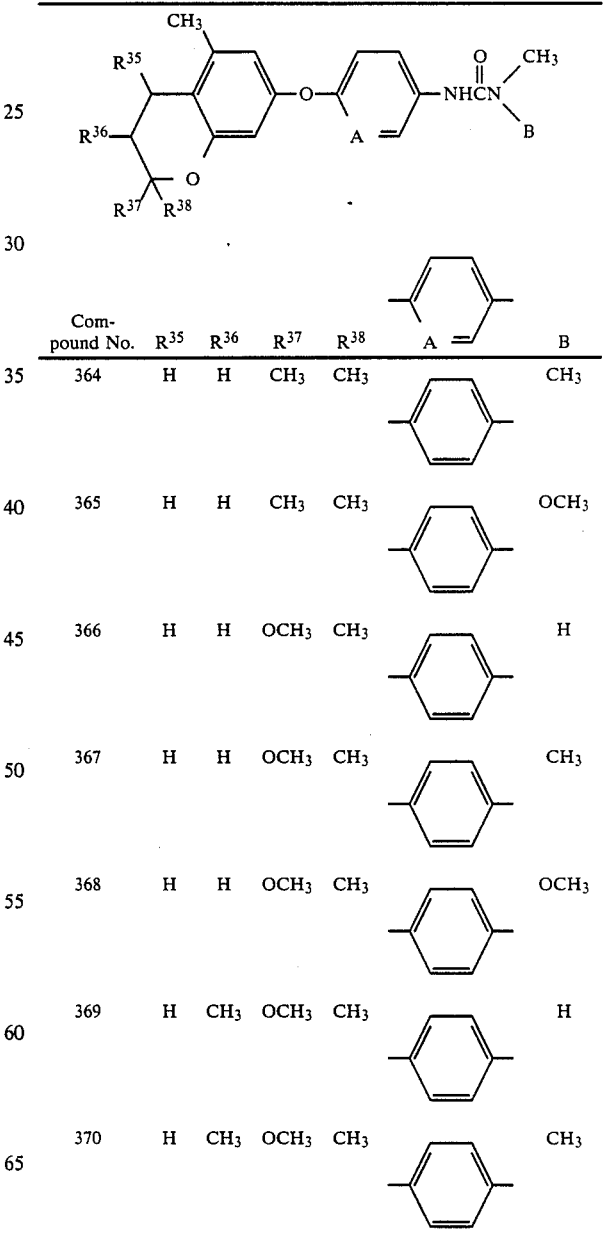

| Compound No. | $R^{35}$ | $R^{36}$ | $R^{37}$ | $R^{38}$ | A | B |
|---|---|---|---|---|---|---|
| 364 | H | H | CH₃ | CH₃ | (1,4-phenylene) | CH₃ |
| 365 | H | H | CH₃ | CH₃ | (1,4-phenylene) | OCH₃ |
| 366 | H | H | OCH₃ | CH₃ | (1,4-phenylene) | H |
| 367 | H | H | OCH₃ | CH₃ | (1,4-phenylene) | CH₃ |
| 368 | H | H | OCH₃ | CH₃ | (1,4-phenylene) | OCH₃ |
| 369 | H | CH₃ | OCH₃ | CH₃ | (1,4-phenylene) | H |
| 370 | H | CH₃ | OCH₃ | CH₃ | (1,4-phenylene) | CH₃ |

TABLE 11-continued

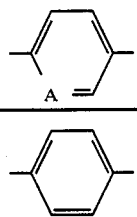

| Compound No. | R³⁵ | R³⁶ | R³⁷ | R³⁸ | A | B |
|---|---|---|---|---|---|---|
| 371 | H | CH₃ | OCH₃ | CH₃ | ⌬ | ⌬—OCH₃ |

The compound of formula (I) provided by this invention can be produced, for example, by reacting an aminopyridine or an aniline derivative represented by the following formula (II)

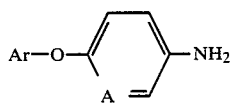

wherein Ar and A are as defined with regard to formula [I],
with methyl isocyanate, N,N-dimethylcarbamoyl chloride or N-methoxy-N-methylcarbamoyl chloride.

The compound of formula [II] used in the above reaction can be produced by a synthesis route consisting of the following reactions (1) and (2).

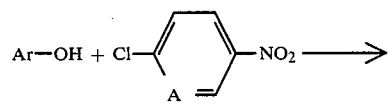 (1)

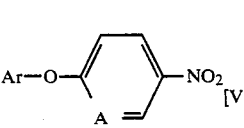

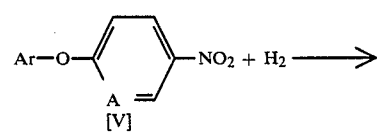 (2)

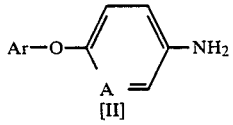

In performing the reaction (1), known reaction means of forming an aromatic ether compound by reaction of a phenolic hydroxyl group with an aryl chloride may be applied. Specifically, it can be carried out by stirring the reaction mixture at a temperature of 20° to 150° C., for 0.5 to 10 hours in an aromatic hydrocarbon (e.g., benzene, toluene, xylene), in an aprotic polar solvent (e.g., N,N-dimethylformamide, 1-methyl-2-pyrrolidone) or in their mixture in the presence of a base such as sodium hydroxide, potassium hydroxide, sodium carbonate and potassium carbonate. After the reaction, the compound [V] can be isolated by a known means such as column chromatography.

On the other hand, known means of producing an aromatic amine by reducing an aromatic nitro compound with hydrogen may be applied to the practice of the reaction (2). Specifically, the reduction with hydrogen can be carried out at a temperature of 20° to 200° C. under normal pressure to 20 kg/cm² of hydrogen in an inert solvent such as benzene, toluene, xylene, methanol, ethanol or ethyl acetate in the presence of an ordinary reducing catalyst such as Raney nickel or palladium-carbon. After the reaction, the compound [II] can be isolated by operations including removal of the catalyst, removal of the solvent, and as required, recrystallization.

Referential Examples 39 and 41 given hereinbelow illustrate the synthesis of compound [V] by the reaction (1). Synthesis of compound [II] by the reaction (2) is illustrated in Referential Examples 40, 42, 45, 47 and 48 given hereinbelow.

Among the compounds of general formula [V], compounds of the following general formula [V-1]

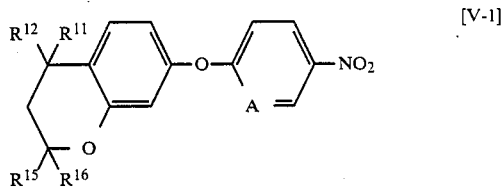

in which R¹⁶ is a lower alkoxy group or a hydroxyl group,
can also be produced by a synthesis route consisting of the following reactions (3) and (4).

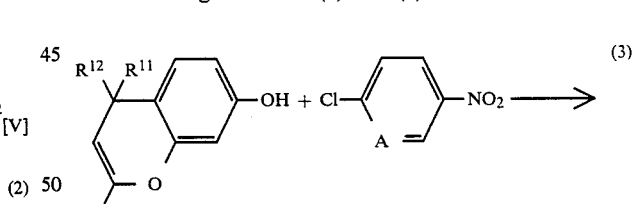 (3)

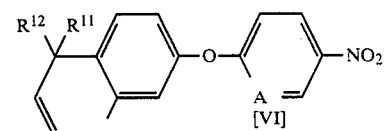 [VI]

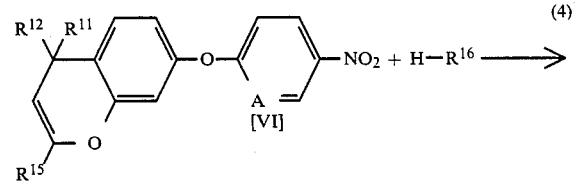 (4)

-continued

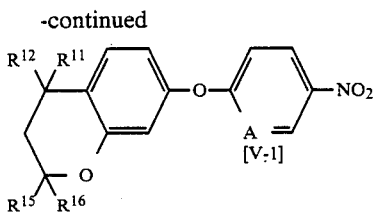

After the reaction (3), the compound [VI] can be isolated by the same operations as in the case of obtaining the compound [V] by the above reaction (1).

The reaction (4) proceeds by heating the reaction mixture at 40° to 120° C. in the absence of solvent or in an inert solvent such as acetone, dioxane, benzene or toluene in the presence of an acid catalyst such as hydrochloric acid, sulfuric acid and Amberlyst-15 ®. After the reaction, the compound [V-1] can be isolated by recrystallization, column chromatography, etc. after optionally removing the catalyst and the solvent.

Synthesis of the compound [VI] by the reaction (3) is shown in Referential Example 43, and synthesis of the compound [V-1] by the reaction (4), in Referential Examples 44 and 46.

Among the compounds of general formula [V], compounds of general formula [V-2]

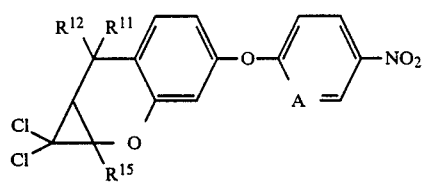

may also be synthesized from the compound [VI] in accordance with the following reaction (5).

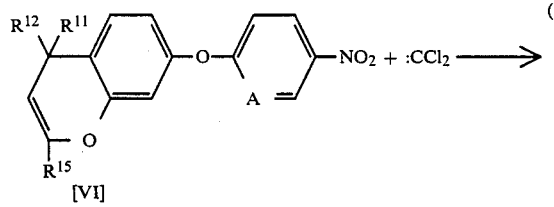

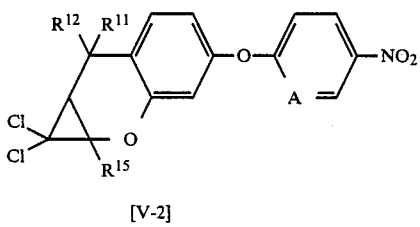

Known procedures of reacting a cyclohexene ring with dichlorocarbene to introduce a dichloromethylene group into the double bond portion of the cyclohexene ring may be applied to the practice of the reaction (5). Specifically, the reaction (5) proceeds by stirring the compound [VI], chloroform and sodium or potassium hydroxide in the absence of solvent or in water as a solvent in the presence of a quaternary ammonium salt such as benzyltrimethylammonium chloride.

Referential Example 48 illustrates the production of a compound of general formula [V-2] by the reaction (5).

Use of a base in the reaction of the compound of formula [II] with the carbamoyl chloride can increase the yield of the product. Examples of the base are pyridines such as pyridine, picoline, lutidine, and collidine, tertiary amines such as triethylamine, 1,8-diazabicyclo[5,4,0]undecene-7 and N,N-dimethylaniline, and inorganic bases such as sodium bicarbonate, potassium bicarbonate, sodium carbonate, potassium carbonate, sodium hydroxide and potassium hydroxide. The amount of the base used is from 0.5 to 20, preferably from 1 to 10, as the molar ratio to the carbamoyl chloride.

The reaction of the compound [II] with methyl isocyanate proceeds in the absence of a catalyst, but as required, may be carried out in the presence of 0.1 to 5 mole%, based on the compound [II], of a tertiary amine such as triethylamine.

The use of a reaction solvent is not necessary, but there may be used a solvent inert to the reaction, for example an aromatic hydrocarbon such as benzene, toluene and xylene, a halogenated hydrocarbon such as chloroform, dichloromethane, carbon tetrachloride, dichloroethane, trichloroethane, tetrachloroethane, chlorobenzene or dichlorobenzene, tetrahydrofuran, ethyl acetate or dimethylformamide, either alone or in combination.

The reaction is carried out by mixing 1 mole of the aminopyridine derivative or aniline derivative [II] and 0.8 to 3 moles, preferably 1 to 2 moles, of methyl isocyanate or the carbamoyl chloride with or without the base in the absence of solvent or in the aforesaid solvent, and stirring the mixture at a temperature of −20° to 100° C., preferably 0° to 80° C., for 0.3 to 30 hours.

After the reaction, the final desired product can be obtained by various separation methods shown in Examples given hereinbelow.

According to another embodiment of producing the compound of formula [I], the compound of formula [I] can be produced by reacting an isocyanate derivative represented by the following formula [III]

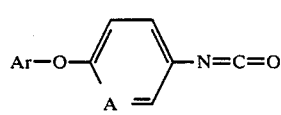

wherein Ar and A are as defined with regard to formula [I],
with an amine compound represented by the following formula [IV]

wherein B is as defined with regard to formula [I].

The isocyanate derivative [III] may be obtained by subjecting the compound [II] to a known means of reacting an aniline with phosgene to synthesize a phenyl isocyanate. Referential Example 49 given hereinbelow illustrate synthesis of one example of the compound of formula [III].

Known means of reacting an isocyanate ester with an amine to form a urea may be applied to the practice of the reaction of the isocyanate derivative [III] with the amine [IV]. The reaction may be carried out without a reaction solvent. If desired, however, there may be used a solvent inert to the reaction, for example an aromatic hydrocarbon such as benzene, toluene or xylene, a halogenated hydrocarbon such as chloroform, dichloromethane, carbon tetrachloride, dichloroethane, trichloroethane, tetrachloroethane, chlorobenzene or dichlorobenzene, tetrahydrofuran, dioxane, ethyl acetate and dimethylformamide.

The reaction is carried out by mixing 1 mole of the isocyanate derivative and 0.8 to 5 moles, preferably 1 to 2 moles, of the amine in the absence of a solvent or in the aforesaid solvent, and stirring the mixture at a temperature of −20° to 100° C., preferably 0° to 50° C., for 0.5 to 30 hours.

After the reaction, the desired product may be isolated by a conventional procedure such as the one shown in Example 3 given hereinbelow.

Guidelines for the synthesis of the compounds of the general formula Ar-OH used in the synthesis of the compounds [V] by the reaction (1) are shown in the reaction schemes given in the column of Synthesis Method in Table 12. Precursor Nos. 1 to 38 in Table 12 correspond respectively to Referential Examples 1 to 38 given hereinbelow. For example, the precursor for which a synthesis method is described in Referential Example 1 is one example of compounds which belong to the precursor No. 1.

Table 12 also describes literature references which are closely related to the reaction schemes of the synthesis methods.

It is believed that one skilled in the art can easily understand the method of synthesis of Ar-OH when he refers to Table 12 and Referential Examples 1 to 38.

Japanese patent application No. 279,193/1985 cited as reference for the precursor No. 2 was filed on the basis of an invention made by two of the inventors of the present application and has not yet been published. Precursor No. 2 may be synthesized in accordance with this method by reacting 1 mole of 1,3-dihydroxybenzene and about 0.5 to 5 moles of a ketone in the presence or absence of a solvent using an acid catalyst such as hydrochloric acid, sulfuric acid or a cation exchange resin at room temperature to 120° C. for 2 to 30 hours.

In the reaction scheme for precursor No. 5, the aforesaid reaction technique can be applied to the first reaction, and the subsequent hydrogenation reaction is well known per se.

There has been no prior example in which the precursor No. 24 shown in Table 12 was synthesized by the synthesis route shown in the reaction scheme in Table 12. In the reaction scheme, the reaction of a ketone with ethylene glycol to form a 5-membered ring comprising an ethylenedioxy group is well known per se, and the reaction of forming the phenolic hydroxyl group by the reaction of hydrogen on phenylbenzyl ether is also well known. Hence, the precursor 24 can be easily synthesized by following this reaction scheme and Referential Example 24.

The reaction for producing precursor No. 26 is neither known heretofore, and was discovered for the first time by the inventors of the present application. This reaction proceeds by reacting the two reactants under ice cooling in the presence of an alcohol of the formula $R_{15}$—H using an acid catalyst such as sulfuric acid, toluenesulfonic acid or a cation exchange resin.

In Table 12, Bz in Table 12 stands for the benzyl group.

The method of synthesizing the starting material of the following formula

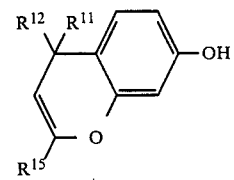

used in the reaction (3) above is described, for example, in U.S. Pat. No. 4,323,505.

Referential Examples 1 to 38 given hereinbelow illustrate synthesis of typical compounds of general formula Ar—OH.

Referential Examples 39 and 41 show synthesis of intermediates coming within the scope of compounds [V] in accordance with the reaction (1). Referential Examples 40, 42, 45 and 47 show synthesis of intermediates coming within the scope of compounds [II] in accordance with the reaction (2). Referential Example 43 shows synthesis of an intermediate coming within the scope of compounds [VI] in accordance with the reaction (3). Referential Example 48 shows synthesis of an intermediate falling within the scope of compound [V-2] in accordance with the reaction 5 and subsequent synthesis of an intermediate coming within the scope of compound [II] by the reaction 2. Referential Example 49 shows synthesis of an intermediate falling within the scope of compound [III].

In these Referential Examples, column chromatography was carried out using a silica gel column and hexane-ethyl acetate mixture as an eluent.

TABLE 12

| Precursor No. | Ar—OH | Synthesis method | Reference |
|---|---|---|---|
| 1 | | | J. C. S., 2254 (1948) |
| 2 | | | Japanese Pat. Appln. No. 279193/1985 |
| 3 | | | J. Am. Chem. Soc., 70, 3619 (1948) |
| 4 | | | Aust. J. Chem., 22, 601 (1969) |

TABLE 12-continued

| Precursor No. | Ar—OH | Synthesis method | Reference |
|---|---|---|---|
| 5 | | | Japanese Pat. Appln. No. 279193/1985 |
| 6 | | | J. Org. Chem., 35, 2904 (1970) |
| 7 | | | J. Org. Chem., 28, 2469 (1963) |

TABLE 12-continued
| Precursor No. | Ar—OH | Synthesis method | Reference |
|---|---|---|---|
| | | | Indian J. Chem., 7, 1004 (1969) |
| 8 | | | Japanese Laid-Open Pat. Publn. No. 149263/1976 |
| 9 | | | Japanese Laid-Open Pat. Publn. No. 149263/1976 |
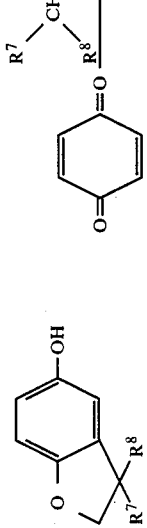

TABLE 12-continued
| Precursor No. | Ar—OH | Synthesis method | | | Reference |
|---|---|---|---|---|---|
| 10 | | | | | J. Org. Chem., 29, 2579 (1964) |
| 11 | | | | | J. Org. Chem., 29, 2579 (1964) |
| 12 | | | | | J. Org. Chem., 29, 2579 (1964) |
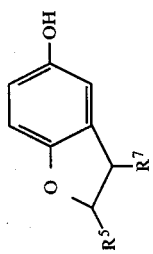

TABLE 12-continued
| Precursor No. | Ar—OH | Synthesis method | Reference |
|---|---|---|---|
| 13 | 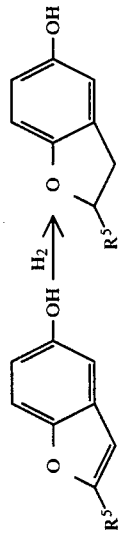 | 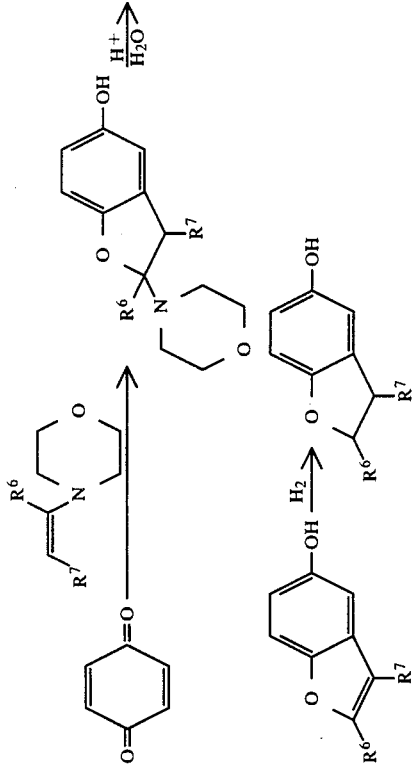 | J. Org. Chem., 29, 2579 (1964) |
| | | | J. Org. Chem., 26, 240 (1961); |
| 17 | 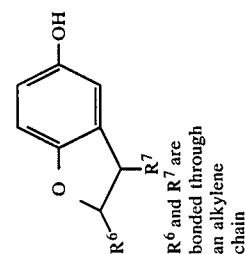 | 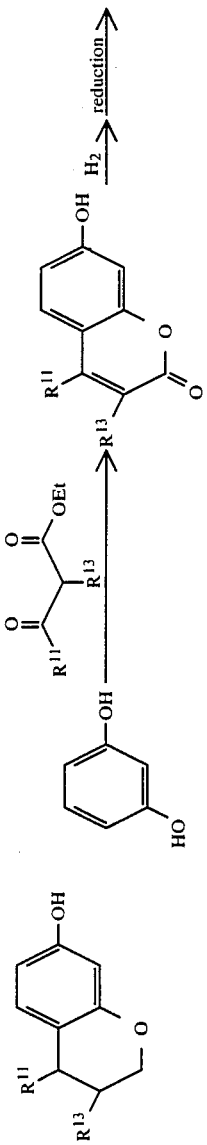 | J. Am. Chem. Soc., 94, 9166 (1972) |

TABLE 12-continued

| Precursor No. | Ar—OH | Synthesis method | Reference |
|---|---|---|---|
| 13 | (chroman structure with CH₃, CH₃, OH) | via methoxycrotonate → lactone → reduction → chroman-ol | Bull. Soc. Chim. France, 776 (1957); J. Am. Chem. Soc., 94, 9166 (1972) |
| 14 | (catechol with R⁹R¹⁰ ketal, OH) R⁹, R¹⁰: alkyl, or R⁹ and R¹⁰ are bonded through an alkylene chain | catechol + R⁹COR¹⁰ → acetonide → Pb(OAc)₄ → hydrolysis | Aust. J. Chem., 33, 675 (1980) |
| 15 | (catechol with R⁹R¹⁰ ketal, OH) R⁹: alkoxy R¹⁰: H, alkyl | HO—Ar—OH + R¹⁰—CR₃⁹ → ketal | Ger. Offen. 2,550,965 |

TABLE 12-continued

| Precursor No. | Ar—OH | Synthesis method | Reference |
|---|---|---|---|
| 16 | (chromene-type phenol structures) | Reduction of coumarin with $H_2$ gives chromanol; further reduction opens ring to give 2,4-dihydroxyphenylpropanol (−$H_2O$) | J. Am. Chem. Soc., 94, 9166 (1972) |
| 19 | 2-(3-hydroxyalkyl)-substituted phenol with R, $R^{15}$, $R^{16}$ substituents (R: H, $CH_3$; $R^{15}$: $CH_3$; $R^{16}$: H, $CH_3$) | Resorcinol derivative + diene → alkylated phenol intermediate | Journal of Jap. Chem. Soc., 1987 (1972) |
| 20 | 4,4-dimethyl-2-methylchroman (7-OH) | 4,4-dimethyl-2-methyl-4H-chromene → ($H_2$) → 4,4-dimethyl-2-methylchroman (7-OH) | Japanese Laid-Open Pat. Publn. No. 5475/1981 |

TABLE 12-continued

| Precursor No. | Ar—OH | Synthesis method | Reference |
|---|---|---|---|
| 21 | | | Japanese Laid-Open Pat. Publn. No. 109779/82 |
| 22 | R$^{15}$: alkyl<br>R$^{16}$: H, alkyl<br>or R$^{15}$ and R$^{16}$ are bonded through an alkylene chain | | Angew. Chem. Int. Ed. Engl. 21, 225 (1982) |
| 23 | R$^{11}$: alkoxy<br>R$^{15}$: alkyl<br>R$^{16}$: H, alkyl | | Angew. Chem. Int. Ed. Engl. 21, 225 (1982) |

TABLE 12-continued

| Precursor No. | Ar—OH | Synthesis method | Reference |
|---|---|---|---|
| 24 | | | U.S. Pat. No. 4,003,919 |
| 25 | | R: H, CH$_3$<br>R$^{11}$, R$^{13}$, R$^{15}$: H, alkyl<br>R$^{16}$: alkyl<br>R$^{16}$, alkoxy or R$^{11}$ and R$^{15}$ are bonded through an alkylene chain | |
| 26 | | R$^{11}$: H, alkyl<br>R$^{15}$: alkoxy | |

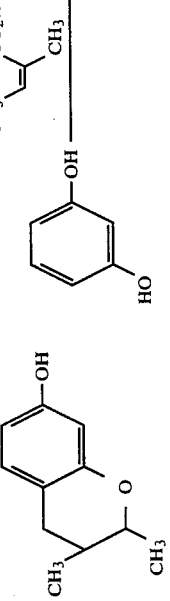

TABLE 12-continued

| Precursor No. | Ar—OH | Synthesis method | Reference |
|---|---|---|---|
| 30 | | | J. Chem. Soc., 1190 (1958) |
| 31 | | | Ger. Offen. 1,945,212 |

TABLE 12-continued

| Precursor No. | Ar—OH | Synthesis method | Reference |
|---|---|---|---|
| 32 | [structure] | U.S. Pat. No. 4,003,919 | |
| 33 | [structure] | | Bull. Soc. Chim. France, 776 (1957); J. Am. Chem. Soc., 94, 9166 (1972) |

TABLE 12-continued
| Precursor No. | Ar—OH | Synthesis method | Reference |
|---|---|---|---|
| 34 | 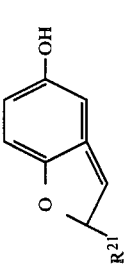 | 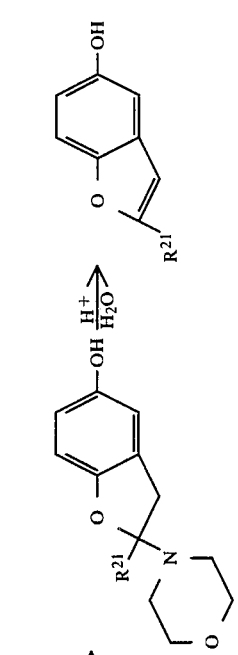 | J. Org. Chem., 29, 2579 (1964) |
| 35 | 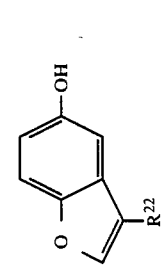 | 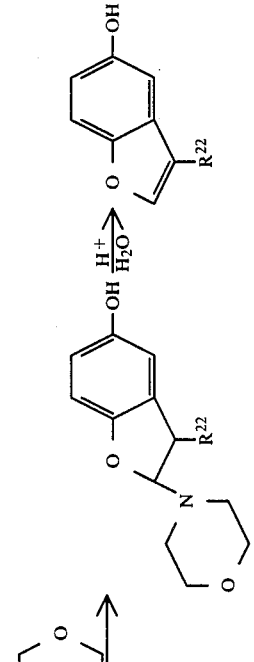 | J. Org. Chem., 29, 2579 (1964) |
| 36 | 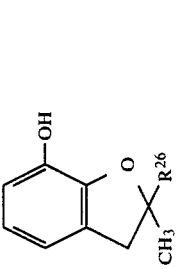 | 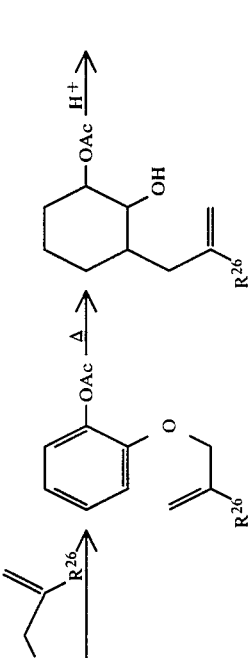 | J. Org. Chem., 28, 2468 (1963); Indian J. Chem., 7, 1004 (1969) |

TABLE 12-continued

| Precursor No. | Ar—OH | Synthesis method | Reference |
|---|---|---|---|
| 37 | (chromanol structure with OH, O, CH₃, R²⁹) | (synthesis from catechol + R²⁹ diene to chromanol) | Ger. Offen. 1,945,212 |
| 38 | (benzodioxole structure with OH, R³⁰, R³¹) | (synthesis from pyrogallol + R³⁰R³¹C(OCH₃)₂) | Ger. Offen. 2,221,706 |

R³⁰, R³¹: alkyl

The compounds of formula [I] provided by this invention have low phytotoxicity to useful crops and are useful for controlling or eradicating undesired vegetation at low dosasges. Thus, according to this invention, there can be provided a herbicidal composition comprising a herbicidally effective amount of at least one compound of formula [I] and an agriculturally acceptable diluent or carrier.

The herbicidal composition may be in various formulations such as emulsifiable concentrates, wettable powders, dusts, or granules. Suitable agriculturally acceptable diluents or carriers include, for example, solid diluents or carriers such as clay, talc, bentonite, kaolin, diatomaceous earth, white carbon, vermiculite, slaked lime, and silica sand, and liquid diluents or carriers including solvents and surfactants, such as alkylbenzenesulfate esters, alkylbenzenesulfonate salts, polyoxyethylene glycol ether, polyoxyethylene alkyl aryl ethers, polyoxyethylene sorbitan monoalkylates, sodium alkylsulfates, sodium alkylnaphthalenesulfonates, and sodium ligninsulfonate.

The herbicidal composition of the invention may contain the compound of formula [I] in a herbicidally effective amount which, for example, is about 0.5 to about 70% by weight, based on the weight of the composition, and is usually from 0.5 to 20% by weight for granules or dusts, and from 5 to 70% by weight for emulsifiable concentrates or wettable powders, based on the weight of the composition.

According to this invention there may also be provided a method of controlling the growth of undesired vegetation which comprises applying a herbicidally effective amount of at least one compound represented by formula [I] to the weeds or the locus of such weeds.

The compound of formula [I], either as such or as the aforesaid composition or as a dilution or suspension of it in water, etc., can be applied to the locus where undesired vegetation is growing or is likely to grow. In the method of controlling the growth of undesired vegetation, the rate of application of the compound of formula [I] may be varied depending upon the formulation, the crop to be applied, the weed to be applied, climatic conditions, etc. For example, it is about 50 g to about 3 kg/hectare.

The herbicide of this invention exhibits a high herbicidal efficacy by soil treatment or foliar treatment against various weeds, particularly various weeds in upland farms, for example important weeds such as barnyard grass (*Echinochloa crus-galli*), fingergrass (*Digitaria sanguinalis*), dent foxtail (*Alopecurus aequalis*), cocklebur (*Xanthium strumarium*), blackjack (*Bidens pilosa*), and velvet leaf (*Abutilan theophrasti*) and also weeds of Compositae, Rubiaceae, Scrophulariaceae, Solanaceae, Umbelliferae, Violaceae, Oxalidaceae, Euphorbiaceae, Brassicaceae, Caryophyllaceae, Amaranthaceae, Chenopudiaceae, and Polygonaceae. Particularly, in foliar treatment, it can be used safely on important crops, for example gramineous crops such as wheat, corn and rice and leguminous crops such as soybean and peanut, and can kill a wide range of weeds at low dosages.

The herbicide of this invention may also be applied to lawns, orchards, pastures and non-agricultural lands.

As desired, the herbicide of this invention may be used as a mixture with, or jointly with, other agricultural chemicals such as another herbicide, a fungicide or an insecticide, or a fertilizer. Examples of the other agricultural chemicals include methyl 2-[4-(2,4-dichlorophenoxy)phenoxy]propionate, isobutyl 2-[4-(4-chlorophenoxy)phenoxy]propionate, 2-[4-(3,5-dichloro-2-pyridyloxy)phenoxy]propionic acid, butyl 2-[4-(5-trifluoromethyl-2-pyridyloxy)phenoxyl]propionate, dimethyl tetrachloroterephthalate, isopropyl-N-phenylcarbamate, 4-chloro-2-butynyl-N-(3-chlorophenyl)carbamate, methyl N-(3,4-dichlorophenyl)carbamate, S-ethyl N,N-diisobuthylthiocarbamate, S-(2,3,3-trichloro-2-propenyl) N,N-diisopropylthiocarbamate, 2-chloro-N-isopropylacetanilide, 2-chloro-2',6'-diethyl-N-methoxymethylacetanilide, 2-chloro-N-ethoxymethyl-2'-ethyl-6'-methylacetanilide, 2-chloro-2'-ethyl-N-(2-methoxy-1-methylethyl)-6'-methylacetanilide, 3',4'-dichloropropionanilide, ethyl 2-[N-benzoyl-N-(3,4-dichlorophenyl)amino]propionate, 3-(4-chlorophenyl)-1-methoxy-1-methylurea, 3-(3,4-dichlorophenyl)-1-methoxy-1-methylurea, 2-(3,5-dichlorophenyl)-2-(2,2,2-trichloroethyl)oxirane, 3-amino-2,5-dichlorobenzoic acid, 3,6-dichloro-2-methoxybenzoic acid, 2,6-dinitro-N,N-dipropyl-4-trifluoromethylaniline, 1,2-dimethyl-3,5-diphenyl-1H-pyrazolium methyl sulfate, S-2,3-dichloroallyl-N,N-diisopropyl thiolcarbamate, and ethyl N-benzoyl-N-(3-chloro-4-fluorophenyl)-2-aminopropionate.

BEST MODE FOR PRACTICING THE INVENTION

The best mode of practicing the invention will be shown below by examples of producing the synthesis intermediates of the compounds of this invention, examples of producing the compounds of this invention, examples of the herbicidal composition of this invention and examples of herbicidal tests.

REFERENTIAL EXAMPLE 1

2,3-Dihydro-3-ethyl-6-hydroxybenzofuran (a precursor of compound No. 13)

A mixture of 5.0 g of 2',4'-dihydroxypropiophenone, 5.4 g of benzyl bromide, 6.2 g of potassium carbonate and 50 ml of acetone was refluxed for 7 hours. After cooling, the solid was separated by filtration. The filtrate was concentrated, and the residue was separated by column chromatography to give 4.7 g of 4'-benzyloxy-2'-hydroxypropiophenone as a white solid (yield 61%, melting point 111.5°–112.5° C.). Then, a mixture of 4.5 g of this solid, 3.5 g of ethyl bromoacetate, 6.1 g of potassium carbonate and 45 ml of acetone was refluxed for 7.5 hours. After cooling, the solid was separated by filtration. The filtrate was concentrated, and the residue was purified by column chromatography to give 5.8 g of ethyl 3-benzyloxy-6-propionylphenoxyacetate as white crystals (yield 97%, melting point 81.5° to 82.0° C.). This ester (5.5 g) was dissolved in a solution composed of 1.3 g of potassium hydroxide and 55 ml of methanol, and the solution was stirred at room temperature for 2 hours to hydrolyze the ester. The hydrolysis product was worked up in a customary manner to give 3.9 g (yield 77%) of 3-benzyloxy-6-propionylphenoxyacetic acid as a pale yellowish orange solid. Then, 9.3 g of sodium acetate and 39 ml of acetic anhydride were added to this solid, and the mixture was heated at 155° C. for 30 minutes. The solvent was evaporated, and the residue was purified by column chromatography to give 2.8 g (yield 95%, melting point 69.5°–70.5° C.) of 6-benzyloxy-3-ethylbenzofuran as a white solid. Palladium (5%)-carbon (0.27 g) and 27 ml of acetic acid were added to 2.7 g of the resulting benzofuran, and the mixture was stirred at room temperature for 3 hours in an atmosphere of nitrogen. The catalyst was separated by filtration, and the filtrate was concentrated and then purified by column chromatography to give 1.7 g (yield 90%) of the desired product as a pale orange liquid.

REFERENTIAL EXAMPLE 2

2,3-Dihydro-6-hydroxy-2,2,3-trimethylbenzofuran (a precursor of compound No. 6)

A 100 ml three-necked flask equipped with a condenser and a thermometer was charged with 11 g (0.1 mole) of resorcinol, 8.6 g (0.1 mole) of isopropyl methyl ketone and 1.3 g (12% by weight based on resorcinol) of a cation exchange resin (Amberlyst-15) as a catalyst. The mixture was stirred at 100° C. in a nitrogen atmosphere for 10 hours. After cooling, the catalyst was separated by filtration, and the residue was purified by column chromatography to give 11.8 g (yield 66%) of the desired productg as colorless needle-like crystals. Melting point: 67.5° C.

REFERENTIAL EXAMPLE 3

2,3-Dihydro-6-hydroxybenzofuran (a precurosr of compound No. 11)

A mixture of 18 g of resorcinol, 12 g of chloroacetonitrile, 12 g of zinc chloride and 100 ml of diethyl ether was bubbled with HCl gas at room temperature with stirring. The white crystals that precipitated were collected by filtration, and suspended in 200 ml of water. The suspension was refluxed for 0.5 hour. After cooling, the white crystals were collected by filtration and refluxed together with 16 g of potassium acetate and 100 ml of ethanol for 0.5 hour. After cooling, 300 ml of water was added and 2N-HCl was added until the solution became acidic. As a result, 20 g of 2,3-dihydro-7-hydroxy-3-oxobenzofuran was obtained as brown crystals. The compound was acetylated in a customary manner. The resultig acetylated product (3.0 g) was stirred together with 0.3 g of 10% palladium-carbon and 50 ml of ethanol at 60° C. for 4 hours in an atmosphere of hydrogen to give 2.0 g of white crystals. The crystals were hydrolyzed in a customary manner to give 1.0 g (total yield 41%) of the desired product as a brown liquid.

REFERENTIAL EXAMPLE 4

2,3-Dihydro-2-sec-butyl-6-hydroxybenzofuran (a precursor of compound No. 29)

A mixture of 9.0 g of potassium hydroxide, 150 ml of ethanol and 10 g of 2,3-dihydro-6-hydroxy-3-oxobenzofuran was stirred at room temperature for 0.5 hour, and then 9.7 g of ethyl methyl ketone was added. The mixture was stirred at room temperature for 16 hours. 2N-HCl was added until the aqueous layer became acidic. The mixture was then extracted with ethyl acetate. The extract was dried over magnesium sulfate, and ethyl acetate was evaporated. The resulting crude crystals were recrystallized from hexane-ethyl acetate to give 7.4 g of brown crystals. Sodium borohydride (4.0 g) was gradually added to a mixture of 2.3 g of these crystals, 1.5 g of sodium hydroxide and 100 ml of water, and then the mixture was stirred at 100° C. for 2 hours. The mixture was acidified with 2N-HCl and extracted with ethyl acetate. After evaporating ethyl acetate, 0.1 g of 10% palladium-carbon and 30 ml of ethanol were added to the residue, and the mixture was stirred at room temperature for 3 hours in an atmosphere of hydrogen. The palladium-carbon was separated by filtration, and the filtrate was concentrated. The residue was purified by column chromatography to give 2.0 g (yield 36%) of the desired product as a colorless liquid.

REFERENTIAL EXAMPLE 5

2,3-Dihydro-2,3-dimethyl-6-hydroxybenzofuran (a precursor of compound No. 17)

A mixture of 1.9 g of resorcinol, 1.8 g of 3-methoxy-2-butanone, 0.2 g of Amberlyst-15 and 2 ml of toluene was stirred at 90° C. for 10 hours. After cooling, the catalyst was separated, and the filtrate was concentrated. The residue was purified by column chromatography to give 1.7 g of 2,3-dimethyl-6-hydroxybenzofuran as pale yellow crystals. The crystals were dissolved in 20 ml of acetic acid, and 0.2 g of 5% palladium-carbon was added. The mixture was stirred at room temperature for 12 hours in an atmosphere of hydrogen. The crude product was purified by column chromatography to give 1.5 g (yield 54%) of the desired product as a brown liquid.

REFERENTAIL EXAMPLE 6

2,3-Dihydro-2,2-dimethyl-6-hydroxybenzofuran (a precursor of compound No. 32)

3-Benzyloxyphenol (5.0 g), 2.0 g of isobutyraldehyde, 0.1 g of methanesulfonic acid and 50 ml of toluene were put into a flask equipped with the Dean-Stark condenser, and stirred under reflux for 4 hours. Low-boiling compounds were evaporated under reduced pressure. The residue was purified by column chromatography to give 3.8 g of 6-benzyloxy-2,3-dihydro-2,2-dimethylbenzofuran as a brown liquid. This product was dissolved in ethanol, and 0.4 g of 5% palladium-carbon was added. The mixture was stirred at room temperature for 8 hours in an atmosphere of hydrogen. The catalyst was separated by filtration, and the filtrate was concentrated. The residue was purified by column chromatography to give 2.0 g (yield 50%) of the desired product as a pale yellow liquid.

REFERENTIAL EXAMPLE 7

2,3-Dihydro-5-hydroxy-2-methylbenzofuran (a precursor of compound No. 60)

A mixture of 4.6 g of hydroquinone, 7.5 g of hydroquinone diacetate, 13.8 g of potassium carbonate, 12.1 g of allyl bromide and 60 ml of acetone was refluxed for 4 hours. After cooling, the solid was separated by filtration, and the filtrate was concentrated. The residue was purified by column chromatography to give 13.6 g (yield 85%) of 4-acetoxyphenyl allyl ether as a pale orange liquid. Then, 4.0 g of this liquid was dissolved in N,N-dimethylaniline, and the solution was heated at 210° C. for 6 hours. The crude product was purified by column chromatography to give 3.5 g (yield 88%) of 4-acetoxy-2-allylphenol. This phenol was dissolved in a methanol solution of potassium hydroxide and hydrolyzed. The hydrolyzed product was worked up in a customary manner, and purified by column chromatography to give 2.2 g (yield 82%) of 2-allylhydroquinone as a pale orange solid. To 1.7 g of this solid were added 8.5 ml of acetic acid and 3.4 ml of 47% hydrobromic acid, and the mixture was heated at 75° C. for 16 hours. The reaction mixture was neutralized with aqueous sodium carbonate and extracted with ethyl acetate. The extract was dried over magnesium sulfate, and concentrated. The residue was purified by column chromatography to give 1.4 g (yield 82%) of the desired product as a reddish brown liquid.

REFERENTIAL EXAMPLE 8

2,3-Dihydro-3,3-dimethyl-5-hydroxybenzofuran (a precursor of compound No. 88)

A solution composed of 46 ml of isobutyraldehyde and 1 ml of triethylamine was refluxed, and a mixture of 5.0 g of p-quinone and 46 ml of isobutyraldehyde was added. The mixture was refluxed for 15 minutes. Low-boiling compounds were evaporated under reduced pressure. The residue was purified by column chromatography to give 2-(1-formyl-1-methylethyl)hydroquinone as a deep orange liquid. This liquid was reduced with 0.87 g of sodium borohydride in 83 ml of ethanol, and then refluxed for 1.5 hours in 85 ml of toluene together with a catalytic amount of p-toluenesulfonic acid. The crude product was purified by column chromatography to give 4.8 g of the desired product having a reddish orange color.

REFERENTIAL EXAMPLE 9

2,3-Dihydro-3,3-dimethyl-5-hydroxy-2-methoxybenzofuran (a precursor of compound No. 95)

A mixture of 46 ml of isobutyraldehyde and 1.0 ml of triethylamine was refluxed, and a mixture of 5.0 g of p-quinone and 46 ml of isobutyraldehyde was gradually added dropwise to the mixture. The reaction mixture was distilled under reduced pressure, and the residue was refluxed for 1.5 hours together with 50 ml of methanol and 0.5 g of p-toluenesulfonic acid. The reaction mixture was extracted with ethyl cetate. The extract was concentrated, and the residue was purified by column chromatography to give 7.0 g (yield 79%) of the desired product as a brown liquid.

REFERENTIAL EXAMPLE 10

2,3-Dihydro-2-ethoxy-3-ethyl-5-hydroxybenzofuran (a precursor of compound No. 107)

To a solution of 20 g of p-quinone in 200 ml of toluene was added 39 g of 1-morpholino-1-butene at room temperature, and the mixture was stirred for 6 hours. Toluene was evaporated, and the residue was dissolved in ethanol. The solution was added dropwise to 150 ml of 4N-HCl, and the mixture was stirred at room temperature, and extracted with ethyl acetate. The extract was concentrated, and the residue was purified by column chromatography to give 18.6 g (yield 48%) of the desired product as a brown liquid.

REFERENTIAL EXAMPLE 11

2,3-Dihydro-3-ethyl-5-hydroxybenzofuran (a precursor of compound No. 65)

The adduct of p-quinone and enamine shown in Referential Example 10 (5.0 g) was stirred together with 150 ml of 4N-HCl at room temperature for 16 hours. The crude product was purified by column chromatography to give 1.6 g (yield 49%) of 3-ethyl-5-hydroxybenzofuran. This product was hydrogenated in isopropanol at room temperature for 7 hours in the presence of a catalytic amount of Raney nickel to give 1.6 g (yield 99%) of the desired product as a brown liquid.

REFERENTIAL EXAMPLE 12

2,3-Dihydro-5-hydroxy-2-sec-butylbenzofuran (a precursor of compound No. 73)

Referential Example 11 was repeated except that 4-methyl-2-morpholino-1-pentene was used as the enamine. The desired compound was obtained as a brown liquid in a yield of 41%.

REFERENTIAL EXAMPALE 13

1,2,3,4,4a,9b-hexahydro-8-hydroxydibenzofuran (a precursor of compound No. 117)

Referential Example 11 was repeated except that 1-morpholino-1-cyclohexene was used as the enamine. The desired compound was obtained as a brown liquid in a yield of 63%.

REFERENTIAL EXAMPLE 14

2-Ethyl-5-hydroxy-2-methyl-1,3-dioxolane (a precursor of compound No. 129)

Catechol (20 g), 55 ml of methyl ethyl ketone, 10 mg of p-toluenesulfonic acid and 100 ml of toluene were put into a flask equipped with the Dean-Stark condenser, and refluxed for 36 hours to give 23.6 of 2-ethyl-2-methyl-1,3-dioxolane as a colorless liquid. The liquid was stirred in acetic acid together with 127 g of Pb(OAc)$_4$ at 140° C. for 9.5 hours. The crude product was purified by column chromatography to give 7.2 g of the acetoxylated product as a brown liquid. This liquid was hydrolyzed using potassium hydroxide, methanol and water to give 5.8 g (yield 18%) of the desired product as a brown liquid.

REFERENTIAL EXAMPLE 15

2-Ethoxy-5-hydroxy-2-methyl-1,3-dioxolane (a precursor of compound No. 138)

A solution composed of 5.0 g of 1,2,4-trihydroxybenzene, 9.7 g of triethyl orthoacetate and 50 ml of toluene-carbon tetrachloride (1:1) was refluxed for 1.5 hours. The solvent was evaporated, and the residue was purified by column chromatography to give 6.7 g (yield 86%) of the desired product as pale brown crystals having a melting point of 86° to 87° C.

REFERENTIAL EXAMPLE 16

2,3-Dihydro-7-hydroxy-4H-1-benzopyran (a precursor of compound No. 155)

5.0 g of 7-hydroxycoumarin was hydrogenated using 0.5 g of 5% palladium-carbon as a catalyst at 80° C. for 9 hours in 13 ml of acetic acid and 25 ml of ethyl acetate. The reaction residue was recrystallized from hexane-ethyl acetate to give 4.9 g of white crystals (m.p. 135°–137° C.). The crystals were dissolved in 15 ml of tetrahydrofuran, and the solution was added dropwise at room temperature to a mixture of 0.9 g of lithium aluminum hydride and 10 ml of tetrahydrofuran, and the mixture was then refluxed for 3 hours. The reaction mixture was worked up in a customary manner, and the product was dissolved in 30 ml of toluene without purification. A catalytic amount of p-toluenesulfonic acid was added, and the mixture was heated at 120° C. for 6 hours. The reaction mixture was worked up in a customary manner. The residue after concentration was purified by column chromatography to give 1.6 g (yield 36%) of the desired product as pink crystals.

REFERENTIAL EXAMPLE 17

2,3-Dihydro-3,4-dimethyl-7-hydroxy-4H-1-benzopyran (a precursor of compound No. 227)

Resorcinol (5.5 g) and 7.2 g of ethyl 2-methylacetoacetate were stirred at 10° C. for 3 hours in the presence of a catalytic amount concentrated sulfuric acid to give 7.8 g (yield 83%) of 3,4-dimethyl-7-hydroxycoumarin. The product was hydrogenated and dehydrated as in Referential Example 16 to give 5.7 g (78%) of the desired product as a pale brown liquid.

REFERENTIAL EXAMPLE 18

2,3-Dihydro-4,4-dimethyl-7-hydroxy-4H-1-benzopyran (a precursor of compound No. 166)

A mixture of 103 g of resorcinol and 4.6 g of conc. sulfuric acid was heated at 130° C. with stirring, and 58 g of methyl 3,3-dimethylacrylate was added. The mixture was heated at 130° C. for 3 hours with stirring. The reaction mixture was worked up in a customary manner, and the residue after concentration was purified by column chromatography to give 24 g (yield 27%) of 4,4-dimethyl-7-hydroxycoumarin (melting point 84°–85° C.). The product was worked up in the same way as in Referential Example 16 to give 16.8 g (yield 75%) of the desired product as colorless crystals (melting point 88°–88.5° C.).

REFERENTIAL EXAMPLE 19

2,3-Dihydro-7-hydroxy-2-methyl-4H-1-benzopyran (a precursor of compound No. 164)

A 100 ml autoclave was charged wtih 20 g of resorcinol, 12 g of butadiene, 4 ml of $H_3PO_4$ and 60 ml of toluene, and purged with nitrogen. The mixture was then heated at 100° C. for 3.5 hours. The crude product was purified by column chromatography to give 24.1 g (yield 82%) of the desired product as a brown liquid.

REFERENTIAL EXAMPLE 20

2,3-Dihydro-7-hydroxy-2,4,4-trimethyl-4H-1-benzopyran (a precursor of compound No. 180)

A 100 ml autoclave was charged with 6.0 g of 7-hydroxy-2,4,4-trimethyl-4H-1-benzopyran synthesized by the method of Japanese Laid-Open Patent Publication No. 5475/1981, 1.0 g of 5% palladium-carbon and 20 ml of ethanol, and hydrogenation was carried out at 85° C. The resulting product was recrystallized from n-hexanetoluene to give 5.2 g (86%) of the desired product as colorless crystals (melting point 97°–98° C.).

REFERENTIAL EXAMPLE 21

3,4-Dihydro-7-hydroxy-2,2,4-trimethyl-2H-1-benzopyran (a precursor of compound No. 184)

7-Hydroxy-2,2,4-trimethyl-2H-1-benzopyran synthesized by the method of Japanese Laid-Open Patent Publication No. 109779/1982 was hydrogenated as in Referential Example 20. The product was purified by column chromatography to give the desired product as colorless liquid in a yield of 83%.

REFERENTIAL EXAMPLE 22

2,3-Dihydro-7-hydroxy-2-isopropyl-4H-1-benzopyran (a precursor of compound No. 216)

Pyrrolidine (14.2 g) was added dropwise at room temperature to a mixture of 15 g of 4-acetylresorcinol, 14.4 g of isobutyraldehyde and 100 ml of toluene, and the mixture was stirred at room temperature for 6 hour, and thereafter refluxed for 8 hours. The crude product was purified by column chromatography to give 11.4 g of pale yellow crystals. The hydroxyl group of the resulting compound was benzylated with benzyl bromide, and then the product was reduced with sodium borohydride in methanol and further dehydrated with p-toluenesulfonic acid in toluene. Then, the product was hydrogenated at room temperature for 13 hours in ethanol, in the presence of 5% palladium-carbon. The solvent was evaporated, and the residue was purified by column chromatography to give 6.5 g (yield 34%) of the desired product as a pale yellow liquid.

REFERENTIAL EXAMPLE 23

2,3-Dihydro-2,2-dimethyl-7-hydroxy-4-methoxy-4H-1-benzopyran (a precursor of compound No. 187)

7-Benzyloxy-2,3-dihydro-2,2-dimethyl-4-oxobenzopyran synthesized as in Referential Example 22 was dissolved in 60 ml of methanol, and reduced with 1.0 g of sodium borohydride at room temperature. The product was dissolved in 10 ml of tetrahydrofuran, and the solution was added dropwise to a mixture of 1.0 g of 60% sodium hydride and 5 ml of tetrahydrofuran. After generation of hydrogen ceased, 4.3 g of methyl iodide was added dropwise, and the mixture was further stirred for 2.5 hours at room temperature. The reaction mixture was extracted with ethyl acetate. The extract was concentrated, and the residue was dossolved in 30 ml of ethanol and hydrogenated at room temperature for 8 hours in the presence of 5% palladium-carbon catalyst. The crude product was purified by column chromatography to give 2.2 g (yield 58%) of the desired product as a pale brown liquid.

REFERENTIAL EXAMPLE 24

2,3-Dihydro-4,4-ethylenedioxy-7-hydroxy-2-methyl-4H-1-benzopyran (a precursor of compound No. 289)

A mixture of 2.2 g of 7-benzyloxy-2,3-dihydro-2-methyl-4-oxobenzopyran, 4.5 g of ethylene glycol, 1.8 g of triethyl orthoformate, 80 mg of p-toluenesulfonic acid and 20 ml of toluene was refluxed for 5.5 hours. The reaction product was purified by column chromatography to give 2.6 g of the acetal. The acetal was hydrogenated at room temperature for 9.5 hours in ethanol with 5% palladium-carbon. The hydrogenated product was purified by column chromatography to give 1.4 g (yield 76%) of the desired product as pale pink crystals.

REFERENTIAL EXAMPLE 25

2,3-Dihydro-7-hydroxy-2-methoxy-2-methyl-4H-1-benzopyran (a precursor of compound No. 258)

Methyl vinyl ketone (7.7 g) was added dropwise under ice cooling to a solution composed of 11 g of resorcinol, 11.7 g of trimethyl orthoformate and 0.1 ml of conc. sulfuric acid. After the addition, the mixture was stirred at room temperature for 2 hours. The reaction mixture was neutralized with a saturated aqueous solution of sodium bicarbonate, and then extracted with ethyl acetate. The residue left after evaporation of the solvent as purified by column chromatography to give 12.5 g (yield 70%) of the desired product as colorless crystals (melting point 107°–108° C.).

REFERENTIAL EXAMPLE 26

2,3-Dihydro-2-ethoxy-7-hydroxy-4H-1-benzopyran (a precursor of compound No. 221)

A solution of 1.6 g of acrolein diethylacetal in 4 ml of ethanol was added dropwise under cooling to a solution composed of 1.1 g of resorcinol, 0.05 g of conc. sulfuric acid and 6 ml of ethanol. While maintaining the temperature at less than 10° C., the mixture was stirred for 2 hours. The reaction mixture was neutralized with an aqueous solution of sodium carbonate and extracted with ethyl acetate. The solvent was evaporated, and the residue was purified by column chromatography to give 1.2 g (yield 63%) of the desired product as a colorless liquid.

REFERENTIAL EXAMPLE 27

2,3-Dihydro-2,3-dimethyl-7-hydroxy-4H-1-benzopyran (a precursor of compound No. 239)

Resorcinol (11 g) and 20 g of tiglic acid were heated together with 15 g of zinc chloride at 180° C. for 30 minutes with stirring. After cooling, the reaction mixture was extracted with ethyl acetate. The extract was concentrated to give 13 g of crystals. The crystals were benzylated with benzyl bromide in acetone in the presence of potassium carbonate, dissolved in a mixture of ethanol and tetrahydrofuran, and reduced with sodium borohydride. The reaction product was dehydrated in toluene with a catalytic amount of p-toluenesulfonic acid. The dehydrated product was purified by column chromatography to give the benzyl ether (colorless liquid). The liquid was hydrogenated in ethanol at room temperature for 15 hours using a 5% palladium-carbon catalyst. The crude product was purified by column chromatography to give 10.5 g (yield 59%) of the desired product as a pale yellow liquid.

REFERENTIAL EXAMPLE 28

2,3-Dihydro-2,4-dimethyl-7-hydroxy-4H-1-benzopyran (a precursor of compound No. 230)

Resorcinol (11 g) and 17.2 g of crotonic acid were heated at 180° C. for 30 minutes together with 15 g of zinc chloride with stirring. The reaction mixture was extracted with ethyl acetate, and purified by column chromatography to give 7.3 g of 2,3-dihydro-7-hydroxy-2-methyl-4-oxobenzopyran. The OH group of the compound was benzylated in a customary manner, and then the product was reacted with $CH_3MgBr$ in tetrahydrofuran. The product was then hydrogenated in ethanol at room temperature for 13 hours in the presence of 5% palladium-carbon. The hydrogenated product was purified by column chromatography to give 4.2 g (yield 24%) of the desired product as a brown liquid.

REFERENTIAL EXAMPLE 29

2,3-Dihydro-7-hydroxy-2,2,3-trimethyl-4H-1-benzopyran (a precursor of compound No. 275)

A mixture of 5.0 g of 2,3-dihydro-2,2-dimethyl-7-hydroxy-4-oxobenzopyran, 3.8 g of 37% aqueous formaldehyde, 10.5 g of potassium hydroxide and 50 ml of ethanol was heated at 50° C. for 3 hours with stirring. The reaction mixture was acidified with 2N-HCl and extracted with ethyl acetate. The extract was purified by column chromatography to give 1.8 g of the enone. In a customary manner, the enone was hydrogenated, and then reacted with benzyl bromide to give 7-benzyloxy-2,3-dihydro-4-oxo-2,2,3-trimethylbenzpyran. The product was reduced with 2.0 g of sodium borohydride in methanol-tetrahydrofuran, and then dehydrated in toluene using 0.1 g of p-toluenesulfonic acid. This compound was hydrogenated in a customary manner to give 1.4 g (yield 27%) of the desired product as a pale brown liquid.

REFERENTIAL EXAMPLE 30

2,3-Dihydro-7-hydroxy-4-methoxy-4H-1-benzopyran (a precursor of compound No. 211)

Under ice cooling, $AlCl_3$ (3 molar equivalent) was added little by little to a solution composed of 11 g of resorcinol, 12.7 g of 2-chloropropionyl chloride and 120 ml of nitrobenzene. After the addition, the mixture was heated at 40° to 50° C. for 4 hours with stirring. The reaction mixture was worked up and purified in a customary manner to give 4.1 g of 2,3-dihydro-7-hydroxy-4-oxobenzopyran. The resulting compound was benzylated, reduced with sodium borohydride in methanol, and then methylated with methyl iodide in tetrahydrofuran in the presence of sodium hydride. In a customary manner, the methylated product was hydrogenated to give 1.7 g (yield 9.4%) of the desired product as a colorless liquid.

REFERENTIAL EXAMPLE 31

2,3-Dihydro-6-hydroxy-2-methyl-4H-1-benzopyran (a precursor of compound No. 320)

Referential Example 19 was repeated except that hydroquinone was used instead of resorcinol. There was obtained the desired product as a colorless liquid (yield 65%; b. p. 160°-162° C./12 mm).

REFERENTIAL EXAMPLE 32

2,3-Dihydro-6-hydroxy-2-methoxy-2-methyl-4H-1-benzopyran (a precursor of compound No. 332)

Referential Example 25 was repeated except that hydroquinone was used instead of resorcinol. Pale brown crystals were obtained in a yield of 36%.

REFERENTIAL EXAMPLE 33

2,3-Dihydro-4,4-dimethyl-6-hydroxy-4H-1-benzopyran (a precursor of compound No. 329)

A mixture of 8.8 g of hydroquinone, 5 g of methyl 3,3-dimethylacrylate and 0.4 g of conc. sulfuric acid was heated at 130° C. for 4 hours. The reaction mixture was cooled, and then 15 ml of toluene was added. The crystals that precipitated were separated by filtration. The filtrate was concentrated and then distilled under reduced pressure to give 4.6 g (yield 70%) of 3,4-dihydro-4,4-dimethyl-6-hydroxycoumarin as pale pink crystals (melting point 95°-96° C.). The crystals (3.0 g) were dissolved in 10 ml of tetrahydrofuran, and the solution was added dropwise at room temperature to a mixture of 0.9 g of lithium aluminum hydride and 20 ml of tetrahydrofuran. The mixture was then refluxed for 4 hours. The reaction mixture was worked up in a customary manner, and the crude product, without purification, was dissolved in 30 ml of toluene. A catalytic amount of p-toluenesulfonic acid was added to the solution, and the mixture was heated at 120° C. for 1.5 hours. In a customary manner, the reaction mixture was worked up, and the residue after concentration was isolated and purified by column chromatography to give 2.4 g (yield 85%) of the desired product as a yellow orange liquid.

REFERENTIAL EXAMPLE 34

5-Hydroxy-2-isopropylbenzofuran (a precursor of compound No. 334)

In accordance with Referential Example 10, 5.0 g of an adduct was synthesized from p-quinone and 3-methyl-2-morpholino-1-butene, and stirred together with 150 ml of 4N-HCl at room temperature for 16 hours. The reaction mixture was worked up in a customary manner, and purified by column chromatography to give 1.6 g (yield 49%) of the desired product as a yellowish orange liquid.

REFERENTIAL EXAMPLE 35

3-Ethyl-5-hydroxybenzofuran (a precursor of compound No. 339)

The captioned compound was synthesized by the method of Referential Example 11.

REFERENTIAL EXAMPLE 36

2,3-Dihydro-7-hydroxy-2-methylbenzofuran (a precursor of compound No. 346)

A mixture of 10.7 g of catechol, 17.3 g of catechol diacetate, 34.5 g of potassium carbonate, 30.3 g of allyl bromide and 200 ml of acetone was refluxed for 5 hours. The reaction mixture was filtered, and the filtrate was concentrated and purified by column chromatography to give 26.5 g (yield 71%) of 2-acetoxyphenyl allyl ether as a pale yellow liquid. Ten grams of this liquid was heated at 220° to 230° C. for 1.5 hours. After cooling, the reaction mixture was purified by column chromatography to give 6.5 g (yield 65%) of 2-acetoxy-6-allylphenol as a pale yellow liquid. Then, 3.0 g of this liquid and 12 ml of an acetic acid solution of 25% hydrobromic acid were reacted at 70° C. for 6 hours. The reaction mixture was poured into ice water, neutralized with an aqueous solution of sodium bicarbonate, and extracted with ethyl acetate. The concentrate was hydrolyzed with potassium hydroxide and aqueous ethanol, and worked up in a customary manner. The product was then purified by column chromatography to give 0.7 g (yield 31%) of the desired product as a pale yellow liquid.

REFERENTIAL EXAMPLE 37

2,3-Dihydro-2,2-dimethyl-8-hydroxy-4H-1-benzopyran (a precursor of compound No. 353)

While a mixture of 10 g of catechol, 50 ml of p-xylene, 25 ml of hexane, 1 ml of phosphoric acid and 0.3 ml of water was heated at 100° C., 7.3 g of isoprene was added dropwise over 10 minutes, and the reaction was further carried out for 7 hours. After cooling, the resulting precipitate was separated by filtration. The filtrate was concentrated, and purified by column chromatography to give 1.7 g (yield 11%) of the product as a pale pink liquid.

REFERENTIAL EXAMPLE 38

2,2-Dimethyl-4-hydroxybenzodioxolane (a precursor of compound No. 355)

A mixture of 9.0 g of pyrogallol, 7.5 g of 2,2-dimethoxypropane and 100 ml of toluene was refluxed for 4.5 hours. After cooling, the reaction mixture was worked up in a customary manner and purified by column chromatography to give 2.0 g (yield 17%) of the desired product as a pale yellow solid.

REFERENTIAL EXAMPLE 39

2,3-Dihydro-2,2-dimethyl-7-(4-nitrophenoxy)-4H-1-benzopyran (an intermediate of compound No. 172)

2,3-Dihydro-2,2-dimethyl-7-hydroxy-4H-1-benzopyran (2.0 g) synthesized as in Referential Example 19, 1.8 g of p-chloronitrobenzene, 0.9 g of potassium hydroxide, 20 ml of N,N-dimethylformamide and 10 ml of toluene were put into a flask equipped with the Dean-Stark condenser, and were heated to 110° C. While removing evaporated water as an azeotrope with toluene, the reaction was carried out for 1 hour. After cooling, the reaction mixture was poured into water, and extracted with ethyl acetate. The extract was dried over magnesium sulfate, and the solvents were evaporated. The residue was purified by column chromatography to give 2.8 g (yield 84%) of the desired product as a brown liquid.

REFERENTIAL EXAMPLE 40

4-(2,3-Dihydro-2,2-dimethyl-4H-1-benzopyran-7-yl)oxyaniline (an intermediate of compound No. 172)

To 2.7 g of the nitrobenzene derivative obtained in Referential Example 39 were added 0.3 g of 5% palladium-carbon and 20 ml of ethanol, and the mixture was stirred at 40° to 50° C. for 5 hours in an atmosphere of hydrogen. The catalyst was separated by filtration, and the filtrate was concentrated to give 1.8 g (yield 72%) of the desired product as a gray powder.

REFERENTIAL EXAMPLE 41

2-(2,3-Dihydro-2,2-dimethyl-4H-1-benzopyran-7-yl)oxy-5-nitropyridine (an intermediate of compound No. 169)

Five milliliters of an N,N-dimethylformamide solution of 1.5 g of 2,3-dihydro-2,2-dimethyl-7-hydroxy-4H-1-benzopyran synthesized by the method of Referential Example 19 was added dropwise to a mixture of 0.35 g of sodium hydride and 4 ml of N,N-dimethylformamide. The mixture was stirred at room temperature for 0.5 hour, and 6 ml of an N,N-dimethylformamide solution of 2-chloro-5-nitropyridine (1.3 g) was added to the resulting reddish orange solution, and the mixture was stirred at room temperature for 5 hours. The reaction mixture was poured into 100 ml of water, and extracted with 100 ml of ethyl acetate. The extract was dried over magnesium sulfate, and concentrated. The residue was purified by column chromatography to give 2.1 g (yield 84%) of the desired product as a yellow liquid.

REFERENTIAL EXAMPLE 42

5-Amino-2-(2,3-dihydro-2,2-dimethyl-4H-1-benzopyran-7-yl)oxypyridine (an intermediate of compound No. 169)

The nitro compound obtained in Referential Example 41 (2.1 g) was dissolved in 11 ml of ethyl acetate, and 0.11 g of 5% palladium-carbon was added. Hydrogenation was carried out in accordance with the method of Referential Example 40. The filtrate was concentrated to give 1.9 g (yield 100%) of the desired product as a pale pink solid (melting point 93°-94° C.).

REFERENTIAL EXAMPLE 43

7-(4-Nitrophenoxy)-2,4,4-trimethyl-4H-1-benzopyran (an intermediate of compound No. 194)

One hundred grams of 7-hydroxy-2,4,4-trimethyl-4H-1-benzopyran (synthesized by the method of Japanese Laid-Open Patent Publication No. 5475/1981), 79 g of p-chloronitrobenzene, 42 g of potassium hydroxide, 500 ml of N,N-dimethylformamide and 500 ml of toluene were introduced into a flask equipped with the Dean-Stark condenser, and heated at 110° to 116° C. While removing the distilled water as an azeotrope with toluene, the mixture was stirred for 2 hours. The reaction mixture was cooled to room temperature, and 1 liter of water, 500 ml of ethyl acetate and 120 ml of 2N-HCl were added. The insoluble materials were separated by filtration. The filtrate was subjected to oil-water separation. The oil layer was washed with 500 ml of brine, and dried over magnesium sulfate. The solvent was evaporated. Methanol (650 ml) was added to the residue, and crystals that precipitated were collected, washed with 650 ml of hexane, and dried to give 106 g (yield 67%) of the desired product as a brown powder (melting point 80° C.).

REFERENTIAL EXAMPLE 44

2,3-Dihydro-2-methoxy-7-(4-nitrophenoxy)-2,4,4-trimethyl-4H-1-benzopyran (an imtermediate of compound No. 194)

A mixture of the 7-(4-nitrophenoxy)-2,4,4-trimethyl-4H-1-benzopyran obtained in Referential Example 43, 66 ml of methanol, 0.7 g of Amberlyst-15 and 6 ml of toluene was stirred for 4.5 hours, and Amberlyst-15 was separated by filtration. The filtrate was concentrated, and 30 ml of methanol was added. Crystals that precipitated were collected by filtration, washed with 50 ml of methanol, and dried to give 6.7 g (90%) of the desired product as a white powder (melting point 125° C.).

REFERENTIAL EXAMPLE 45

7-(4-Aminophenoxy)-2,3-dihydro-2-methoxy-2,4,4-trimethyl-4H-1-benzopyran (an intermediate of compound No. 194)

A mixture of 6.7 g of the 2,3-dihydro-2-methoxy-7-(4-nitrophenoxy)-2,4,4-trimethyl-4H-1-benzopyran obtained in Referential Example 44, 0.7 g of 5% palladium-carbon, and 67 ml of ethyl acetate was stirred at room temperature for 5.5 hours in an atmosphere of hydrogen. Palladium-carbon was separated by filtration, and the filtrate was concentrated to give 6.0 g (yield 98%) of the desired product as a yellow liquid.

REFERENTIAL EXAMPLE 46

2,3-Dihydro-2-hydroxy-7-(4-nitrophenoxy)-2,4,4-trimethyl-4H-1-benzopyran (an intermediate of compound No. 319)

A mixture of 6.5 g of the 7-(4-nitrophenoxy)-2,4,4-trimethyl-4H-1-benzopyran, 26 ml of water, 13 ml of conc. hydrochloric acid and 65 ml of acetone was refluxed for 2 hours. An 10% aqueous solution of sodium hydroxide was added to the reaction mixture to neutralize it, and then 100 ml of water and 200 ml of ethyl acetate were added, and the mixture was subjected to oil-water separation. The oil layer was washed with 50 ml of brine, dried over magnesium sulfate and concentrated. Toluene (5 ml) and 45 ml of hexane was added to the residue, and the precipitated crystals were collected by filtration, washed with 50 ml of hexane and dried to give 5.1 g (yield 70%) of a pale brown powder (mp. 159°-160° C., recrystallized from ethanol).

REFERENTIAL EXAMPLE 47

7-(4-Aminophenoxy)-2,3-dihydro-2-hydroxy-2,4,4-trimethyl-4H-1-benzopyran (an intermediate of compound No. 319)

A mixture of 5.0 g of 7-(4-nitrophenoxy)-2,4,4-trimethyl-4H-1-benzopyran, 0.5 g of 5% palladium-carbon and 50 ml of ethyl acetate was stirred at room temperature for 5.5 hours in an atmosphere of hydrogen. The palladium-carbon was separated by filtration, and the filtrate was concentrated. The residue was recrystallized from ethyl acetate-hexane to give 4.3 g (yield 93%) of the desired product as a white powder.

REFERENTIAL EXAMPLE 48

7-(4-Aminophenoxy)-2,3-dichloromethano-2,3-dihydro-2,4,4-trimethyl-4H-1-benzopyran (an intermediate of compound No. 309)

A solution of 0.02 g of benzyltrimethylammonium chloride in 5 ml of chloroform was added dropwise to a mixture of 1.6 g of 7-(4-nitrophenoxy)-2,4,4-trimethyl-4H-1-benzopyran, 20 ml of chloroform and 0.7 g of sodium hydroxide with stirring at 5° C. The mixture was stirred at room temperature for 2 hours, poured into ice water containing dilute hydrochloric acid, and extracted with dichloromethane. The extract was washed with brine, dried over sodium sulfate, and concentrated. Ethyl acetate (30 ml) and 5% palladium-carbon were added to the residue, and the mixture was stirred at 60° C. for 5 hours in an atmosphere of hydrogen. The palladium-carbon was removed by filtration, and the filtrate was concentrated. The residue was purified by column chromatography and recrystallization (dichloromethane-hexane) to give 0.74 g (yield 40%) of the desired product as colorless crystals (melting point 46° to 147° C.).

REFERENTIAL EXAMPLE 49

4-(2,3-Dihydro-2,2-dimethyl-4H-1-benzopyran-7-yl)oxyphenyl isocyanate (an intermediate of compound No. 172)

A solution of 8.1 g (0.03 mole) of the aniline derivative obtained by the method of Referential Example 40 was added dropwise at 0° C. to 60 ml of ethyl acetate into which 0.12 mole of phosgene had been blown, and the mixture was stirred for 0.5 hour. Thereafter, the mixture was refluxed for 1 hour, and the excess of phosgene was replaced by nitrogen gas. The ethyl acetate was evaporated under reduce pressure to give 8.7 g (yield 98%) of the desired product as a yellow orange liquid (IR: 2260 cm$^{-1}$).

The following Example illustrates the synthesis of typical examples of the compounds of formula [I] and their properties.

COMPOUND NO. 1

1,1-dimethyl-3-[2-(3-methyl-2,3-dihydro-6-benzofuryloxy)pyridin-5-yl]urea 2-(3-Methyl-2,3-dihydro-6-benzofuryloxy)-5-aminopyridine (0.5 g) was dissolved in 2.5 ml of pyridine, and a solution of composed 0.27 g of dimethylcarbamoyl chloride and 2.5 ml of toluene was added. A solution composed of 0.27 g of diethylcarbamoyl chloride and 2.5 ml of toluene was added, and the mixture was stirred at room temperature for 9 hours. Water and ethyl acetate were added to the reaction mixture, and the organic layer was separated. The organic layer was washed with a saturated aqueous solution of sodium chloride, and dried over anhydrous magnesium sulfate. Ethyl acetate was evaporated under reduced pressure, and the precipitated crystals were washed with n-hexane to give 0.63 g (yield 96%) of the desired product as pale brown crystals.

Melting point: 153°–154° C.

Mass spectrum: m/Z 313 (molecular ion peak).

IR spectrum (KBr disk; cm$^{-1}$) 3260, 3050, 2958, 1637, 1602, 1357, 1274, 1237, 1133, 979, 850, 842, 760.

$^1$H-NMR spectrum (CDCl$_3$ solution; ppm)

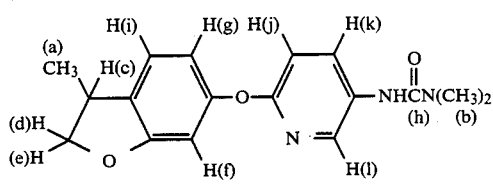

(a) 1.31 (3H, d, J=7.2 Hz), (b) 3.00 (6H, s), (c) 3.28 (1H, m), (d) 4.09 (1H, t, J=7.2 Hz), (e) 4.71 (1H, t, J=7.2 Hz), (f) 6.51 (1H, d, J=2.7 Hz), (g) 6.57 (1H, dd, J=2.7, 7.2 Hz), (h) 6.70 (1H, brs), (i) 6.92 (1H, d, J=9.0 Hz), (j) 7.08 (1H, d, J=7.2 Hz), (k) 7.91 (1H, dd, J=2.7, 9.0 Hz), (l) 8.02 (1H, d, J=2.7 Hz).

COMPOUND NO. 331

1-methyl-3-[4-(2-methoxy-2-methyl-2,3-dihydro-6-benzopyranyloxy)phenyl]urea

Methyl isocyanate (0.16 g) was added at room temperature to a solution composed of 0.4 g of 4-(2-methoxy-2-methyl-2,3-dihydro-6-benzopyranyloxy)aniline and 3.0 ml of toluene, and the mixture was stirred for 6 hours. Addition of n-hexane to the mixture yielded crystals which were collected by filtration to give the desired product as white crystals (yield not less than 97%).

Melting point: 140°–140.5° C.

Mass spectrum: m/Z 342 (molecular ion peak).

IR spectrum (KBr disk; cm$^{-1}$) 3330, 2950, 1642, 1605, 1586, 1505, 1486, 1212, 1092, 1058, 918, 872.

$^1$H-NMR spectrum (CDCl$_3$ solution; ppm)

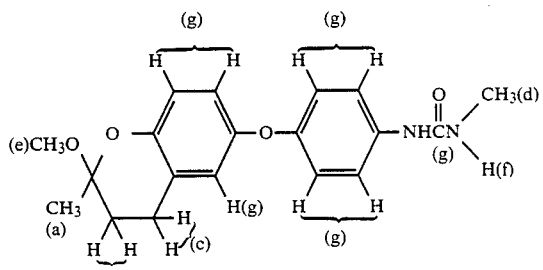

(a) 1.54 (3H, s), (b) 1.68–2.24 (2H, m), (c) 2.32–3.28 (2H, m), (d) 2.75 (3H, d, J=5.4), (e) 3.28 (3H, s), (f) 5.43 (1H, d, J=5.4), (g) 6.60–7.40 (8H, m).

COMPOUND NO. 172

1,1-Dimethyl-3-[4-(2,2-dimethyl-2,3-dihydro-7-benzopyranyloxy)phenyl]urea

A solution of 0.5 g of 4-(2,2-dimethyl-2,3-dihydro-6-benzopyranyloxy)phenyl isocyanate in 2.5 ml of toluene was added dropwise at 0° C. to a solution of 0.2 g of dimethylamine in 3 ml of toluene, and the mixture was then stirred at room temperature for 2 hours. Toluene was evaporated under reduced pressure, and the precipitated crystals were washed with n-hexane to give 0.62 g (yield 97%) of the desired product as white crystals.

Melting point: 137°–138° C.

Mass spectrum: m/Z 340 (molecular ion peak).

IR spectrum (KBr disk; cm$^{-1}$) 3310, 3040, 2940, 1640, 1602, 1370, 1210, 1147, 996, 838, 813.

$^1$H-NMR spectrum (CDCl$_3$ solution; ppm)

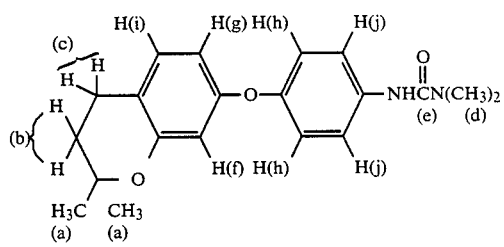

(a) 1.30 (6H, s), (b) 1.77 (2H, t, J=7.2 Hz), (c) 2.72 (2H, t, J=7.2 Hz), (d) 3.02 (6H, s), (e) 6.33 (1H, brs), (f) 6.39 (1H, d, J=2.7 Hz), (g) 6.47 (1H, dd, J=2.7, 7.2 Hz), (h) 6.96 (2H, d, J=9.0 Hz), (i) 6.97 (1H, d, J=7.2 Hz), (j) 7.34 (2H, d, J=9.0 Hz).

Other compounds of formula [I] shown in Tables 1 to 11 were synthesized in accordance with the method used to produce compound No. 1 or No. 331, and the results are shown in Table 13. The NMR spectra were measured in CDCl$_3$. The IR spectra of solid compounds were measured using KBr disks, and those of liquid compounds were measured at neat.

TABLE 13

| Compound No. | Yield (%) | Melting point (°C.) | Spectral data | |
|---|---|---|---|---|
| 2 | 94 | 153–154 | IR: | 3280 ($v_{NH}$), 1672 ($v_{c=o}$). |
| 3 | not less than 97 | 114–115 | | |
| 4 | 85 | 155–156 | IR: | 3310 ($v_{NH}$), 1642 ($v_{c=o}$). |
| 5 | not less than 97 | 110.5–112 | NMR: | 1.31 (3H, d, J=7.2), 3.18 (3H, s), 3.29 (1H, m), 3.76 (3H, s), 4.70 (1H, t, J=9.0), 5.09 (1H, dd, J=7.2, 9.0), 6.36–7.12 (3H, m), 6.96 (2H, d, J=9.0), 7.43 (2H, d, J=9.0). |
| 6 | 81 | 145–147 | NMR: | 1.22 (3H, d, J=8.1), 1.28 (3H, s), 1.47 (3H, s), 2.98 |

TABLE 13-continued

| Compound No. | Yield (%) | Melting point (°C.) | Spectral data | |
|---|---|---|---|---|
| | | | | (6H, s), 3.05 (1H, q, J=8.1), 6.24 (1H, d, J=2.7), 6.54 (1H, dd, J=2.7, 7.2), 6.81 (1H, d, J=9.0), 7.03 (1H, d, J=7.2), 7.90 (1H, dd, J=2.7, 9.0), 8.03 (1H, d, J=2.7). |
| 7 | 94 | 94–95 | NMR: | 1.22 (3H, d, J=7.2), 1.30 (3H, s), 1.49 (3H, s), 3.16 (1H, q, J=7.2), 3.22 (3H, s), 3.78 (3H, s), 6.50 (1H, d, J=2.7), 6.58 (1H, dd, J=2.7, 8.1), 6.88 (1H, d, J=9.0), 7.06 (1H, d, J=8.1), 7.80 (1H, brs), 8.04 (1H, dd, J=2.7, 9.0), 8.16 (1H, d, J=2.7). |
| 8 | not less than 97 | 146–148 | | |
| 9 | 95 | 121–123 | IR: | 3310 ($\nu_{NH}$), 1643 ($\nu_{c=o}$). |
| 10 | 89 | 117–120 | IR: | 3350 ($\nu_{NH}$), 1667 ($\nu_{c=o}$). |
| 11 | 94 | 142–144 | NMR: | 3.04 (6H, s), 3.18 (2H, t, J=7.2), 4.60 (2H, t, J=7.2), 6.32 (1H, s), 6.50 (2H, m), 6.94 (2H, d, J=9.0), 7.10 (1H, dd, J=2.7, 7.2), 7.36 (2H, d, J=9.0). |
| 12 | 91 | 124–126 | NMR: | 3.14 (2H, t, J=7.2), 3.20 (3H, s), 3.78 (3H, s), 4.60 (2H, t, J=7.2), 6.44 (2H, m), 6.98 (2H, d, J=9.0), 7.18 (1H, dd, J=2.7, 7.2), 7.42 (2H, d, J=9.0), 7.86 (1H, s). |
| 13 | not less than 97 | 143.5–145 | IR:<br>NMR: | 3310 ($\nu_{NH}$), 1642 ($\nu_{c=o}$).<br>0.96 (3H, t, J=7.2), 1.69 (2H, q, J=7.2), 3.02 (6H, s), 3.31 (1H, m), 4.24 (1H, t, J=9.0), 4.65 (1H, t, J=9.0), 6.32–7.48 (8H, m). |
| 14 | not less than 97 | liquid | IR: | 3330 ($\nu_{NH}$), 1676 ($\nu_{c=o}$). |
| 15 | not less than 97 | 129–129.9 | IR: | 3290 ($\nu_{NH}$), 1635 ($\nu_{c=o}$). |
| 16 | 85 | 58–59.0 | IR: | 3310 ($\nu_{NH}$), 1660 ($\nu_{c=o}$). |
| 17 | 53 | 198–199.5 | | |
| 18 | not less than 97 | 101–103 | | |
| 19 | not less than 97 | 152–153 | NMR: | 1.48 (3H, d, J=7.2), 2.76 (1H, dd, J=8.0, 15.0), 2.85 (3H, d, J=5.4), 3.28 (1H, dd, J=8.0, 15.0), 4.94 (1H, m), 6.44 (2H, m), 6.94 (2H, d, J=9.0), 7.08 (1H, d, J=8.0), 7.24 (2H, d, J=9.0). |
| 20 | not less than 97 | 124–128 | NMR: | 1.47 (3H, d, J=7.2), 2.74 (1H, dd, J=8.0, 15.0), 3.06 (6H, s), 3.30 (1H, dd, J=8.0, 15.0), 4.94 (1H, m), 6.40 (2H, m), 6.94 (2H, d, J=9.0), 7.06 (1H, d, J=8.0), 7.36 (2H, d, J=9.0). |
| 21 | 64 | 75–76 | NMR: | 1.48 (3H, d, J=7.2), 2.75 (1H, dd, J=8.0, 15.0), 3.24 (3H, s), 3.30 (1H, dd, J=8.0, 15.0), 3.80 (3H, s), 4.94 (1H, m), 6.40 (2H, m), 6.98 (2H, d, J=9.0), 7.06 (1H, d, J=8.0), 7.42 (2H, d, J=9.0). |
| 22 | not less than 97 | 138–140 | NMR: | 1.04 (3H, t, J=7.2), 1.76 (2H, m), 2.82 (1H, dd, J=8.0, 15.0), 2.88 (3H, d, J=5.4), 3.26 (1H, dd, J=8.0, 15.0), 4.74 (1H, m), 6.46 (2H, m), 6.98 (2H, d, J=9.0), 7.08 (1H, d, J=8.0), 7.26 (2H, d, J=9.0). |
| 23 | not less than 97 | 132–136 | NMR: | 1.04 (3H, t, J=7.2), 1.80 (2H, m), 2.82 (1H, dd, J=8.0, 15.0), 3.08 (6H, s), 3.24 (1H, dd, J=8.0, 15.0), 4.72 (1H, m), 6.40 (2H, m), 6.94 (2H, d, J=9.0), 7.06 (1H, d, J=8.0), 7.34 (2H, d, J=9.0). |
| 24 | 75 | 98–100 | NMR: | 1.04 (3H, t, J=7.2), 1.80 (2H, m), 2.80 (1H, dd, J=8.0, 15.0), 3.18 (3H, s), 3.26 (1H, dd, J=8.0, 15.0), 4.70 (1H, m), 6.40 (2H, m), 6.94 (2H, d, J=9.0), 7.06 (1H, d, J=8.0), 7.42 (2H, d, J=9.0). |
| 25 | not less than 97 | 155–156 | NMR: | 0.98 (3H, d, J=7.2), 1.06 (3H, d, J=7.2), 1.92 (1H, m), 2.84 (3H, s), 2.86 (1H, dd, J=8.0, 15.0), 3.16 (1H, dd, J=8.0, 15.0), 4.54 (1H, m), 6.44 (2H, m), 6.94 (2H, d, J=9.0), 7.06 (1H, d, J=8.0), 7.24 (2H, d, J=9.0). |
| 26 | not less than 97 | 148–150 | NMR: | 0.98 (3H, d, J=7.2), 1.06 (3H, d, J=7.2), 1.92 (1H, m), 2.86 (1H, dd, J=8.0, 15.0), 3.14 (1H, dd, J=8.0, 15.0), 3.08 (6H, s), 4.54 (1H, m), 6.42 (2H, m), 6.94 (2H, d, J=9.0), 7.06 (1H, d, J=7.2), 7.34 (2H, d, J=9.0). |
| 27 | 87 | 115.5–116.5 | NMR: | 0.98 (3H, d, J=7.2), 1.06 (3H, d, J=7.2), 1.94 (1H, m), 2.88 (1H, dd, J=8.0, 15.0), 3.18 (1H, dd, J=8.0, 15.0), 3.22 (3H, s), 3.80 (3H, s), 4.54 (1H, m), 6.44 (2H, m), 6.94 (2H, d, J=9.0), 7.06 (1H, d, J=7.2), 7.42 (2H, d, J=9.0). |
| 28 | 94 | 144–145 | NMR: | 0.94 (3H, t, J=7.2), 1.00 (3H, d, J=7.2), 1.70 (3H, m), 2.84 (3H, brs), 2.80–3.20 (2H, m), 4.70 (1H, m), 6.40 (2H, m), 6.94 (2H, d, J=9.0), 7.04 (1H, d, J=8.0), 7.22 (2H, d, J=9.0). |
| 29 | 85 | 142–144 | NMR: | 0.94 (3H, t, J=7.2), 1.00 (3H, d, J=7.2), 1.60 (3H, m), 2.70–3.30 (2H, m), 3.04 (6H, s), 4.64 (1H, m), 6.40 (2H, m), 6.94 (2H, d, J=9.0), 7.06 (1H, d, J=8.0), 7.14 (2H, d, J=9.0). |
| 30 | 79 | 89–90 | NMR: | 0.94 (3H, t, J=7.2), 1.00 (3H, d, J=7.2), 1.70 (3H, m), 2.80–3.20 (2H, m), 3.20 (3H, s), 3.78 (3H, s), 4.64 (1H, m), 6.40 (2H, m), 6.94 (2H, d, J=9.0), |

TABLE 13-continued

| Compound No. | Yield (%) | Melting point (°C.) | Spectral data | |
|---|---|---|---|---|
| | | | | 7.04 (1H, d, J=8.0), 7.42 (2H, d, J=9.0). |
| 31 | 90 | 139–140 | IR: | 3310 ($\nu_{NH}$), 1634 ($\nu_{c=o}$). |
| 32 | 86 | 162.5–163 | IR: | 3290 ($\nu_{NH}$), 1636 ($\nu_{c=o}$). |
| 33 | 90 | 118–119 | IR: | 3340 ($\nu_{NH}$), 1665 ($\nu_{c=o}$). |
| 34 | 63 | liquid | NMR: | 0.95 (3H, t, J=7.0), 1.41 (3H, s), 1.70 (2H, q, J=7.0), 2.76 (3H, d, J=5.0), 2.94 (2H, d, J=6.0), 5.62 (1H, d, J=6.0), 6.34–6.50 (2H, m), 6.80–7.10 (3H, m), 7.16–7.36 (2H, m), 7.52 (1H, brs). |
| 35 | 71 | liquid | NMR: | 0.94 (3H, t, J=7.0), 1.40 (3H, s), 1.72 (2H, q, J=7.0), 2.94 (2H, s), 3.00 (6H, s), 6.34–6.48 (2H, m), 6.86–7.60 (4H, m), 7.22–7.40 (2H, m). |
| 36 | 85 | liquid | NMR: | 0.94 (3H, t, J=7.0), 1.41 (3H, s), 1.72 (2H, q, J=7.0), 2.92 (2H, d, J=6.0), 3.16 (3H, s), 3.74 (3H, s), 6.36–6.50 (2H, m), 6.90–7.10 (3H, m), 7.26–7.50 (2H, m), 7.70 (1H, brs). |
| 37 | 85 | 78–81 | NMR: | 0.90 (6H, t, J=7.0), 1.68 (4H, q, J=7.0), 2.76 (3H, d, J=5.0), 2.91 (2H, s), 5.36 (1H, brs), 6.24–6.44 (2H, m), 6.80–7.05 (3H, m), 7.10–7.30 (2H, m). |
| 38 | 65 | liquid | NMR: | 0.90 (6H, t, J=7.0), 1.68 (4H, q, J=7.0), 2.95 (2H, s), 2.98 (6H, s), 6.30–6.50 (3H, m), 6.88–7.04 (3H, m), 7.20–7.36 (2H, m). |
| 39 | 65 | liquid | NMR: | 0.90 (6H, t, J=7.0), 1.70 (4H, q, J=7.0), 2.90 (2H, s), 3.16 (3H, s), 3.72 (3H, s), 6.30–6.44 (2H, m), 6.88–7.04 (3H, m), 7.34–7.46 (2H, m), 7.65 (1H, brs). |
| 40 | not less than 97 | 118.5–119.5 | | |
| 41 | not less than 97 | liquid | NMR: | 0.90 (3H, t, J=7.2), 1.13 (3H, d, J=6.3), 1.16 (3H, s), 1.68 (2H, q, J=7.2), 2.89 (6H, s), 3.08 (1H, q, J=6.3), 6.28–7.08 (4H, m), 7.50–8.04 (3H, m). |
| 42 | not less than 97 | liquid | NMR: | 1.00 (3H, t, J=7.2), 1.23 (3H, d, J=6.3), 1.26 (3H, s), 1.79 (2H, q, J=7.2), 3.20 (3H, s), 3.23 (1H, q, J=6.3), 3.78 (3H, s), 6.40–7.12 (4H, m), 7.50–8.20 (3H, m). |
| 43 | 86 | 81–86 | NMR: | 0.98 (3H, t, J=7.2), 1.20 (3H, d, J=6.3), 1.24 (3H, s), 1.75 (2H, q, J=7.2), 3.02 (6H, s), 3.10 (1H, q, J=6.3), 6.37 (1H, d, J=2.7), 6.42 (1H, d, J=2.7, 9.0), 6.94 (2H, d, J=9.0), 6.98 (1H, d, J=9.0), 7.30 (2H, d, J=9.0). |
| 44 | 91 | 75–76.5 | | |
| 45 | 88 | 59.5–60.5 | | |
| 46 | 64 | 129–130 | NMR: | 0.99 (3H, t, J=7.2), 1.22 (3H, d, J=6.3), 1.25 (3H, s), 1.78 (2H, q, J=7.2), 3.03 (6H, s), 3.18 (1H, q, J=6.3), 6.33 (1H, d, J=2.7), 6.38 (1H, dd, J=2.7, 9.0), 6.62 (1H, brs), 6.94 (1H, d, J=9.0), 6.97 (1H, d, J=9.0), 7.24 (1H, dd, J=2.7, 9.0), 7.58 (1H, d, J=2.7). |
| 47 | 93 | liquid | NMR: | 1.00 (3H, t, J=7.2), 1.23 (3H, d, J=6.3), 1.26 (3H, s), 1.78 (2H, q, J=7.2), 3.18 (1H, q, J=6.3), 3.20 (3H, s), 3.78 (3H, s), 6.33 (1H, d, J=2.7), 6.39 (1H, dd, J=2.7, 9.0), 6.99 (2H, d, J=9.0), 7.32 (1H, dd, J=2.7, 9.0), 7.69 (1H, d, J=2.7), 7.77 (1H, brs). |
| 48 | 59 | 118.5–119.5 | IR: | 3320 ($\nu_{NH}$), 1642 ($\nu_{c=o}$), 1520 ($\nu_{NO2}$), 1343 ($\nu_{NO2}$). |
| 49 | 60 | 114–115.5 | IR: | 3410 ($\nu_{NH}$), 3305 ($\nu_{NH}$), 1648 ($\nu_{c=o}$), 1525 ($\nu_{NO2}$), 1345 ($\nu_{NO2}$). |
| 50 | 70 | liquid | IR: | 3380 ($\nu_{NH}$), 1670 ($\nu_{c=o}$), 1525 ($\nu_{NO2}$), 1345 ($\nu_{NO2}$). |
| 51 | 92 | 77–79 | | |
| 52 | 80 | 50–51 | | |
| 53 | not less than 97 | liquid | NMR: | 0.99 (3H, t, J=7.2), 1.22 (3H, d, J=6.3), 1.26 (3H, s), 1.78 (2H, q, J=7.2), 3.19 (1H, q, J=6.3), 3.21 (3H, s), 3.78 (3H, s), 6.41 (1H, d, J=2.7), 6.45 (1H, dd, J=2.7, 9.0), 6.98 (1H, d J=9.0), 7.01 (1H, d, J=8.1), 7.64 (1H, dd, J=2.7, 8.1), 7.76 (1H, d, J=2.7), 7.80 (1H, brs). |
| 54 | not less than 97 | 112–113 | | |
| 55 | not less than 97 | 125.5–126 | IR: | 3310 ($\nu_{NH}$), 1643 ($\nu_{c=o}$). |
| 56 | 80 | 107–108.5 | IR: | 3340 ($\nu_{NH}$), 1660 ($\nu_{c=o}$). |
| 57 | 84 | 111.5–112 | IR: | 3310 ($\nu_{NH}$), 1650 ($\nu_{c=o}$). |
| 58 | not less than 97 | liquid | IR: | 3320 ($\nu_{NH}$), 1674 ($\nu_{c=o}$). |
| 59 | 94 | 141–142.5 | NMR: | 1.48 (3H, d J=6.3), 2.80–3.40 (2H, m), 3.03 (6H, s), 4.90 (1H, m), 6.40–6.98 (4H, m), 7.80–8.04 (2H, m). |
| 60 | 65 | 108–110 | NMR: | 1.48 (3H, d, J=6.3), 2.82 (1H, dd, J=8.1, 9.0), 3.10 (3H, s), 3.78 (3H, s), 4.96 (1H, m), 6.72–7.00 (4H, m), 7.70 (1H, brs), 7.93 (1H, dd, J=3.6, 8.1), 8.12 (1H, d, J=3.6). |
| 61 | 84 | 159–161 | IR: | 3305 ($\nu_{NH}$), 1640 ($\nu_{c=o}$). |
| 62 | not less than 97 | 128–129 | IR: | 3305 ($\nu_{NH}$), 1660 ($\nu_{c=o}$). |
| 63 | 82 | 120–122 | NMR: | 1.28 (3H, d, J=6.9), 3.02 (6H, s), 3.52 (1H, m), 4.10 (1H, t, J=9.0), 4.70 (1H, t, J=9.0), 6.44 (1H, |

TABLE 13-continued

| Compound No. | Yield (%) | Melting point (°C.) | Spectral data | |
|---|---|---|---|---|
| | | | | brs), 6.70–7.46 (7H, m). |
| 64 | 94 | 80–82 | NMR: | 1.29 (3H, d, J=6.9), 3.19 (3H, s), 3.32–3.72 (1H, m), 3.76 (3H, s), 4.09 (1H, t, J=9.0), 4.70 (1H, t, J=9.0), 6.68–7.52 (7H, m), 7.73 (1H, brs). |
| 65 | 95 | liquid | IR: | 3325 ($\nu_{NH}$), 1645 ($\nu_{c=o}$). |
| | | | NMR: | 0.92 (3H, t, J=7.2), 1.66 (2H, q, J=7.2), 3.00 (6H, s), 3.32 (1H, m), 4.21 (1H, dd, J=7.2, 9.0), 4.63 (1H, t, J=9.0), 6.36 (1H, brs), 6.60–7.40 (7H, m). |
| 66 | 85 | liquid | IR: | 3325 ($\nu_{NH}$), 1675 ($\nu_{c=o}$). |
| | | | NMR: | 0.96 (3H, t, J=7.2), 1.68 (2H, q, J=7.2), 3.20 (3H, s), 3.26 (1H, m), 3.78 (3H, s), 4.21 (1H, dd, J=7.2, 9.0), 4.65 (1H, t, J=9.0), 6.68–7.32 (7H, m), 7.63 (1H, brs). |
| 67 | not less than 97 | liquid | IR: | 3320 ($\nu_{NH}$), 1645 ($\nu_{c=o}$). |
| | | | NMR: | 0.94 (3H, t, J=7.2), 1.24–1.76 (4H, m), 3.00 (6H, s), 3.06 (1H, m), 4.20 (1H, dd, J=7.2, 9.0), 4.64 (1H, t, J=9.0), 6.40 (1H, brs), 6.64–7.40 (7H, m). |
| 68 | 92 | liquid | IR: | 3325 ($\nu_{NH}$), 1675 ($\nu_{c=o}$). |
| | | | NMR: | 0.94 (3H, t, J=7.2), 1.28–1.80 (4H, m), 3.18 (3H, s), 3.20 (1H, m), 3.76 (3H, s), 4.20 (1H, dd, J=7.2, 9.0), 4.65 (1H, d, J=9.0), 6.64–7.50 (7H, m), 7.63 (1H, brs). |
| 69 | not less than 97 | liquid | NMR: | 0.82 (3H, d, J=6.4), 0.90 (3H, d, J=6.4), 1.70–2.10 (1H, m), 2.70 (3H, d, J=3.9), 3.12–3.40 (1H, m), 4.20–4.66 (2H, m), 6.00 (1H, brs), 6.60–7.30 (7H, m), 7.92 (1H, brs). |
| 70 | 92 | 124–125 | NMR: | 0.86 (3H, d, J=6.4), 0.94 (3H, d, J=6.4), 1.74–2.08 (1H, m), 3.00 (6H, s), 3.16–3.42 (1H, m), 4.30–4.68 (2H, m), 6.48 (1H, brs), 6.66–7.40 (7H, m). |
| 71 | not less than 97 | liquid | NMR: | 0.84 (3H, d, J=6.4), 0.92 (3H, d, J=6.4), 1.74–2.10 (1H, m), 3.16 (3H, s), 3.12–3.42 (1H, m), 4.30–4.66 (2H, m), 6.68–7.50 (7H, m), 7.72 (1H, brs). |
| 72 | 69 | 196–198 | IR: | 3325 ($\nu_{NH}$), 1639 ($\nu_{c=o}$). |
| 73 | 88 | 146–148 | NMR: | 0.98 (3H, d, J=6.4), 1.00 (3H, d, J=6.4), 1.40–2.06 (3H, m), 2.65–3.32 (2H, m), 3.04 (6H, s), 4.72–4.96 (1H, m), 6.24 (1H, brs), 6.60–7.36 (7H, m). |
| 74 | 65 | 112–114 | NMR: | 0.98 (3H, d, J=6.4), 1.02 (3H, d, J=6.4), 1.48–2.00 (3H, m), 2.66–3.32 (2H, m), 3.20 (3H, s), 3.80 (3H, s), 4.72–5.00 (1H, m), 6.70–7.50 (7H, m), 7.62 (1H, brs). |
| 75 | 87 | liquid | NMR: | 0.95 (3H, t, J=7.2), 1.20–1.86 (2H, m), 2.70 (3H, d, J=4.5), 2.90–3.20 (1H, m), 3.52 (3H, s), 5.26 (1H, d, J=2.7), 5.96 (1H, brs), 6.60–7.32 (7H, m), 7.91 (1H, brs). |
| 76 | 90 | liquid | NMR: | 0.96 (3H, t, J=7.2), 1.30–1.90 (2H, m), 2.90–3.20 (1H, m), 2.98 (6H, s), 3.53 (3H, s), 5.26 (1H, d, J=2.7), 6.63 (1H, brs), 6.70–7.40 (7H, m). |
| 77 | 92 | liquid | NMR: | 0.96 (3H, t, J=7.2), 1.30–1.90 (2H, m), 2.90–3.20 (1H, m), 3.17 (3H, s), 3.52 (3H, s), 3.73 (3H, s), 5.26 (1H, d, J=2.7), 6.68–7.52 (7H, m), 7.73 (1H, brs). |
| 78 | 80 | 149–151 | IR: | 3290, 3275 ($\nu_{NH}$), 1643 ($\nu_{c=o}$). |
| 79 | not less than 97 | 104–106 | IR: | 3270 ($\nu_{NH}$), 1652 ($\nu_{c=o}$). |
| 80 | 90 | 145–146 | IR: | 3305 ($\nu_{NH}$), 1632 ($\nu_{c=o}$). |
| 81 | 80 | 131–133 | IR: | 3315 ($\nu_{NH}$), 1642 ($\nu_{c=o}$). |
| 82 | not less than 97 | 82–85 | IR: | 3340 ($\nu_{NH}$), 1664 ($\nu_{c=o}$). |
| 83 | 80 | 152–153 | IR: | 3280 ($\nu_{NH}$), 1636 ($\nu_{c=o}$). |
| 84 | not less than 97 | liquid | IR: | 3320 ($\nu_{NH}$), 1675 ($\nu_{c=o}$). |
| 85 | 92 | 154–155 | IR: | 3340 ($\nu_{NH}$), 1640 ($\nu_{c=o}$). |
| 86 | not less than 97 | 95–96.5 | IR: | 3370 ($\nu_{NH}$), 1675 ($\nu_{c=o}$). |
| 87 | not less than 97 | 191.5–193 | IR: | 3350 ($\nu_{NH}$), 3290 ($\nu_{NH}$), 1636 ($\nu_{c=o}$). |
| 88 | 75 | 115–116 | IR: | 3260 ($\nu_{NH}$), 1635 ($\nu_{c=o}$). |
| 89 | 83 | 99.5–101 | IR: | 3360 ($\nu_{NH}$), 1664 ($\nu_{c=o}$). |
| 90 | 95 | 97–99 | IR: | 3290 ($\nu_{NH}$), 1640 ($\nu_{c=o}$). |
| 91 | not less than 97 | liquid | NMR: | 1.24 (3H, t, J=6.4), 1.26 (3H, d, J=6.4), 3.18 (3H, s), 3.50–4.25 (3H, m), 3.74 (3H, s), 5.32 (1H, d, J=2.6), 6.70–6.90 (3H, m), 6.90 (2H, d, J=9.0), 7.39 (2H, d, J=9.0), 7.70 (1H, brs). |
| 92 | 81 | 175–178 | NMR: | 1.27 (3H, s), 1.29 (3H, s), 3.05 (6H, s), 3.56 (3H, s), 5.14 (1H, s), 6.34 (1H, brs), 6.70–6.93 (3H, m), 7.85–8.08 (3H, m). |
| 93 | 82 | liquid | NMR: | 1.27 (3H, s), 1.29 (3H, s), 3.20 (3H, s), 3.65 (3H, s), 3.79 (3H, s), 5.14 (1H, s), 6.70–7.00 (4H, m), 7.62 (1H, brs), 8.02 (1H, dd, J=2.7, 9.0), 8.13 (1H, d, J=2.7). |
| 94 | not less than 97 | 156–157 | | |
| 95 | 81 | 52–54 | NMR: | 1.25 (3H, s), 1.28 (3H, s), 3.04 (6H, s), 3.55 (3H, |

TABLE 13-continued

| Compound No. | Yield (%) | Melting point (°C.) | Spectral data | |
|---|---|---|---|---|
| | | | | s), 5.12 (1H, s), 6.34 (1H, brs), 6.70–7.04 (3H, m), 6.91 (2H, d, J=9.0), 7.32 (2H, d, J=9.0). |
| 96 | not less than 97 | liquid | NMR: | 1.25 (3H, s), 1.28 (3H, s), 3.19 (3H, s), 3.55 (3H, s), 3.77 (3H, s), 6.70–7.04 (3H, m), 6.94 (2H, d, J=9.0), 7.42 (2H, d, J=9.0), 7.68 (1H, brs). |
| 97 | 63 | 165–168 | NMR: | 1.24 (3H, s), 1.28 (3H, s), 3.02 (6H, s), 3.54 (3H, s), 5.10 (1H, s), 6.32 (1H, brs), 6.74 (3H, brs), 6.82 (1H, d, J=9.0), 7.18 (1H, dd, J=2.7, 9.0), 7.55 (1H, d, J=2.7). |
| 98 | 69 | 96–99 | NMR: | 1.25 (3H, s), 1.28 (3H, s), 3.19 (3H, s), 3.54 (3H, s), 3.76 (3H, s), 5.11 (1H, s), 6.75 (3H, brs), 6.85 (1H, d, J=9.0), 7.34 (1H, dd, J=2.7, 9.0), 7.63 (1H, d, J=2.7). |
| 99 | 92 | 149–150 | NMR: | 0.60–1.06 (6H, m), 1.40–1.90 (2H, m), 2.78 (3H, s), 3.56 (3H, s), 5.15 (1H, s), 6.64–7.36 (8H, m). |
| 100 | 70 | 122–124 | NMR: | 0.64–1.04 (6H, m), 1.44–1.86 (2H, m), 3.05 (6H, s), 3.55 (3H, s), 5.14 (1H, s), 6.24 (1H, brs), 6.68–7.40 (7H, m). |
| 101 | not less than 97 | 97–98 | NMR: | 0.60–1.10 (6H, m), 1.44–1.92 (2H, m), 3.17 (3H, s), 3.54 (3H, s), 3.73 (3H, s), 5.13 (1H, s), 6.76 (3H, m), 6.90 (2H, d, J=9.0), 7.40 (2H, d, J=9.0), 7.76 (1H, brs). |
| 102 | 93 | 145.5–147 | NMR: | 0.77 (3H, t, J=7.5), 0.90 (3H, t, J=7.5), 1.44–1.92 (4H, m), 2.76 (3H, s), 3.56 (3H, s), 5.14 (1H, s), 6.68–7.36 (9H, m). |
| 103 | 93 | 117–118 | | |
| 104 | 89 | liquid | NMR: | 0.78 (3H, t, J=7.1), 0.92 (3H, t, J=7.1), 1.42–1.96 (4H, m), 3.18 (3H, s), 3.56 (3H, s), 3.76 (3H, s), 5.14 (1H, s), 6.78 (3H, m), 6.90 (2H, d, J=9.0), 7.40 (2H, d, J=9.0), 7.68 (1H, brs). |
| 105 | not less than 97 | liquid | NMR: | 0.88 (3H, d, J=6.4), 0.92 (3H, d, J=6.4), 1.72–2.08 (1H, m), 2.99 (6H, s), 3.52 (3H, s), 5.32 (1H, d, J=2.1), 6.55 (1H, brs), 6.70–7.40 (7H, m). |
| 106 | not less than 97 | 93–94 | NMR: | 0.90 (3H, d, J=6.4), 0.93 (3H, d, J=6.4), 1.80–2.08 (1H, m), 2.96–3.16 (1H, m), 3.19 (3H, s), 3.54 (3H, s), 3.76 (3H, s), 5.32 (1H, d, J=2.1), 6.70–7.50 (7H, m), 7.64 (1H, brs). |
| 107 | not less than 97 | liquid | IR: NMR: | 3325 ($\nu_{NH}$), 1640 ($\nu_{c=o}$).<br>0.96 (3H, t, J=7.7), 1.23 (3H, t, J=7.1), 1.40–1.84 (2H, m), 3.00 (6H, s), 3.01–3.16 (1H, m), 3.52–4.00 (2H, m), 5.38 (1H, d, J=2.1), 6.47 (1H, brs), 6.70–7.44 (7H, m). |
| 108 | not less than 97 | liquid | IR: NMR: | 3325 ($\nu_{NH}$), 1675 ($\nu_{c=o}$).<br>0.97 (3H, t, J=7.2), 1.25 (3H, t, J=7.2), 1.63 (2H, q, J=7.2), 3.13 (1H, m), 3.18 (3H, s), 3.76 (3H, s), 3.50–4.16 (2H, m), 5.38 (1H, d, J=2.7), 6.68–6.90 (3H, m), 6.90 (2H, d, J=9.0), 7.39 (2H, d, J=9.0), 7.69 (1H, brs). |
| 109 | 86 | liquid | NMR: | 0.92 (3H, d, J=6.4), 0.96 (3H, d, J=6.4), 1.26 (3H, t, J=6.4), 1.72–2.16 (1H, m), 2.78 (3H, d, J=5.1), 3.04 (1H, dd, J=1.5, 5.1), 3.54–4.12 (2H, m), 5.28 (1H, d, J=5.1), 5.44 (1H, d, J=1.5), 6.70–7.50 (8H, m). |
| 110 | 72 | liquid | NMR: | 0.88 (3H, d, J=6.4), 0.92 (3H, d, J=6.4), 1.24 (3H, t, J=7.1), 1.80–2.12 (1H, m), 3.00 (6H, s), 3.02–3.12 (1H, m), 3.52–4.06 (2H, m), 5.44 (1H, d, J=1.5), 6.40 (1H, brs), 6.72–7.40 (7H, m). |
| 111 | 80 | liquid | NMR: | 0.90 (3H, d, J=6.4), 0.92 (3H, d, J=6.4), 1.26 (3H, t, J=7.1), 1.68–2.10 (1H, m), 3.04 (1H, m), 3.20 (3H, s), 3.50–4.08 (2H, m), 3.77 (3H, s), 5.44 (1H, d, J=1.5), 6.72–7.04 (5H, m), 7.40 (2H, d, J=9.0), 7.65 (1H, brs). |
| 112 | 73 | 149–151.5 | IR: | 3285 ($\nu_{NH}$), 1643 ($\nu_{c=o}$). |
| 113 | 95 | 62–65 | IR: | 3310 ($\nu_{NH}$), 1660 ($\nu_{c=o}$). |
| 114 | 72 | 133–134 | IR: | 3280 ($\nu_{NH}$), 1638 ($\nu_{c=o}$). |
| 115 | not less than 97 | 77–79 | IR: | 3310 ($\nu_{NH}$), 1659 ($\nu_{c=o}$). |
| 116 | 80 | 145–147 | IR: | 3355 ($\nu_{NH}$), 3305 ($\nu_{NH}$), 1650 ($\nu_{c=o}$). |
| 117 | 77 | 157–158 | NMR: | 1.30–2.16 (8H, m), 3.12 (6H, s), 3.13–3.36 (1H, m), 4.64–4.88 (1H, m), 6.32 (1H, brs), 6.76–7.48 (7H, m). |
| 118 | 73 | 118–120 | NMR: | 1.20–2.10 (8H, m), 3.00–3.30 (1H, m), 3.20 (3H, s), 3.78 (3H, s), 4.52–4.80 (1H, m), 6.68–7.52 (7H, m), 7.63 (1H, brs). |
| 119 | 73 | 137.5–139 | IR: | 3325 ($\nu_{NH}$), 1645 ($\nu_{c=o}$). |
| 120 | 79 | 164–165 | NMR: | 1.00–2.10 (10H, m), 3.05 (6H, s), 3.40–3.62 (1H, m), 4.30–4.60 (1H, m), 6.25 (1H, brs), 6.64–7.44 (7H, m). |
| 121 | not less than 97 | 127–128 | NMR: | 0.96–2.10 (10H, m), 3.19 (3H, s), 3.30–3.60 (1H, m), 3.76 (3H, s), 4.00–4.56 (1H, m), 6.70–7.52 (7H, m), 7.68 (1H, brs). |
| 122 | 92 | 57–59 | NMR: | 0.80–2.10 (10H, m), 2.76 (3H, d, J=3.9), 3.36–3.70 (1H, m), 4.48–4.96 (1H, m), 5.66 (1H, d, J=2.9), |

TABLE 13-continued

| Compound No. | Yield (%) | Melting point (°C.) | Spectral data | |
|---|---|---|---|---|
| | | | | 6.50–7.34 (7H, m), 7.52 (1H, s). |
| 123 | 79 | 56–58 | IR: | 3325 ($\nu_{NH}$), 1650 ($\nu_{c=o}$). |
| 124 | 60 | liquid | NMR: | 0.80–2.10 (10H, m), 3.20 (3H, s), 3.40–3.70 (1H, m), 3.78 (3H, s), 4.48–4.96 (1H, m), 6.68–7.52 (7H, m), 7.70 (1H, brs). |
| 125 | 90 | 176–178 | | |
| 126 | 84 | 138.5–140 | NMR: | 3.02 (6H, s), 5.95 (2H, s), 6.43 (1H, dd, J=2.7, 9.0), 6.45 (1H, brs), 6.57 (1H, d, J=2.7), 6.74 (1H, d, J=9.0), 6.90 (2H, d, J=9.0), 7.32 (1H, d, J=9.0). |
| 127 | not less than 97 | 90–91 | NMR: | 3.09 (3H, s), 3.77 (3H, s), 5.96 (2H, s), 6.36 (1H, dd, J=2.7, 9.0), 6.57 (1H, d, J=2.7), 6.76 (1H, d, J=9.0), 6.84 (2H, d, J=9.0), 7.42 (2H, d, J=9.0), 7.64 (1H, brs). |
| 128 | 89 | 150–151 | | |
| 129 | 81 | 125–126 | NMR: | 1.01 (3H, t, J=7.2), 1.61 (3H, s), 1.95 (2H, q, J=7.2), 3.02 (6H, s), 6.38 (1H, dd, J=2.7, 8.1), 6.47 (1H, d, J=2.7), 6.64 (1H, d, J=8.1), 6.90 (2H, d, J=9.0), 7.30 (2H, d, J=9.0). |
| 130 | 88 | 99.5–101 | NMR: | 1.02 (3H, t, J=7.2), 1.62 (3H, s), 1.95 (2H, q, J=7.2), 3.18 (3H, s), 3.76 (3H, s), 6.38 (1H, dd, J=2.7, 8.1), 6.47 (1H, d, J=2.7), 6.63 (1H, d, J=8.1), 6.93 (2H, d, J=9.0), 7.39 (2H, d, J=9.0), 7.65 (1H, brs). |
| 131 | 56 | 169–170 | IR: | 3285 ($\nu_{NH}$), 1642 ($\nu_{c=o}$). |
| 132 | 86 | 112–113 | IR: | 3330 ($\nu_{NH}$), 1665 ($\nu_{c=o}$). |
| 133 | 76 | 145–147 | NMR: | 1.67 (6H, s), 3.02 (6H, s), 6.20–6.80 (3H, m), 6.89 (2H, d, J=9.0), 7.29 (2H, d, J=(2H, d, J= |
| | | | IR: | 3295 ($\nu_{NH}$), 1637 ($\nu_{c=o}$). |
| 134 | 90 | 93–94 | IR: | 3350 ($\nu_{NH}$), 1662 ($\nu_{c=o}$). |
| 135 | 72 | 103.5–104.5 | | |
| 136 | not less than 97 | 141–143 | NMR: | 1.80 (3H, s), 3.03 (6H, s), 3.33 (3H, s), 6.45 (1H, dd, J=2.7, 7.2), 6.56 (1H, d, J=2.7), 6.72 (1H, d, J=7.2), 6.73 (2H, d, J=9.0), 7.31 (2H, d, J=9.0). |
| 137 | 94 | 117–118 | NMR: | 1.81 (3H, s), 3.20 (3H, s), 3.74 (3H, s), 3.78 (3H, s), 6.46 (1H, dd, J=2.7, 7.2), 6.56 (1H, d, J=2.7), 6.75 (1H, d, J=7.2), 6.93 (2H, d, J=9.0), 7.42 (2H, d, J=9.0), 7.67 (1H, brs). |
| 138 | not less than 97 | 119–120 | IR: | 3300 ($\nu_{NH}$), 1640 ($\nu_{c=o}$). |
| 139 | not less than 97 | liquid | IR: | 3320 ($\nu_{NH}$), 1675 ($\nu_{c=o}$). |
| 140 | 92 | liquid | NMR: | 1.02 (3H, t, J=7.2), 1.21 (3H, t, J=7.2), 2.06 (2H, q, J=7.2), 3.03 (6H, s), 3.61 (2H, q, J=7.2), 6.20–6.80 (3H, m), 6.91 (2H, d, J=9.0), 7.30 (3H, d, J=9.0). |
| 141 | not less than 97 | liquid | NMR: | 1.21 (3H, t, J=7.2), 1.27 (3H, t, J=7.2), 2.07 (2H, q, J=7.2), 3.19 (3H, s), 3.62 (2H, q, J=7.2), 3.77 (3H, s), 6.32–6.88 (3H, m), 6.93 (2H, d, J=9.0), 7.40 (2H, d, J=9.0), 7.66 (1H, brs). |
| 142 | 83 | 103–104 | IR: | 3300 ($\nu_{NH}$), 1635 ($\nu_{c=o}$). |
| 143 | not less than 97 | liquid | IR: | 3390 ($\nu_{NH}$), 3300 ($\nu_{NH}$), 1668 ($\nu_{c=o}$). |
| 144 | 80 | 113–114 | IR: | 3275 ($\nu_{NH}$), 1633 ($\nu_{c=o}$). |
| 145 | not less than 97 | liquid | IR: | 3390 ($\nu_{NH}$), 3300 ($\nu_{NH}$), 1668 ($\nu_{c=o}$). |
| 146 | 83 | 165–166.5 | IR: | 3300 ($\nu_{NH}$), 1627 ($\nu_{c=o}$). |
| 147 | 85 | 129.5–131 | IR: | 3290 ($\nu_{NH}$), 1635 ($\nu_{c=o}$). |
| 148 | 87 | 105–106 | IR: | 3350 ($\nu_{NH}$), 1668 ($\nu_{c=o}$). |
| 149 | 81 | 151–152 | IR: | 3300 ($\nu_{NH}$), 1627 ($\nu_{c=o}$). |
| 150 | 70 | 112.5–114 | IR: | 3290 ($\nu_{NH}$), 1634 ($\nu_{c=o}$). |
| 151 | 86 | liquid | IR: | 3350 ($\nu_{NH}$), 1665 ($\nu_{c=o}$). |
| 152 | 88 | 164.5–168 | IR: | 3400 ($\nu_{NH}$), 3290 ($\nu_{NH}$), 1650 ($\nu_{c=o}$). |
| 153 | 85 | 192–193.5 | IR: | 3290 ($\nu_{NH}$), 1637 ($\nu_{c=o}$). |
| 154 | 81 | 131.5–134 | IR: | 3325 ($\nu_{NH}$), 1662 ($\nu_{c=o}$). |
| 155 | 71 | 176–177.5 | IR: | 3340 ($\nu_{NH}$), 1635 ($\nu_{c=o}$). |
| 156 | not less than 95 | 109–110 | IR: | 3290 ($\nu_{NH}$), 1657 ($\nu_{c=o}$). |
| 157 | 78 | 162.5–164 | IR: | 3250 ($\nu_{NH}$), 1635 ($\nu_{c=o}$). |
| 158 | 85 | 102–104 | IR: | 3280 ($\nu_{NH}$), 1660 ($\nu_{c=o}$). |
| 159 | 76 | 162–168.5 | IR: | 3330 ($\nu_{NH}$), 1644 ($\nu_{c=o}$). |
| 160 | 92 | 117–118 | IR: | 3330 ($\nu_{NH}$), 1665 ($\nu_{c=o}$). |
| 161 | 84 | 119–122 | NMR: | 1.38 (3H, d, J=7.2), 1.60–2.00 (2H, m), 2.64–2.94 (2H, m), 3.02 (6H, s), 4.00–4.28 (1H, m), 6.40–7.20 (3H, m), 6.85 (1H, d, J=9.0), 7.95 (1H, dd, J=2.7, 9.0), 8.05 (1H, d, J=2.7). |
| 162 | not less than 97 | liquid | NMR: | 1.38 (3H, d, J=7.2), 1.60–2.00 (2H, m), 2.64–3.00 (2H, m), 3.20 (3H, s), 3.79 (3H, s), 4.00–4.16 (1H, m), 6.48–7.20 (3H, m), 6.89 (1H, d, J=9.0), 7.71 (1H, brs), 8.05 (1H, dd, J=2.7, 9.0), 8.16 (1H, d, J=2.7). |
| 163 | 71 | 125.5–126.5 | | |
| 164 | 86 | 114–116 | IR: | 3315 ($\nu_{NH}$), 1640 ($\nu_{c=o}$). |
| 165 | not less | liquid | IR: | 3325 ($\nu_{NH}$), 1680 ($\nu_{c=o}$). |

TABLE 13-continued

| Compound No. | Yield (%) | Melting point (°C.) | Spectral data |
|---|---|---|---|
| 166 | than 97 90 | 148.5–149.5 | IR: 3355 ($\nu_{NH}$), 1646 ($\nu_{c=o}$). |
| 167 | 96 | 118–119 | IR: 3350 ($\nu_{NH}$), 1662 ($\nu_{c=o}$). |
| 168 | not less than 97 | 146–148 | |
| 169 | 82 | 129–131 | NMR: 1.32 (6H, s), 17.78 (2H, t, J=7.2), 2.72 (2H, t, J=7.2), 3.02 (6H, s), 6.33 (1H, brs), 6.39 (1H, d, J=2.7), 6.47 (1H, d, J=9.0), 6.97 (1H, d, J=7.2), 6.96 (2H, d, J=9.0), 7.34 (2.H, d, J=9.0). |
| 170 | 91 | 98–99 | NMR: 1.32 (6H, s), 1.80 (2H, t, J=7.2), 2.75 (2H, t, J=7.2), 3.19 (3H, s), 3.76 (3H, s), 6.52 (1H, d, J=2.7), 6.58 (1H, dd, J=2.7, 7.2), 6.86 (1H, d, J=9.0), 7.04 (1H, d, J=7.2), 7.68 (1H, brs), 8.01 (1H, dd, J=2.7, 9.0), 8.14 (1H, d, J=2.7). |
| 171 | 92 | 131–132 | |
| 173 | 77 | 104–106 | NMR: 1.32 (6H, s), 1.76 (2H, t, J=7.2), 2.73 (2H, t, J=9.0), 3.19 (3H, s), 3.77 (3H, s), 6.39 (1H, d, J=2.7), 6.49 (1H, dd, J=2.7, 9.0), 6.98 (3H, d, J=9.0), 7.42 (2H, d, J=9.0), 7.68 (1H, brs). |
| 174 | 73 | 159–161 | IR: 3275 ($\nu_{NH}$), 1635 ($\nu_{c=o}$). |
| 175 | 70 | 95–97 | NMR: 1.32 (6H, s), 1.78 (2H, t, J=7.2), 2.71 (2H, t, J=7.2), 3.20 (3H, s), 3.78 (3H, s), 6.32 (1H, d, J=2.7), 6.45 (1H, dd, J=2.7, 9.0), 7.01 (2H, d, J=9.0), 7.32 (1H, dd, J=2.7, 9.0), 7.67 (1H, d, J=2.7), 7.72 (1H, brs). |
| 176 | 78 | 133–134 | IR: 3300 ($\nu_{NH}$), 1656 ($\nu_{c=o}$), 1530 ($\nu_{NO2}$), 1370 ($\nu_{NO2}$). |
| 177 | not less than 97 | liquid | IR: 3360 ($\nu_{NH}$), 1660 ($\nu_{c=o}$), 1540 ($\nu_{NO2}$), 1365 ($\nu_{NO2}$). |
| 178 | 96 | 119–121 | IR: 3300 ($\nu_{NH}$), 1640 ($\nu_{c=o}$). |
| 179 | not less than 97 | liquid | IR: 3320 ($\nu_{NH}$), 1675 ($\nu_{c=o}$). |
| 180 | 76 | 69–70 | NMR: 1.29 (3H, s), 1.33 (3H, s), 1.36 (3H, d, J=6.3), 1.62 (1H, s), 1.69 (1H, s), 3.00 (6H, s), 3.06 (1H, brs), 4.20 (1H, q, J=6.3), 6.44–6.72 (2H, m), 6.82 (1H, d, J=9.0), 7.21 (1H, d, J=9.0), 7.90 (1H, dd, J=2.7, 9.0), 8.02 (1H, d, J=2.7). |
| 181 | 95 | 43–45 | NMR: 1.28 (3H, s), 1.30 (3H, s), 1.35 (3H, d, J=6.3), 1.62 (1H, s), 1.69 (1H, s), 3.18 (3H, s), 3.75 (3H, s), 6.51 (1H, d, J=2.7), 6.59 (1H, dd, J=2.7, 8.1), 6.85 (1H, d, J=9.0), 7.22 (1H, d, J=8.1), 7.64 (1H, brs), 8.61 (1H, dd, J=2.7, 9.0), 8.13 (1H, d, J=2.7). |
| 182 | 89 | 164–165 | IR: 3365 ($\nu_{NH}$), 1645 ($\nu_{c=o}$). |
| 183 | 91 | 126–127 | IR: 3330 ($\nu_{NH}$), 1666 ($\nu_{c=o}$). |
| 184 | 88 | 125–126.5 | IR: 3350 ($\nu_{NH}$), 1682 ($\nu_{c=o}$). |
| 185 | not less than 97 | 133–134 | IR: 3335 ($\nu_{NH}$), 1638 ($\nu_{c=o}$). |
| 186 | not less than 97 | 122–123 | IR: 3320 ($\nu_{NH}$), 1660 ($\nu_{c=o}$). |
| 187 | 69 | 129–130 | NMR: 1.32 (3H, s), 1.41 (3H, s), 1.99 (1H, d, J=7.2), 2.03 (1H, d, J=7.2), 3.04 (6H, s), 3.46 (3H, s), 4.39 (1H, t, J=7.2), 6.29 (1H, brs), 6.37 (1H, d, J=2.7), 6.51 (1H, dd, J=2.7, 9.0), 6.97 (2H, d, J=9.0), 7.30 (1H, d, J=9.0), 7.34 (2H, d, J=9.0). |
| 188 | 92 | 96.5–97.5 | NMR: 1.33 (3H, s), 1.42 (3H, s), 1.99 (1, H, d, J=7.2), 2.04 (1H, d, J=7.2), 3.19 (3H, s), 3.46 (3H, s), 3.77 (3H, s), 6.37 (1H, d, J=2.7), 6.55 (1H, dd, J=2.7, 9.0), 6.99 (2H, d, J=9.0), 7.31 (1H, d, J=9.0), 7.42 (2H, d, J=9.0), 7.67 (1H, brs). |
| 189 | not less than 97 | 179–182 | IR: 3320 ($\nu_{NH}$), 1638 ($\nu_{c=o}$). |
| 190 | not less than 97 | 97–98 | |
| 191 | not less than 97 | 70–71 | |
| 192 | not less than 97 | 189–200 | |
| 193 | 67 | 143–145 | NMR: 1.26 (3H, s), 1.41 (3H, s), 1.49 (3H, s), 1.81 (1H, d, J=14.0), 2.03 (1H, d, J=14.0), 3.02 (6H, s), 3.21 (3H, s), 6.29 (1H, brs), 6.43 (1H, d, J=2.7), 6.59 (1H, dd, J=2.7, 9.0), 6.98 (2H, d, J=9.0), 7.21 (1H, d, J=9.0), 7.35 (2H, d, J=9.0). |
| 194 | not less than 97 | 92–93 | NMR: 1.26 (3H, s), 1.42 (3H, s), 1.58 (3H, s), 1.84 (1H, d, J=13.5), 2.05 (1H, d, J=13.5), 3.20 (3H, s), 3.22 (3H, s), 6.45 (1H, d, J=2.7), 6.59 (1H, dd, J=2.7, 9.0), 7.00 (2H, d, J=9.0), 7.20 (1H, d, J=9.0), 7.43 (2H, d, J=9.0), 7.70 (1H, brs). |
| 195 | not less than 97 | 211–212 | |

TABLE 13-continued

| Compound No. | Yield (%) | Melting point (°C.) | Spectral data | |
|---|---|---|---|---|
| 196 | 70 | 164–165 | | |
| 197 | 80 | 92–93.5 | | |
| 198 | 72 | 210–212 | IR: | 3350 ($\nu_{NH}$), 3280 ($\nu_{NH}$), 1644 ($\nu_{C=O}$), 1520 ($\nu_{NO_2}$), 1346 ($\nu_{NO_2}$). |
| 199 | 63 | 163–164 | IR: | 3410 ($\nu_{NH}$), 3320 ($\nu_{NH}$), 1646 ($\nu_{C=O}$), 1524 ($\nu_{NO_2}$), 1350 ($\nu_{NO_2}$). |
| 200 | 86 | 142–144 | IR: | 3260 ($\nu_{NH}$), 1650 ($\nu_{C=O}$), 1525 ($\nu_{NO_2}$), 1340 ($\nu_{NO_2}$). |
| 201 | not less than 97 | 201–202 | | |
| 202 | not less than 97 | 174–175 | | |
| 203 | not less than 97 | 145–174 | | |
| 204 | 69 | 186–188 | NMR: | 1.00 (3H, t, J=7.2), 1.45 (3H, s), 1.50 (3H, s), 1.80 (1H, d, J=14.0), 2.04 (1H, d, J=14.0), 3.03 (6H, s), 3.55 (2H, q, J=7.2), 6.30 (1H, brs), 6.43 (1H, d, J=2.7), 6.58 (1H, dd, J=2.7, 9.0), 6.98 (2H, d, J=9.0), 7.21 (1H, d, J=9.0), 7.34 (2H, d, J=9.0). |
| 205 | not less than 97 | liquid | IR: | 3325 ($\nu_{NH}$), 1675 ($\nu_{C=O}$). |
| 206 | 82 | 153.5–154.5 | | |
| 207 | not less than 97 | liquid | NMR: | 0.72 (3H, t, J=7.2), 1.20–1.60 (2H, m), 1.28 (3H, s), 1.46 (3H, s), 1.52 (3H, s), 1.82 (1H, d, J=13.5), 206 (1H, d, J=13.5), 3.20 (3H, s), 3.47 (3H, t, J=7.2), 3.69 (3H, s), 6.44 (1H, d, J=2.7), 6.60 (1H, dd, J=2.7, 9.0), 6.99 (2H, d, J=9.0), 7.23 (1H, d, J=9.0), 7.43 (2H, d, J=9.0), 7.67 (1H, brs). |
| 208 | not less than 97 | 173–174 | | |
| 209 | 81 | 62–63 | IR: | 3320 ($\nu_{NH}$), 1653 ($\nu_{C=O}$). |
| 210 | not less than 97 | liquid | IR: | 3320 ($\nu_{NH}$), 1673 ($\nu_{C=O}$). |
| 211 | 61 | liquid | NMR: | 1.82–2.20 (2H, m), 3.00 (6H, s), 3.43 (3H, s), 4.10–4.36 (3H, m), 6.34–6.60 (3H, m), 6.82–7.40 (5H, m). |
| 212 | 69 | liquid | NMR: | 1.88–2.20 (2H, m), 3.18 (3H, s), 3.42 (3H, s), 3.74 (3H, s), 4.06–4.34 (3H, m), 6.40–6.60 (2H, m), 6.86–7.50 (5H, m), 7.76 (1H, brs). |
| 213 | 58 | 143–145 | | |
| 214 | not less than 97 | liquid | NMR: | 1.00 (3H, t, J=7.2), 1.40–2.16 (4H, m), 2.50–3.00 (2H, m), 3.18 (3H, s), 3.70–4.04 (1H, m), 3.76 (3H, s), 6.32–7.56 (7H, m), 7.67 (1H, brs). |
| 215 | 80 | 146–148 | | |
| 216 | 90 | 151–153 | | |
| 217 | not less than 97 | 112–114 | | |
| 218 | 85 | liquid | NMR: | 1.90 (2H, m), 2.60 (2H, m), 2.62 (3H, d, J=5.4), 3.36 (3H, s), 4.98 (1H, t, J=1.8), 5.90 (1H, brs), 6.38 (2H, m), 6.80 (3H, d, J=9.0), 7.12 (2H, d, J=9.0), 7.84 (1H, brs). |
| 219 | 76 | 123–125 | | |
| 220 | 70 | liquid | NMR: | 1.90 (2H, m), 2.56 (2H, m), 3.04 (3H, s), 3.40 (3H, s), 3.64 (3H, s), 5.01 (1H, t, J=1.8), 6.30–6.96 (3H, m), 6.88 (2H, d, J=9.0), 7.36 (2H, d, J=9), 7.66 (1H, brs). |
| 221 | 84 | 139–140 | | |
| 222 | not less than 97 | 88–90 | | |
| 223 | 89 | 136–138 | | |
| 224 | 85 | 127–129 | | |
| 225 | 87 | liquid | NMR: | 1.00 (3H, t, J=7.2), 1.80 (4H, m), 2.60 (1H, m), 3.21 (3H, s), 3.82 (3H, s), 4.16 (2H, t, J=5.4), 6.42 (1H, d, J=2.7), 6.49 (1H, dd, J=2.7, 8.1), 6.98 (2H, d, J=9.0), 7.06 (1H, d, J=8.1), 7.42 (2H, d, J=9.0), 7.64 (1H, brs). |
| 226 | 61 | 158–160 | | |
| 227 | 88 | 139–142 | | |
| 228 | not less than 97 | liquid | NMR: | 0.96 (3H, d, J=7.2), 1.16 (3H, d, J=7.2), 2.00–2.40 (1H, m), 2.70–3.10 (1H, m), 3.17 (3H, s), 3.75 (3H, s), 3.80–4.10 (2H, m), 6.44 (1H, d, J=2.7), 6.50 (1H, dd, J=2.7, 8.1), 6.98 (2H, d, J=8.1), 7.04 (1H, d, J=8.1), 7.35 (2H, d, J=8.1), 7.70 (1H, brs). |
| 229 | not less than 97 | 58.5–59.5 | | |
| 230 | 90 | 158–160 | | |
| 231 | 90 | 157–158 | | |
| 232 | 90 | liquid | NMR: | 1.30, 1.35 (total 3H, d, J=7.2), 1.60–2.28 (2H, m), |

TABLE 13-continued

| Compound No. | Yield (%) | Melting point (°C.) | Spectral data | |
|---|---|---|---|---|
| | | | | 2.94 (1H, m), 2.98 (6H, s), 3.47, 3.51 (total 3H, s), 5.07 (1H, m), 6.36–7.44 (8H, m). |
| 233 | 92 | liquid | NMR: | 1.30, 1.36 (total 3H, d, J=7.2), 1.60–2.30 (2H, m), 3.00 (1H, m), 3.19 (3H, s), 3.47, 3.52 (total 3H, s), 3.77 (3H, m), 5.08 (1H, m), 6.40–7.56 (7H, m), 7.68 (1H, brs). |
| 234 | 90 | liquid | NMR: | 1.00–1.50 (6H, m), 1.60–2.28 (2H, m), 3.02 (6H, s), 3.08 (1H, m), 3.24–4.08 (2H, m), 5.18 (1H, dd, J=3.6, 7.2), 6.38 (1H, brs) 6.40–7.48 (7H, m). |
| 235 | not less than 97 | liquid | NMR: | 1.02–1.58 (6H, m), 1.60–2.30 (2H, m), 3.10 (1H, m), 3.20 (3H, s), 3.50–4.20 (2H, m), 3.79 (3H, s), 5.18 (1H, dd, J=3.6, 7.2), 6.40–7.56 (7H, m), 7.68 (1H, brs). |
| 236 | 80 | 179–180 | | |
| 237 | not less than 97 | 129–131 | NMR: | 1.40 (3H, d, J=7.2), 1.60–2.44 (2H, m), 3.18 (3H, s), 3.44 (3H, s), 3.76 (3H, s), 4.20 (1H, m), 4.56 (1H, dd, J=6.3, 10.8), 6.36 (1H, d, J=2.7), 6.55 (1H, dd, J=2.7, 9.0), 6.97 (2H, d, J=9.0), 7.30 (1H, d, J=9.0), 7.42 (2H, d, J=9.0), 7.64 (1H, m). |
| 238 | 82 | 135–137 | | |
| 239 | not less than 97 | 151–152 | | |
| 240 | not less than 97 | 109–110 | NMR: | 0.96 (3H, d, J=7.2), 1.26 (3H, d, J=7.2), 2.00–3.08 (3H, m), 3.19 (3H, s), 3.77 (3H, s), 4.08–4.20 (1H, m), 6.42 (1H, d, J=2.7), 6.47 (1H, dd, J=2.7, 9.0), 6.96 (1H, d, J=9.0), 6.98 (2H, d, J=9.0), 7.42 (2H, d, J=9.0), 7.68 (1H, brs). |
| 241 | 71 | liquid | NMR: | 0.8–1.12 (6H, m), 1.20–1.81 (3H, m), 2.20–2.80 (2H, m), 3.04 (6H, s), 3.98 (1H, m), 6.30 (1H, brs), 6.40–7.40 (7H, m). |
| 242 | not less than 97 | 115–117 | | |
| 243 | 86 | 142–143 | IR: | 3335 ($\nu_{NH}$), 1644 ($\nu_{c=o}$). |
| 244 | 88 | 88–90 | IR: | 3360 ($\nu_{NH}$), 1660 ($\nu_{c=o}$). |
| 245 | 81 | 109–111 | IR: | 3290 ($\nu_{NH}$), 1638 ($\nu_{c=o}$). |
| 246 | not less than 97 | liquid | IR: NMR: | 3320 ($\nu_{NH}$), 1675 ($\nu_{c=o}$). 0.92 (3H, t, J=7.2), 1.24 (3H, s), 1.40–1.92 (6H, m), 2.70 (2H, t, J=7.2), 3.18 (3H, s), 3.76 (3H, s), 6.40 (1H, d, J=2.7), 6.46 (1H, dd, J=2.7, 9.0), 6.97 (3H, d, J=9.0), 7.40 (2H, d, J=9.0), 7.65 (1H, brs). |
| 247 | 82 | 119.5–120 | IR: | 3350 ($\nu_{NH}$), 1641 ($\nu_{c=o}$). |
| 248 | not less | 79–80.5 | IR: | 3310 ($\nu_{NH}$), 1660 ($\nu_{c=o}$). |
| 249 | 87 | 132.5–134 | IR: | 3360 ($\nu_{NH}$), 1647 ($\nu_{c=o}$). |
| 250 | not less than 97 | 94–95 | IR: | 3360 ($\nu_{NH}$), 1662 ($\nu_{c=o}$). |
| 251 | 77 | 105–106 | NMR: | 0.89 (6H, t, J=7.0), 1.25–1.67 (6H, m), 1.77 (2H, t, J=7.2), 2.68 (2H, t, J=7.2), 3.02 (6H, s), 6.26 (1H, brs), 6.39 (1H, d, J=2.7), 6.45 (1H, dd, J=2.7, 9.0), 6.93 (1H, d, J=9.0), 6.95 (2H, d, J=9.0), 7.39 (2H, d, J=9.0). |
| 252 | not less than 97 | liquid | NMR: | 0.89 (6H, t, J=7.5), 1.20–1.66 (6H, m), 1.77 (2H, t, J=7.2), 2.67 (2H, t, J=7.2), 3.17 (3H, s), 3.75 (3H, s), 6.39 (1H, d, J=2.7), 6.44 (1H, dd, J=2.7, 9.0), 6.95 (1H, d, J=9.0), 6.97 (2H, d, J=9.0), 7.40 (2H, d, J=9.0), 7.69 (1H, brs). |
| 253 | not less than 97 | 113–116 | IR: | 3330 ($\nu_{NH}$), 1637 ($\nu_{c=o}$). |
| 254 | 85 | 58–59.5 | IR: | 3355 ($\nu_{NH}$), 1638 ($\nu_{c=o}$). |
| 255 | not less than 97 | 99–100.5 | IR: | 3330 ($\nu_{NH}$), ($\nu_{c=o}$). |
| 256 | not less than 97 | 136–137.5 | | |
| 257 | not less than 97 | 144–144.5 | IR: NMR: | 3310 ($\nu_{NH}$), 1648 ($\nu_{c=o}$). 1.49 (3H, s), 1.62–2.08 (2H, m), 2.36–2.92 (2H, m), 3.03 (6H, s), 3.27 (3H, s), 6.40 (1H, brs), 6.44–7.46 (7H, m). |
| 258 | not less than 97 | liquid | IR: NMR: | 3330 ($\nu_{NH}$), 1672 ($\nu_{c=o}$). 1.52 (3H, s), 1.72–2.24 (2H, m), 2.40–3.04 (2H, m), 3.20 (3H, s), 3.29 (3H, s), 3.77 (3H, s), 6.47 (1H, d, J=2.7), 6.52 (1H, dd, J=2.7, 9.0), 7.00 (3H, d, J=9.0), 7.43 (2H, d, J=9.0), 7.66 (1H, brs). |
| 259 | 77 | 159.5–160.5 | IR: NMR: | 3270 ($\nu_{NH}$), 1632 ($\nu_{c=o}$). 1.05 (3H, t, J=7.2), 1.53 (3H, s), 1.70–2.24 (2H, m), 2.56–3.20 (2H, m), 3.03 (6H, s), 3.59 (2H, q, J=7.2), 6.34 (1H, brs), 6.40–7.44 (7H, m). |
| 260 | not less than 97 | liquid | IR: | 3310 ($\nu_{NH}$), 1670 ($\nu_{c=o}$). |
| 261 | 85 | liquid | NMR: | 0.85 (3H, d, J=7.2), 1.12 (3H, d, J=7.2), 1.52 (3H, s), 1.64–2.24 (2H, m), 2.36–2.80 (2H, m), 3.00 (6H, s), |

TABLE 13-continued

| Compound No. | Yield (%) | Melting point (°C.) | Spectral data | | |
|---|---|---|---|---|---|
| | | | | 4.22 (1H, m), 6.38–6.58 (3H, m), 6.84–7.06 (3H, m), 7.22–7.40 (2H, m). | |
| 262 | 91 | liquid | NMR: | 0.84 (3H, d, J=7.2), 1.13 (3H, d, J=7.2), 1.54 (3H, s), 1.64–2.18 (2H, m), 2.30–3.00 (2H, m), 3.15 (3H, s), 3.73 (3H, s), 4.20 (1H, m), 6.36–6.58 (2H, m), 6.84–7.04 (3H, m). | |
| 263 | not less than 97 | 147–148 | | | |
| 264 | 90 | 141–143 | IR: | 3290 ($\nu_{NH}$), 1636 ($\nu_{C=O}$). | |
| 265 | not less than 97 | liquid | IR:<br>NMR: | 3420 ($\nu_{NH}$), 3330 ($\nu_{NH}$), 1675 ($\nu_{C=O}$).<br>0.96 (3H, t, J=7.2), 1.64–14 2.24 (4H, m), 2.40–3.00 (2H, m), 3.19 (3H, s), 3.23 (3H, s), 3.76 (3H, s), 6.47 (1H, d, J=2.7), 7.32 (1H, dd, J=2.7, 9.0), 6.98 (3H, d, J=9.0), 7.42 (2H, d, J=9.0), 7.67 (1H, brs). | |
| 266 | not less than 97 | 114–116 | | | |
| 267 | not less than 97 | 146–147.5 | | | |
| 268 | not less than 97 | liquid | NMR: | 1.29 (3H, t, J=7.2), 1.50 (3H, s), 1.90–2.20 (2H, m), 3.08 (1H, m), 3.19 (3H, s), 3.26 (3H, s), 3.76 (3H, s), 6.44 (1H, d, J=2.7), 6.56 (1H, dd, J=2.7, 9.0), 6.98 (2H, d, J=9.0), 7.16 (1H, d, J=9.0), 7.42 (2H, d, J=9.0), 7.68 (1H, brs). | |
| 269 | not less than 97 | 163.5–164.5 | | | |
| 270 | 77 | 167–168 | | | |
| 271 | 84 | liquid | NMR: | 0.95 (3H, t, J=7.2), 1.30 (3H, d, J=6.3), 1.60–2.24 (4H, m), 3.00 (1H, m), 3.18 (3H, s), 3.22 (3H, s), 3.76 (3H, s), 6.47 (1H, d, J=2.7), 6.55 (1H, dd, J=2.7, 9.0), 6.97 (2H, d, J=9.0), 7.17 (1H, d, J=9.0), 7.42 (2H, d, J=9.0), 7.70 (1H, brs). | |
| 272 | 90 | liquid | NMR: | 1.07 (3H, d, J=7.2), 1.38 (3H, d, J=7.2), 1.60–2.00 (1H, m), 3.02 (6H, s), 3.31 (3H, s), 3.80–4.36 (2H, m), 6.20–7.44 (8H, m). | |
| 273 | 87 | liquid | NMR: | 1.06 (3H, d, J=7.2), 1.37 (3H, d, J=7.2), 1.64–2.10 (1H, m), 3.18 (3H, s), 3.30 (3H, s), 3.76 (3H, s), 3.90–4.40 (2H, m), 6.38 (1H, d, J=2.7), 6.52 (1H, dd, J=2.7, 9.0), 6.98 (2H, d, J=9.0), 7.25 (1H, d, J=9.0), 7.43 (2H, d, J=9.0), 7.68 (1H, brs). | |
| 274 | not less than 97 | 163–164 | | | |
| 275 | 92 | 58–59 | NMR: | 0.99 (3H, d, J=7.2), 1.13 (3H, s), 1.35 (3H, s), 1.60–2.08 (1H, m), 2.30–2.88 (2H, m), 2.98 (6H, m), 6.30–7.44 (8H, m). | |
| 276 | not less than 97 | 82.5–83.5 | NMR: | 1.01 (3H, d, J=7.2), 1.15 (3H, s), 1.36 (3H, s), 1.68–2.12 (1H, m), 2.19 (1H, dd, J=9.0, 16.2), 2.64 (1H, d, J=6.3, 16.2), 3.19 (3H, s), 3.76 (3H, s), 6.39 (1H, d, J=2.7), 6.46 (1H, dd, J=2.7, 9.0), 6.95 (1H, d, J=9.0), 6.98 (2H, d, J=9.0), 7.42 (2H, d, J=9.0), 7.68 (1H, brs). | |
| 277 | 94 | 146–147.5 | | | |
| 278 | 63 | liquid | NMR: | 1.08 (3H, d, J=7.2), 1.49 (3H, s) 1.98 (1H, m), 2.44–2.76 (2H, m), 3.00 (6H, s), 3.23 (3H, s), 6.38 (1H, brs), 6.45 (1H, d, J=2.7), 6.50 (1H, dd, J=2.7, 9.0), 6.94 (3H, d, J=9.0), 7.32 (2H, d, J=9.0). | |
| 279 | not less than 97 | liquid | NMR: | 1.08 (3H, d, J=7.2), 1.78–2.20 (1H, m), 2.36–2.80 (2H, m), 3.20 (3H, s), 3.24 (3H, s), 3.77 (3H, s), 6.40–7.56 (7H, m), 7.66 (1H, brs). | |
| 280 | 93 | liquid | NMR: | 0.94 (3H, t, J=7.2), 1.25 and 1.36 (total 3H, s), 1.50–1.80 (2H, m), 1.81–2.10 (2H, m), 3.02 (6H, s), 3.44 and 3.46 (total 3H, s), 4.40 (1H, brs), 6.30 (1H, brs), 6.38 (1H, d, J=2.7), 6.54 (1H, dd, J=2.7, 8.1), 6.97 (2H, d, J=8.1), 7.20–7.50 (3H, m). | |
| 281 | 88 | liquid | NMR: | 0.94 (3H, t, J=7.2), 1.24 and 1.34 (total 3H, s), 1.50–1.80 (2H, m), 3.18 (3H, s), 3.44 and 3.46 (total 3H, s), 3.76 (3H, s), 4.4 (1H, brs), 6.38 (1H, d, J=2.7), 6.54 (1H, dd, J=2.7, 8.1), 6.98 (2H, d, J=8.1), 7.28 (1H, d, J=8.1), 7.42 (2H, d, J=8.1), 7.66 (1H, brs). | |
| 282 | 90 | liquid | IR: | 3300 ($\nu_{NH}$), 1640 ($\nu_{C=O}$). | |
| 283 | 94 | liquid | IR: | 3400 ($\nu_{NH}$), 3310 ($\nu_{NH}$), 1640 ($\nu_{C=O}$). | |
| 284 | 80 | liquid | NMR: | 0.89 (6H, t, J=7.2), 1.50–2.10 (6H, m), 3.03 (6H, s), 3.46 (3H, s), 4.38 (1H, t, J=6.3), 6.26 (1H, brs), 6.39 (1H, d, J=2.7), 6.54 (1H, dd, J=2.7, 8.1), 6.98 (2H, d, J=8.1), 7.28 (1H, d, J=8.1), 7.34 (2H, d, J=8.1). | |
| 285 | 80 | liquid | NMR: | 0.89 (6H, t, J=7.2), 1.50–2.10 (6H, m), 3.18 (3H, s), 3.46 (3H, s), 3.76 (3H, s), 4.39 (1H, t, J=6.3), 6.39 (1H, d, J=2.7), 6.54 (1H, dd, J=2.7, 8.1), | |

TABLE 13-continued

| Compound No. | Yield (%) | Melting point (°C.) | Spectral data |
|---|---|---|---|
| | | | 6.99 (2H, d, J=8.1), 7.30 (1H, d, J=8.1), 7.44 (2H, d, J=8.1), 7.68 (1H, brs). |
| 286 | 77 | 63–65 | |
| 287 | 43 | liquid | NMR: 0.90 (6H, t, J=7.2), 1.00–2.20 (8H, m), 3.03 (6H, s), 3.45 (3H, s), 4.38 (1H, t, J=7.2), 6.26 (1H, brs), 6.39 (1H, d, J=2.7), 6.52 (1H, dd, J=2.7, 8.1), 6.97 (2H, d, J=8.1), 7.29 (1H, d, J=8.1), 7.44 (2H, d, J=8.1). |
| 288 | 63 | liquid | NMR: 0.90 (6H, t, J=7.2), 1.00–2.20 (8H, m), 3.19 (3H, s), 3.46 (3H, s), 3.77 (3H, s), 4.38 (1H, t, J=7.2), 6.39 (1H, d, J=2.7), 6.52 (1H, dd, J=2.7, 8.1), 6.98 (2H, d, J=8.1), 7.30 (1H, d, J=8.1), 7.42 (2H, d, J=8.1), 7.66 (1H, brs). |
| 289 | 57 | 68–69 | |
| 290 | 86 | 67–68 | NMR: 1.01 (3H, t, J=7.2), 1.52–2.12 (4H, m), 2.98 (6H, s), 3.92–4.40 (5H, m), 6.44 (1H, dd, J=2.7, 9.0), 6.59 (1H, d, J=2.7), 6.65 (1H, brs), 6.92 (2H, d, J=9.0), 7.32 (3H, d, J=9.0). |
| 291 | 91 | liquid | NMR: 1.03 (3H, t, J=7.2), 1.56–2.20 (4H, m), 3.20 (3H, s), 3.78 (3H, s), 4.00–4.50 (5H, m), 6.39 (1H, d, J=2.7), 6.57 (1H, dd, J=2.7, 9.0), 7.00 (2H, d, J=9.0), 7.44 (3H, d, J=9.0), 7.68 (1H, brs). |
| 292 | 86 | 173–175 | |
| 293 | 83 | 78–79.5 | |
| 294 | 73 | liquid | NMR: 1.00 (6H, d, J=6.3), 1.85–1.94 (3H, m), 3.20 (3H, s), 3.80 (3H, s), 4.02 (1H, m), 4.15 (4H, m), 6.30–6.60 (3H, m), 6.92 (2H, d, J=9.0), 7.30 (2H, d, J=9.0). |
| 295 | 85 | 160–161 | NMR: 0.97 (3H, d, J=7.0), 1.37 (3H, d, J=7.0), 2.11 (1H, m), 3.02 (6H, s), 4.09–4.35 (5H, m), 6.30 (1H, brs), 6.35 (1H, d, J=2.7), 6.56 (1H, dd, J=2.7, 9.0), 6.95 (2H, d, J=9.0), 7.20 (1H, d, J=9.0), 7.33 (2H, d, J=9.0). |
| 296 | not less than 97 | 109–110 | NMR: 0.96 (3H, d, J=7.0), 1.36 (3H, d, J=7.0), 2.11 (1H, m), 3.16 (3H, s), 3.74 (3H, s), 4.08–4.40 (5H, m), 6.35 (1H, d, J=2.7), 6.51 (1H, dd, J=27, 9.0), 6.97 (2H, d, J=9.0), 7.20 (1H, d, J=9.0), 7.42 (2H, d, J=9.0), 7.71 (1H, brs). |
| 297 | 92 | 77–79 | |
| 298 | 92 | liquid | NMR: 1.42 (6H, s), 2.13 (2H, s), 3.20 (3H, s), 3.78 (3H, s), 4.00–4.30 (4H, m), 6.38 (1H, d, J=2.7), 6.59 (1H, dd, J=2.7, 9.0), 7.02 (2H, d, J=9.0), 7.36 (1H, d, J=9.0), 7.50 (2H, d, J=9.0), 7.70 (1H, brs). |
| 299 | 80 | liquid | NMR: 0.92 (3H, t, J=7.2), 1.33 (3H, s), 1.73 (2H, q, J=7.2), 2.06 (1H, d, J=14.4), 2.26 (1H, d, J=14.4), 2.78 (3H, d, J=5.4), 4.00–4.30 (4H, m), 5.20 (1H, brs), 6.35 (1H, d, J=2.7), 6.54 (1H, dd, J=2.7, 8.1), 6.98 (2H, d, J=8.1), 7.20–7.60 (3H, m). |
| 300 | 84 | liquid | NMR: 0.92 (3H, t, J=7.2), 1.33 (3H, s), 1.73 (2H, q, J=7.2), 2.05 (1H, d, J=14.4), 2.26 (1H, d, J=14.4), 3.00 (6H, s), 4.00–4.30 (4H, m), 6.35 (1H, d, J=2.7), 6.42 (1H, brs), 6.54 (1H, dd, J=2.7, 8.1), 6.98 (2H, q, J=8.1), 7.20–7.30 (3H, m). |
| 301 | 90 | liquid | NMR: 0.92 (3H, t, J=7.2), 1.33 (3H, s), 1.73 (2H, q, J=7.2), 2.03 (1H, d, J=14.4), 2.21 (1H, d, J=14.4), 3.18 (3H, s), 3.74 (3H, s), 4.0–4.3 (4H, m), 6.35 (1H, d, J=2.7), 6.54 (1H, dd, J=2.7, 8.1), 6.98 (2H, d, J=8.1), 6.98 (2H, d, J=8.1), 7.45 (3H, d, J=8.1). |
| 302 | 80 | 73–76.5 | IR: 3320 ($\nu_{NH}$), 1640 ($\nu_{C=O}$). |
| 303 | not less than 97 | liquid | IR: 3400 ($\nu_{NH}$), 3325 ($\nu_{NH}$), 1678 ($\nu_{C=O}$). |
| 304 | 80 | liquid | NMR: 0.87 (6H, t, J=7.2), 1.68 (4H, q, J=7.2), 2.09 (2H, s), 3.03 (6H, s), 4.00–4.30 (4H, m), 6.24 (1H, brs), 6.35 (1H, d, J=2.7), 6.54 (1H, dd, J=2.7, 8.1), 6.96 (2H, d, J=8.1), 7.30 (1H, d, J=8.1), 7.42 (2H, d, J=8.1). |
| 305 | 87 | liquid | NMR: 0.87 (6H, t, J=7.2), 1.68 (4H, q, J=7.2), 2.09 (2H, s), 3.18 (3H, s), 3.76 (3H, s), 4.00–4.30 (4H, m), 6.35 (1H, d, J=2.7), 6.54 (1H, dd, J=2.7, 8.1), 6.96 (2H, d, J=8.1), 7.30 (1H, d, J=8.1), 7.42 (2H, d, J=8.1), 7.68 (1H, brs). |
| 306 | 83 | liquid | NMR: 0.87 (6H, t, J=7.2), 1.68 (4H, q, J=7.2), 2.08 (2H, s), 2.10–2.50 (2H, m), 2.74 (3H, d, J=4.4), 4.00–4.30 (4H, m), 5.58 (1H, brs), 6.35 (1H, d, J=2.7), 6.52 (1H, d, J=2.7, 8.1), 6.98 (2H, d, J=8.1), 7.24 (1H, d, J=8.1), 7.44 (2H, d, J=8.1), 7.56 (1H, brs). |
| 307 | 70 | 182–187 | |
| 308 | 75 | 126–127 | NMR: 0.88 (6H, t, J=7.2), 1.10–1.50 (2H, m), 1.69 (4H, q, J=7.2), 2.09 (2H, s), 3.17 (3H, s), 3.72 (3H, s), 3.90–4.30 (4H, m), 6.35 (1H, d, J=2.7Hz), 6.55 (1H, dd, J=2.7, 8.1), 6.98 (2H, d, J=8.1), 7.24 (1H, d, |

TABLE 13-continued

| Compound No. | Yield (%) | Melting point (°C.) | Spectral data |
|---|---|---|---|
| | | | J=8.1), 7.44 (2H, d, J=8.1), 7.78 (1H, brs). |
| 309 | not less than 97 | liquid | NMR: 1.36 (3H, s), 1.62 (3H, s), 1.68 (1H, s), 1.80 (3H, s), 3.02 (6H, s), 6.35 (1H, brs), 6.38 (1H, d, J=2.7), 6.53 (1H, dd, J=2.7, 9.0), 6.94 (2H, d, J=9.0), 7.09 (1H, d, J=9.0), 7.33 (2H, d, J=9.0). |
| 310 | not less than 97 | liquid | NMR: 1.35 (3H, s), 1.61 (3H, s), 1.68 (1H, s), 1.79 (3H, s), 3.17 (3H, s), 3.75 (3H, s), 6.38 (1H, d, J=2.7), 6.52 (1H, dd, J=2.7, 9.0), 6.96 (2H, d, J=9.0), 7.09 (1H, d, J=9.0), 7.41 (2H, d, J=9.0), 7.67 (1H, brs). |
| 311 | not less than 97 | 161–162 | |
| 312 | 89 | 40–43 | NMR: 1.80–2.24 (6H, m), 3.01 (6H, s), 3.06 (1H, m), 3.53 (3H, s), 6.39 (1H, dd, J=2.7, 9.0), 6.43 (1H, d, J=2.7), 6.52 (1H, brs), 6.88 (1H, d, J=9.0), 6.94 (2H, d, J=9.0), 7.34 (2H, d, J=9.0). |
| 313 | not less than 97 | liquid | NMR: 1.76–2.30 (6H, m), 3.01 (1H, m), 3.12 (3H, s), 3.47 (3H, s), 3.71 (3H, s), 6.26–7.48 (7H, m), 7.66 (1H, brs). |
| 314 | 93 | 166–168 | |
| 315 | not less than 97 | 58–59 | |
| 316 | 89 | liquid | NMR: 1.40–1.92 (6H, m), 2.00–2.30 (2H, m), 3.18 (1H, m), 3.19 (3H, s), 3.38 (3H, s), 3.76 (3H, s), 6.46 (1H, dd, J=2.7, 9.0), 6.49 (1H, d, J=2.7), 6.96 (1H, d, J=9.0), 7.00 (2H, d, J=9.0), 7.45 (2H, d, J=9.0), 7.73 (1H, brs). |
| 317 | 97 | 211–213 | IR: 3330 ($\nu_{NH}$), 3050 ($\nu_{OH}$), 1624 ($\nu_{c=o}$). NMR: 1.29 (3H, s), 1.47 (3H, s), 1.57 (3H, s), 1.77 (1H, d, J=14.4), 2.00 (1H, d, J=14.4), 3.09 (3H, s), 5.75 (1H, brs), 6.28 (1H, d, J=2.7), 6.52 (1H, dd, J=2.7, 9.0), 6.91 (2H, d, J=9.0), 7.21 (1H, d, J=9.0), 7.39 (2H, d, J=9.0), 8.13 (1H, brs). |
| 318 | 93 | 190–191.5 | IR: 3350 ($\nu_{NH}$), 3040 ($\nu_{OH}$), 1627 ($\nu_{c=o}$). NMR: 1.28 (3H, s), 1.46 (3H, s), 1.56 (3H, s), 1.78 (1H, d, J=14.4), 2.00 (1H, d, J=14.4), 3.03 6H, s), 6.32 (1H, d, J=2.7), 6.54 (1H, dd, J=2.7, 9.0), 6.92 (2H, d, J=9.0), 7.19 (1H, d, J=9.0), 7.38 (2H, d, J=9.0). |
| 319 | 97 | 137–139 | IR: 3410 ($\nu_{NH}$), 3050 ($\nu_{OH}$), 1627 ($\nu_{c=o}$). NMR: 1.28 (3H, s), 1.41 (3H, s), 1.56 (3H, s), 1.80 (1H, d, J=15.3), 2.02 (1H, d, J=15.3), 3.16 (3H, s), 3.38 (1H, brs), 3.73 (3H, s), 6.38 (1H, d, J=2.7), 6.53 (1H, dd, J=2.7, 9.0), 6.95 (2H, d, J=9.0), 7.20 (1H, d, J=9.0), 7.40 (2H, d, J=9.0), 7.73 (1H, brs). |
| 320 | 72 | 128.5–130 | NMR: 1.38 (3H, d, J=7.2), 1.64–2.00 (2H, m), 2.60–2.92 (2H, m), 3.00 (6H, s), 4.00–4.36 (1H, m), 6.63 (1H, brs), 6.70–7.00 (4H, m), 7.90 (1H, dd, J=2.7, 9.0), 8.01 (1H, d, J=2.7). |
| 321 | 91 | 93–94 | NMR: 1.39 (3H, d, J=7.2), 1.64–2.00 (2H, m), 2.68–3.00 (2H, m), 3.20 (3H, s), 3.78 (3H, s), 3.92–4.40 (1H, m), 6.72–7.00 (4H, m), 7.69 (1H, brs), 8.01 (1H, dd, J=2.7, 9.0), 8.14 (1H, d, J=2.7). |
| 322 | not less than 97 | 180–182 | |
| 323 | 95 | 154–155 | IR: 3335 ($\nu_{NH}$), 1642 ($\nu_{c=o}$). |
| 324 | not less than 97 | 108–109 | IR: 3310 ($\nu_{NH}$), 1665 ($\nu_{c=o}$). |
| 325 | not less than 97 | 100–102 | NMR: 1.32 (6H, s), 1.77 (2H, t, J=7.2), 2.73 (2H, t, J=7.2), 3.00 (6H, s), 6.51 (1H, brs), 6.44–6.90 (4H, m), 7.89 (1H, dd, J=2.7, 9.0), 7.99 (1H, d, J=2.7). |
| 326 | 78 | liquid | NMR 1.36 (6H, s), 1.78 (2H, t, J=7.2), 2.75 (2H, t, J=7.2), 3.10 (3H, s), 3.77 (3H, s), 6.67–6.92 (4H, m), 7.70 (1H, brs), 7.96 (1H, dd, J=2.7, 9.0), 8.10 (1H, d, J=2.7). |
| 327 | 75 | 168–169 | IR: 3285 ($\nu_{NH}$), 1643 ($\nu_{c=o}$). |
| 328 | 86 | 106–108 | IR: 3290 ($\nu_{NH}$), 1667 ($\nu_{c=o}$). |
| 329 | 84 | 174–176 | IR: 3265 ($\nu_{NH}$), 1640 ($\nu_{c=o}$). |
| 330 | not less than 97 | 91–92.5 | IR: 3390 ($\nu_{NH}$), 1686 ($\nu_{c=o}$). |
| 332 | 74 | 171.5–172 | IR: 3280 ($\nu_{NH}$), 1635 ($\nu_{c=o}$). |
| 333 | not less than 97 | liquid | IR: 3310 ($\nu_{NH}$), 1672 ($\nu_{c=o}$). |
| 334 | 82 | 191–193 | NMR: 1.34 (6H, d, J=6.9), 2.68–3.28 (1H, m), 2.80 (3H, d, J=4.4), 5.02 (1H, brs), 6.30 (1H, s), 6.64–7.60 (8H, m). |
| 335 | 73 | 153–155 | NMR: 1.35 (6H, d, J=6.9), 2.98–3.10 (1H, m), 3.04 (6H, s), 6.26 (1H, s), 6.36 (1H, brs), 6.84–7.46 (7H, m). |
| 336 | not less than 97 | liquid | NMR: 1.34 (6H, d, J=6.9), 2.86–3.30 (1H, m), 3.16 (3H, s), 3.72 (3H, s), 6.28 (1H, s), 6.88 (1H, dd, J=2.7, 9.0), 6.93 (2H, d, J=9.0), 7.10 (1H, d, J=2.7), 7.35 (1H, d, J=9.0), 7.40 (2H, d, J=9.0), 7.72 (1H, brs). |

TABLE 13-continued

| Compound No. | Yield (%) | Melting point (°C.) | Spectral data |
|---|---|---|---|
| 337 | 77 | 137–138 | NMR: 0.98 (3H, d, J=6.9), 1.02 (3H, d, J=6.9), 1.90–2.28 (1H, m), 2.64 (2H, dd, J=2.7, 6.7), 3.00 (6H, s), 6.32 (1H, s), 6.48 (1H, brs), 6.80–7.04 (3H, m), 7.08 (1H, d, J=2.7), 7.30 (2H, d, J=9.0), 7.34 (1H, d, J=9.0). |
| 338 | 86 | 67–69 | NMR: 0.89 (6H, d, J=6.9), 1.76–2.20 (1H, m), 2.52 (2H, d, J=6.9), 3.08 (3H, s), 3.64 (3H, s), 6.22 (1H, s), 6.68–7.50 (7H, m), 7.64 (1H, brs). |
| 339 | 80 | 123–124 | NMR: 1.28 (3H, t, J=7.7), 2.62 (2H, q, J=7.7), 3.00 (6H, s), 6.44 (1H, brs), 6.80–7.50 (8H, m). |
| 340 | 78 | liquid | IR: 3325 ($\nu_{NH}$), 1675 ($\nu_{c=o}$). |
| 341 | not less than 97 | liquid | IR: 3325 ($\nu_{NH}$), 1655 ($\nu_{c=o}$). |
| 342 | 68 | liquid | NMR: 0.80–1.84 (5H, m), 2.56 (2H, t, J=7.7), 2.95 (6H, s), 6.68–7.50 (9, m). |
| 343 | 83 | liquid | NMR: 0.80–1.84 (5H, m), 2.56 (2H, t, J=7.7), 3.16 (3H, s), 3.71 (3H, s), 6.72–7.74 (8H, m), 7.78 (1H, brs). |
| 344 | 85 | liquid | NMR: 1.30 (6H, d, J=6.7), 2.90–3.14 (1H, m), 3.02 (6H, s), 6.48 (1H, brs), 6.70–7.56 (8H, m). |
| 345 | 92 | liquid | NMR: 1.32 (6H, d, J=6.7), 2.86–3.24 (1H, m), 3.21 (3H, s), 3.78 (3H, s), 6.70–7.56 (8H, m), 7.71 (1H, brs). |
| 346 | not less than 97 | liquid | NMR: 1.42 (3H, d, J=6.3), 2.84 (1H, dd, J=7.2, 14.4), 3.00 (6H, s), 2.96 (1H, dd, J=7.2, 14.4), 2.92 (1H, m), 6.66 (1H, brs), 6.68–7.10 (4H, m), 7.80–8.08 (2H, m). |
| 347 | 74 | liquid | NMR: 1.42 (3H, d, J=6.3), 2.85 (1H, dd, J=7.2, 14.4), 3.20 (3H, s), 3.38 (1H, dd, J=7.2, 14.4), 3.78 (3H, s), 4.94 (1H, m), 6.72–7.16 (4H, m), 7.64 (1H, brs), 7.92–8.20 (2H, m). |
| 348 | 84 | 100.5–101.5 | NMR: 1.47 (3H, d, J=6.4), 2.86 (1H, dd, J=7.7, 15.4), 3.00 (6H, s), 3.38 (1H, dd, J=7.7, 15.4), 5.00 (1H, m), 6.44 (1H, brs), 6.68–6.90 (3H, m), 6.94 (2H, d, J=9.0), 7.32 (2H, d, J=9.0). |
| 349 | 87 | 86–88 | NMR: 1.46 (3H, d, J=6.4), 2.88 (1H, dd, J=7.7, 15.4), 3.17 (3H, s), 3.40 (1H, dd, J=7.7, 15.4), 3.75 (3H, s), 5.00 (1H, m), 6.66–6.96 (3H, m), 6.97 (2H, d, J=9.0), 7.40 (2H, d, J=9.0), 7.64 (1H, brs). |
| 350 | 95 | 161–162 | IR: 3320 ($\nu_{NH}$), 3280 ($\nu_{NH}$), 1635 ($\nu_{c=o}$). |
| 351 | 81 | 157–158 | IR: 3220 ($\nu_{NH}$), 1635 ($\nu_{c=o}$). |
| 352 | 81 | 93–93.5 | IR: 3280 ($\nu_{NH}$), 1660 ($\nu_{c=o}$). |
| 353 | 76 | 166.5–168 | NMR: 1.24 (6H, s), 1.79 (2H, t, J=7.1), 2.81 (2H, t, J=7.1), 3.00 (6H, s), 6.33 (1H, brs), 6.74–6.92 (3H, m), 6.84 (2H, d, J=9.0), 7.26 (2H, d, J=9.0). |
| 354 | 87 | 118–119.5 | NMR: 1.27 (6H, s), 1.80 (2H, t, J=7.1), 2.82 (2H, t, J=7.1), 3.18 (3H, s), 3.76 (3H, s), 6.68–6.96 (3H, m), 6.88 (2H, d, J=9.0), 7.36 (2H, d, J=9.0), 7.64 (1H, brs). |
| 355 | not less than 97 | 190–191 | |
| 356 | 77 | 174–175 | |
| 357 | 89 | 104–105 | |
| 358 | not less than 97 | 175.5–176.5 | |
| 359 | 82 | 153–155 | |
| 360 | not less than 97 | liquid | NMR: 1.19 (3H, d, J=7.2), 1.37 (3H, s), 1.39 (3H, s), 2.22 (3H, s), 3.09 (1H, q, J=7.2), 3.20 (3H, s), 3.77 (3H, s), 6.19 (1H, brs), 6.35 (1H, brs), 6.96 (2H, d, J=9.0), 7.43 (2H, d, J=9.0), 7.69 (1H, brs). |
| 361 | not less than 97 | 116–117 | |
| 362 | not less than 97 | 135–136 | |
| 363 | not less than 97 | liquid | NMR: 0.92 (3H, t, J=7.2), 1.18 (3H, d, J=6.3), 1.30 (3H, s), 1.66 (2H, q, J=7.2), 2.20 (3H, s), 3.12 (1H, q, J=6.3), 3.18 (3H, s), 3.76 (3H, s), 6.15 (1H, brs), 6.32 (1H, brs), 6.92 (2H, d, J=9.0), 7.39 (2H, d, J=9.0), 7.64 (1H, brs). |
| 364 | 65 | liquid | NMR: 1.29 (3H, s), 1.80 (2H, t, J=6.7), 2.16 (3H, s), 2.58 (2H, t, J=6.7), 3.04 (6H, s), 6.26 (1H, d, J=2.7), 6.40 (1H, d, J=2.7), 6.96 (2H, d, J=9.0), 7.32 (2H, d, J=9.0). |
| 365 | 80 | liquid | NMR: 1.28 (6H, s), 1.78 (2H, t, J=7.1), 2.16 (3H, s), 2.56 (2H, t, J=7.1), 3.16 (3H, s), 3.72 (3H, s), 6.28 (1H, d, J=2.7), 6.40 (1H, d, J=2.7), 6.97 (2H, d, J=9.0), 7.42 (2H, d, J=9.0), 7.76 (1H, brs). |
| 366 | not less than 97 | 164–165 | |
| 367 | 86 | 181–182 | |
| 368 | not less | 109–111 | |

TABLE 13-continued

| Compound No. | Yield (%) | Melting point (°C.) | Spectral data |
|---|---|---|---|
| 369 | than 97 not less than 97 | 176–177 | |
| 370 | 92 | 179–180.5 | |
| 371 | 88 | liquid | NMR: 1.14 (3H, d, J=7.2), 1.52 (3H, s), 1.80–2.12 (1H, m), 2.44 (2H, d, J=9.0), 3.21 (3H, s), 3.24 (3H, s), 3.79 (3H, s), 6.33 (1H, d, J=2.1), 6.45 (1H, d, J=2.1), 7.00 (2H, d, J=9.0), 7.43 (2H, d, J=9.0), 7.67 (1H, brs). |

The following Formulation Examples are given for the herbicide of this invention. All percentages in these examples are by weight.

FORMULATION EXAMPLE 1

Wettable powder

The compound [I] of this invention (10%), 3% of a sodium salt of a higher alcohol sulfate ester and 87% of kaolin were uniformly mixed and pulverized to form a wettable powder.

FORMULATION EXAMPLE 2

Emulsifiable concentrate

The compound [I] of this invention (20%), 10% of polyoxyethylene alkylaryl ether, 30% of cyclohexanone and 40% of dimethylformamide were uniformly dissolved to form an emulsifiable concentrate.

FORMULATION EXAMPLE 3

Granules

The compound [I] of this invention (5%), 40% of benzonite, 50% of clay and 5% of sodium ligninsulfonate were uniformly mixed and pulverized. The mixture was kneaded with water, granulated and dried to form granules.

FORMULATION EXAMPLE 4

Dust

The compound [I] of this invention (3%) and 97% of clay were uniformly mixed and pulverized to form a dust.

The following Test Examples specifically illustrate the herbicide of this invention.

TEST EXAMPLE 1

Herbicidal test in upland foliage treatment

Porcelain pots (12 cm in inside diameter) were filled with sieved upland farm soil, and seeds of cocklebur, blackjack, velvet leaf, jimsonweed, soybean, wheat, corn and rice were sown and covered with the soil (1 cm). They were grown in a greenhouse until the first leaf of soybean developed. A predetermined amount of each of the test compounds, formulated into a wettable powder in accordance with Formulation Example 1, was dispersed in 15 liters (per are) of water containing 500 ppm of Neoesterin as a sticker). The dispersion was sprayed to the leaves and stalks of the plants from the top of the plants by a small atomizer. After the treatment, the plants were grown further in the greenhouse for 20 days, Herbicidal effects and phytotoxicity on these plants were examined, and evaluated in accordance with the standards shown in Table 14. The results are shown in Table 15.

TABLE 14

| Index | Herbicidal effect and phytotoxicity |
|---|---|
| 5 | more than 99% to 100% (withered) |
| 4.5 | 90% to 99% |
| 4 | 80% to 89% |
| 3.5 | 70% to 79% |
| 3 | 60% to 69% |
| 2.5 | 50% to 59% |
| 2 | 40% to 49% |
| 1.5 | 30% to 39% |
| 1 | 20% to 29% |
| 0.5 | 1% to 19% |
| 0 | less than 1% (no herbicidal effect, or no phytotoxicity) |

TABLE 15

| Test compound | Rate kg/ha | Herbicidal effect | | | | Phytotoxicity | | | |
|---|---|---|---|---|---|---|---|---|---|
| | | A | B | C | D | E | F | G | H |
| 1 | 2 | 5 | 5 | 3 | 5 | 0 | 0 | 0 | 0 |
| | 1 | 3 | 5 | 2 | 5 | 0 | 0 | 0 | 0 |
| 2 | 2 | 5 | 5 | 5 | 5 | 0 | 2 | 1 | 2 |
| | 1 | 5 | 5 | 5 | 5 | 0 | 1 | 0 | 1 |
| 4 | 2 | 5 | 5 | 5 | 5 | 0 | 0 | 0 | 0 |
| | 1 | 5 | 5 | 5 | 5 | 0 | 0 | 0 | 0 |
| 5 | 2 | 5 | 5 | 5 | 5 | 0 | 0 | 0 | 0 |
| | 1 | 5 | 5 | 5 | 5 | 0 | 0 | 0 | 0.5 |
| 6 | 2 | 5 | 5 | 5 | | 0 | 0 | 0 | 0 |
| | 1 | 5 | 5 | 5 | | 0 | 0 | 0 | 0 |
| 7 | 2 | 5 | 5 | 5 | 5 | 0 | 0.5 | 0 | 2 |
| | 1 | 5 | 5 | 5 | 5 | 0 | 0 | 0 | 1 |
| 9 | 2 | 5 | 5 | 5 | 5 | 0.5 | 0.5 | | 2 |
| | 1 | 5 | 5 | 5 | 5 | 0 | 0 | | 0.5 |
| 10 | 2 | 5 | 5 | 5 | 5 | 0 | 2 | 0 | 1.5 |
| | 1 | 5 | 5 | 5 | 5 | 0 | 0 | 0 | 1 |
| 11 | 2 | 5 | 5 | 5 | 5 | 0 | 0 | 0 | 0 |
| | 1 | 5 | 5 | 4 | 5 | 0 | 0 | 0 | 0 |
| 16 | 2 | 5 | 4.5 | 5 | 5 | 0 | 2 | 0 | 0.5 |
| | 1 | 5 | 3 | 4.5 | 4.5 | 0 | 0 | 0 | 0 |
| 20 | 2 | 5 | 5 | 5 | 5 | 0 | 0 | | 0 |
| | 1 | 5 | 5 | 5 | 5 | 0 | 0 | | 0 |
| 21 | 2 | 5 | 5 | 5 | 5 | 0 | 0 | | 0 |
| | 1 | 5 | 5 | 1.5 | 5 | 0 | 0 | | 0 |
| 24 | 2 | 5 | 5 | 5 | 5 | 0 | 0 | | 0 |
| | 1 | 5 | 4 | 2.5 | 5 | 0 | 0 | | 0 |
| 31 | 2 | 5 | 5 | 5 | 5 | 0 | 0 | | 1 |
| | 1 | 5 | 5 | 5 | 5 | 0 | 0 | | 0.5 |
| 32 | 2 | 5 | 5 | 5 | 5 | 0 | 0 | | 3 |
| | 1 | 5 | 5 | 5 | 5 | 0 | 0 | | 1 |
| 33 | 2 | 5 | 5 | 5 | 5 | 0 | 0 | | |
| | 1 | 5 | 5 | 5 | 5 | 0 | 0 | | |
| 35 | 2 | 5 | 5 | 5 | 5 | 0 | 0 | | 1 |
| | 1 | 5 | 5 | 5 | 5 | 0 | 0 | | 0 |
| 36 | 2 | 5 | 5 | 5 | 5 | | 0 | | 1 |
| | 1 | 5 | 4.5 | 5 | 5 | | 0 | | 1 |
| 39 | 2 | 5 | 5 | 5 | 5 | 0 | 0 | | 0 |
| | 1 | 5 | 5 | 5 | 5 | 0 | 0 | | 0 |
| 43 | 2 | 5 | 5 | 5 | 5 | 0 | 0 | 0 | 1 |
| | 1 | 5 | 5 | 5 | 5 | 0 | 0 | 0 | 0 |
| 44 | 2 | 5 | 5 | 5 | 5 | 0 | 0 | 0 | 1 |
| | 1 | 5 | 5 | 5 | 5 | 0 | 0 | 0 | 0 |
| 55 | 2 | 5 | 5 | 5 | 5 | | 0 | 0 | 0 |
| | 1 | 5 | 5 | 5 | 5 | | 0 | 0 | 0 |
| 56 | 2 | 5 | 5 | 5 | 5 | | 0 | 0 | 0 |
| | 1 | 5 | 5 | 5 | 5 | | 0 | 0 | 0 |
| 57 | 2 | 5 | 5 | 5 | 5 | 0 | 0 | 0 | 0 |

TABLE 15-continued

| Test compound | Rate kg/ha | Herbicidal effect | | | | Phytotoxicity | | | |
|---|---|---|---|---|---|---|---|---|---|
| | | A | B | C | D | E | F | G | H |
| 58 | 2 | 5 | 5 | 5 | 4.5 | 0 | 0 | 0 | 0 |
| | 1 | 5 | 5 | 5 | 5 | 0 | 0 | 0 | 3 |
| 63 | 2 | 5 | 5 | 5 | 5 | 0 | 0 | 0 | 2 |
| | 1 | 5 | 5 | 5 | 5 | 0 | 0 | | 3.5 |
| 64 | 2 | 5 | 5 | 5 | 5 | | 0 | | 1.5 |
| | 1 | 5 | 5 | 5 | 5 | | 0 | | 1 |
| 65 | 2 | 5 | 5 | 5 | 5 | 0 | 0 | | |
| | 1 | 5 | 5 | 5 | 5 | 0 | 0 | | |
| 66 | 2 | 5 | 2 | 5 | 5 | 0 | 0 | | |
| | 1 | 5 | 2 | 5 | 5 | 0 | 0 | | |
| 67 | 2 | 5 | 5 | 5 | 5 | 0 | 0 | | |
| | 1 | 5 | 5 | 5 | 5 | 0 | 0 | | |
| 68 | 2 | 5 | 5 | 5 | 5 | 0 | 0 | | |
| | 1 | 5 | 5 | 5 | 5 | 0 | 0 | | |
| 78 | 2 | 5 | 5 | 5 | 5 | 0 | 1 | 0 | 0.5 |
| | 1 | 5 | 5 | 3 | 5 | 0 | 0 | 0 | 0 |
| 79 | 2 | 5 | 5 | 5 | 5 | 0 | 1.5 | 0.5 | 2 |
| | 1 | 5 | 5 | 5 | 5 | 0 | 0 | 0 | 1 |
| 81 | 2 | 5 | 5 | 5 | 5 | 0 | 0 | 0 | 0.5 |
| | 1 | 5 | 5 | 5 | 5 | 0 | 0 | 0 | 0.5 |
| 82 | 2 | 5 | 5 | 5 | 5 | 0 | 0 | 0 | 2 |
| | 1 | 5 | 5 | 5 | 5 | 0 | 0 | 0 | 1 |
| 83 | 2 | 4 | 5 | 5 | 5 | 0 | 0 | 0.5 | 2 |
| | 1 | 2 | 5 | 5 | 5 | 0 | 0 | 0 | 1 |
| 84 | 2 | 5 | 5 | 5 | 5 | 0 | 0.5 | 0 | 1 |
| | 1 | 5 | 5 | 5 | 5 | 0 | 0 | 0 | 0.5 |
| 85 | 2 | 3 | 5 | 5 | 5 | 0 | 0 | 0 | 0 |
| | 1 | 2 | 5 | 5 | 5 | 0 | 0 | 0 | 0 |
| 86 | 2 | 5 | 5 | 5 | 5 | 0 | 0 | 0 | 1 |
| | 1 | 5 | 5 | 5 | 5 | 0 | 0 | 0 | 1 |
| 90 | 2 | 5 | 5 | 5 | 5 | 0 | 0 | | |
| | 1 | 5 | 5 | 5 | 5 | 0 | 0 | | |
| 91 | 2 | 5 | 5 | 5 | 5 | 0 | 0 | | |
| | 1 | 5 | 5 | 5 | 5 | 0 | 0 | | |
| 93 | 2 | 5 | 5 | 5 | 5 | 0 | 0 | 0 | 2 |
| | 1 | 3 | 5 | 5 | 5 | 0 | 0 | 0 | 1 |
| 95 | 2 | 5 | 5 | 5 | 5 | 0 | 0 | | 1 |
| | 1 | 5 | 5 | 5 | 5 | 0 | 0 | | 0 |
| 96 | 2 | 5 | 5 | 5 | 5 | 0 | 0.5 | 1 | 2 |
| | 1 | 5 | 5 | 5 | 5 | 0 | 0 | 0 | 1 |
| 98 | 2 | 5 | 4 | 5 | 5 | | 0 | 0 | 0 |
| | 1 | 5 | 3 | 5 | 5 | | 0 | 0 | 0 |
| 100 | 2 | 5 | 5 | 5 | 5 | 0 | 0 | 0 | 1 |
| | 1 | 5 | 5 | 5 | 5 | 0 | 0 | 0 | 0 |
| 101 | 2 | 5 | 5 | 5 | 5 | 0 | 0 | 0 | 0.5 |
| | 1 | 5 | 5 | 5 | 2 | 0 | 0 | 0 | 0 |
| 103 | 2 | 5 | 5 | 5 | 5 | 0 | 0 | 0 | 0.5 |
| | 1 | 5 | 5 | 5 | 5 | 0 | 0 | 0 | 0 |
| 105 | 2 | 5 | 5 | 5 | 5 | 0 | 0 | | |
| | 1 | 5 | 5 | 5 | 5 | 0 | 0 | | |
| 106 | 2 | 5 | 5 | 5 | 5 | 0 | 0 | | |
| | 1 | 5 | 5 | 5 | 5 | 0 | 0 | | |
| 107 | 2 | 5 | 5 | 5 | 5 | 0 | 0 | | |
| | 1 | 5 | 5 | 5 | 5 | 0 | 0 | | |
| 108 | 2 | 5 | 5 | 5 | 5 | 0 | 0 | | |
| | 1 | 5 | 5 | 5 | 5 | 0 | 0 | | |
| 110 | 2 | 5 | 5 | 5 | 5 | | 0 | | |
| | 1 | 5 | 4 | 5 | 5 | | 0 | | |
| 111 | 2 | 5 | 5 | 5 | 5 | | 0 | | |
| | 1 | 5 | 5 | 5 | 5 | | 0 | | |
| 113 | 2 | 5 | 5 | 5 | 5 | 0.5 | 0 | 0 | 2 |
| | 1 | 5 | 5 | 5 | 5 | 0 | 0 | 0 | 1 |
| 115 | 2 | 5 | 5 | 5 | 5 | 0 | 0 | 0 | 2 |
| | 1 | 5 | 4.5 | 5 | 5 | 0 | 0 | 0 | 0.5 |
| 126 | 2 | 5 | 5 | 5 | 5 | | 0.5 | 1 | 0 |
| | 1 | 5 | 5 | 2.5 | 5 | | 0 | 0 | 0 |
| 127 | 2 | 5 | 5 | 5 | 5 | | 1 | 1.5 | 0 |
| | 1 | 2 | 5 | 5 | 5 | | 0 | 0 | 0 |
| 129 | 2 | 5 | 5 | 5 | 5 | | 0 | 0 | 0 |
| | 1 | 5 | 5 | 5 | 5 | | 0 | 0 | 0 |
| 130 | 2 | 5 | 5 | 5 | 5 | | 0 | 0 | 0 |
| | 1 | 5 | 5 | 5 | 5 | | 0 | 0 | 0 |
| 131 | 2 | 5 | 5 | 5 | 5 | 0 | 0 | 0 | 2 |
| | 1 | 5 | 4.5 | 5 | 5 | 0 | 0 | 0 | 1 |
| 132 | 2 | 5 | 5 | 5 | 5 | 0 | 2 | 1 | 1 |
| | 1 | 5 | 5 | 5 | 5 | 0 | 1 | 0 | 0.5 |
| 133 | 2 | 5 | 5 | 5 | 5 | 0 | 0 | 0 | 0 |
| | 1 | 5 | 5 | 5 | 5 | 0 | 0 | 0 | 0 |
| 134 | 2 | 5 | 5 | 5 | 5 | 0 | 0 | 1 | 1 |
| | 1 | 5 | 5 | 5 | 5 | 0 | 0 | 0 | 0 |
| 136 | 2 | 5 | 5 | 5 | 5 | 0 | 0 | 0 | 0 |
| | 1 | 5 | 5 | 5 | 5 | 0 | 0 | 0 | 0 |
| 137 | 2 | 5 | 5 | 5 | 5 | | 0 | 0 | 0 |
| | 1 | 5 | 4 | 5 | 5 | | 0 | 0 | 0 |
| 140 | 2 | 5 | 5 | 5 | 5 | | 0.5 | 0 | 0 |
| | 1 | 5 | 5 | 5 | 5 | | 0 | 0 | 0 |
| 141 | 2 | 5 | 4.5 | 5 | 5 | | 0 | 0 | 0 |
| | 1 | 5 | 2 | 5 | 5 | | 0 | 0 | 0 |
| 142 | 2 | 5 | 5 | 5 | 5 | 0 | | | 5 |
| | 1 | 5 | 5 | 5 | 5 | 0 | | | 1 |
| 143 | 2 | 5 | 5 | 5 | 5 | 0 | | | 4.5 |
| | 1 | 5 | 5 | 5 | 5 | 0 | | | 0.5 |
| 144 | 2 | 5 | 5 | 1 | 5 | | 0 | | 0.5 |
| | 1 | 5 | 5 | 0.5 | 5 | | 0 | | 0.5 |
| 145 | 2 | 5 | 5 | 5 | 5 | | 0 | | 4.5 |
| | 1 | 5 | 4 | 5 | 5 | | 0 | | 3 |
| 151 | 2 | 5 | 5 | 5 | 5 | 0 | 0 | 0 | 1 |
| | 1 | 5 | 5 | 5 | 5 | 0 | 0 | 0 | 0 |
| 159 | 2 | 5 | 5 | 5 | 5 | 0 | 0 | 0 | 0 |
| | 1 | 5 | 5 | 3 | 5 | 0 | 0 | 0 | 0 |
| 160 | 2 | 5 | 5 | 5 | 5 | 0 | 0 | 0 | 0 |
| | 1 | 3 | 5 | 5 | 5 | 0 | 0 | | 0 |
| 161 | 2 | 5 | 5 | 5 | 5 | 1 | 1 | 1 | 2 |
| | 1 | 3.5 | 5 | 5 | 5 | 0 | 0 | 0 | 1 |
| 162 | 2 | 5 | 5 | 5 | 5 | 0 | | 1 | 1 |
| | 1 | 3 | 5 | 5 | 5 | 0 | | 0 | 0 |
| 164 | 2 | 5 | 5 | 5 | 5 | 0 | 0 | 0.5 | 2 |
| | 1 | 5 | 5 | 5 | 5 | 0 | 0 | 0 | 1 |
| 165 | 2 | 5 | 5 | 5 | 5 | 0 | | | 1 |
| | 1 | 5 | 5 | 5 | 5 | 0 | | | 0.5 |
| 169 | 2 | 5 | 5 | 5 | | 1 | 0.5 | 2 | 2 |
| | 1 | 5 | 5 | 5 | | 0 | 0 | 1 | 1 |
| 170 | 2 | 5 | 5 | 5 | 5 | 0 | 2 | 2 | 2 |
| | 1 | 5 | 5 | 5 | 5 | 0 | 1 | 1 | 1 |
| 172 | 2 | 5 | 5 | 5 | 5 | 0 | 1 | 0 | 2 |
| | 1 | 5 | 5 | 5 | 5 | 0 | 0 | 0 | 1 |
| 173 | 2 | 5 | 5 | 5 | 5 | 0 | 1 | 0 | 1 |
| | 1 | 5 | 5 | 5 | 5 | 0 | 0 | 0 | 0 |
| 174 | 2 | 5 | 5 | 5 | 5 | 0 | 0 | 0 | 0 |
| | 1 | 3 | 5 | 4.5 | 5 | 0 | 0 | 0 | 0 |
| 179 | 2 | 5 | 5 | 5 | 5 | 0 | 0 | 0 | 0 |
| | 1 | 5 | 5 | 5 | 5 | 0 | 0 | 0 | 0 |
| 180 | 2 | 5 | 5 | 5 | | 0 | 0 | | 5 |
| | 1 | 5 | 5 | 5 | | 0 | 0 | | 3 |
| 181 | 2 | 5 | 5 | 5 | | 0 | 0.5 | | 2 |
| | 1 | 5 | 5 | 5 | | 0 | 0 | | 1 |
| 182 | 2 | 5 | 5 | 5 | 5 | 0 | 0 | 0 | 0 |
| | 1 | 3 | 4 | 5 | 5 | 0 | 0 | 0 | 0 |
| 184 | 2 | 4 | 5 | 5 | 5 | 0 | 0 | 0 | 1 |
| | 1 | 3 | 5 | 5 | 5 | 0 | 0 | 0 | 0 |
| 186 | 2 | 5 | 5 | 5 | 5 | | | 1.5 | 0 |
| | 1 | 5 | 5 | 5 | 5 | | | 0 | 0 |
| 192 | 2 | 5 | 5 | 5 | 5 | | 0 | 0 | 0 |
| | 1 | 4.5 | 5 | 5 | 5 | | 0 | 0 | 0 |
| 193 | 2 | 5 | 5 | 5 | 5 | 0 | 0 | 0 | 1 |
| | 1 | 5 | 5 | 5 | 3 | 0 | 0 | 0 | 0 |
| 194 | 2 | 5 | 5 | 5 | 5 | 0 | 0 | 0 | 1 |
| | 1 | 5 | 5 | 5 | 5 | 0 | 0 | 0 | 0.5 |
| 205 | 2 | 5 | 5 | 5 | 5 | 0 | 0 | 0 | 0 |
| | 1 | 5 | 4.5 | 5 | 5 | 0 | 0 | 0 | 0 |
| 206 | 2 | 5 | 5 | 5 | 5 | | 0 | 0 | 0 |
| | 1 | 5 | 5 | 5 | 5 | | 0 | 0 | 0 |
| 207 | 2 | 5 | 5 | 5 | 5 | | 0 | 0 | 0 |
| | 1 | 5 | 4 | 5 | 5 | | 0 | 0 | 0 |
| 209 | 2 | 5 | 5 | 5 | 5 | 0 | 0 | 0 | 0 |
| | 1 | 4.5 | 4 | 5 | 5 | 0 | 0 | 0 | 0 |
| 210 | 2 | 5 | 5 | 5 | 5 | 1 | 0 | 0 | 1.5 |
| | 1 | 5 | 5 | 5 | 5 | 0 | 0 | 0 | 0 |
| 211 | 2 | 5 | 5 | 5 | 5 | 0 | 0 | | 4.5 |
| | 1 | 5 | 5 | 5 | 5 | 0 | 0 | | 3.5 |
| 212 | 2 | 5 | 5 | 5 | 5 | 0 | 0 | | 0 |
| | 1 | 5 | 3.5 | 2 | 5 | 0 | 0 | | 0 |
| 220 | 2 | 5 | 5 | 5 | 5 | 0 | 0 | | 2.5 |
| | 1 | 5 | 4.5 | 2 | 5 | 0 | 0 | | 2 |
| 225 | 2 | 5 | 5 | 5 | 5 | 0 | 0 | | 1.5 |
| | 1 | 5 | 3 | 5 | 5 | 0 | 0 | | 0 |
| 230 | 2 | 5 | 5 | 5 | 5 | | 0 | | 0.5 |

TABLE 15-continued

| Test compound | Rate kg/ha | Herbicidal effect A | B | C | D | Phytotoxicity E | F | G | H |
|---|---|---|---|---|---|---|---|---|---|
| | 1 | 2 | 4.5 | 5 | 5 | | 0 | | 0 |
| 232 | 2 | 5 | 5 | 5 | 5 | 0 | 0 | | 2 |
| | 1 | 5 | 5 | 5 | 5 | 0 | 0 | | 0.5 |
| 233 | 2 | 5 | 5 | 5 | 5 | 0 | 0 | | 1 |
| | 1 | 5 | 5 | 5 | 5 | 0 | 0 | | 0 |
| 234 | 2 | 5 | 5 | 5 | 5 | 0 | 0 | | 2 |
| | 1 | 5 | 4.5 | 5 | 5 | 0 | 0 | | 1.5 |
| 235 | 2 | 5 | 3 | 5 | 5 | 0 | 0 | | 2 |
| | 1 | 5 | 3 | 5 | 5 | 0 | 0 | | 2 |
| 239 | 2 | 5 | 5 | 5 | 5 | 0 | 0 | 0 | 1.5 |
| | 1 | 5 | 5 | 5 | 5 | 0 | 0 | 0 | 0 |
| 240 | 2 | 5 | 5 | 5 | 5 | 0 | 0 | 0.5 | 3 |
| | 1 | 5 | 5 | 5 | 5 | 0 | 0 | 0 | 2 |
| 244 | 2 | 5 | 5 | 5 | 5 | 0 | 0 | 0 | 0 |
| | 1 | 5 | 5 | 5 | 5 | 0 | 0 | 0 | 0 |
| 245 | 2 | 4.5 | 5 | 5 | 5 | 0 | 0 | 0 | 0.5 |
| | 1 | 3 | 4 | 5 | 5 | 0 | 0 | 0 | 0 |
| 246 | 2 | 5 | 5 | 5 | 5 | 0 | 0 | 0 | 1 |
| | 1 | 5 | 5 | 5 | 5 | 0 | 0 | 0 | 1 |
| 247 | 2 | 5 | 5 | 5 | 5 | 0 | 0 | 0 | 0 |
| | 1 | 5 | 5 | 5 | 5 | 0 | 0 | 0 | 0 |
| 248 | 2 | 5 | 5 | 5 | 5 | 0 | 0 | 0 | 0 |
| | 1 | 5 | 5 | 5 | 5 | 0 | 0 | 0 | 0 |
| 251 | 2 | 5 | 5 | 5 | 5 | 0 | 0 | | 4 |
| | 1 | 5 | 5 | 5 | 5 | 0 | 0 | | 2 |
| 252 | 2 | 5 | 5 | 5 | 5 | 0 | 0 | | |
| | 1 | 5 | 5 | 5 | 5 | 0 | 0 | | |
| 257 | 2 | 5 | 5 | 5 | 5 | | 0 | 0 | 0 |
| | 1 | 1.5 | 5 | 5 | 5 | | 0 | 0 | 0 |
| 258 | 2 | 5 | 5 | 5 | 5 | 0 | 2 | 0 | 0 |
| | 1 | 5 | 5 | 5 | 5 | 0 | 1 | 0 | 0 |
| 260 | 2 | 5 | 4.5 | 5 | 5 | 0 | 0 | 0 | 4.5 |
| | 1 | 5 | 1.5 | 5 | 5 | 0 | 0 | 0 | 1 |
| 261 | 2 | 5 | 5 | 5 | 5 | 0 | 0 | | 3 |
| | 1 | 5 | 5 | 5 | 5 | 0 | 0 | | 1 |
| 262 | 2 | 5 | 5 | 5 | 5 | 0 | 0 | | 5 |
| | 1 | 5 | 5 | 5 | 5 | 0 | 0 | | 3 |
| 265 | 2 | 5 | 5 | 5 | 5 | 0 | 1 | 0 | 2 |
| | 1 | 5 | 2.5 | 5 | 5 | 0 | 0 | 0 | 1 |
| 268 | 2 | 5 | 5 | 5 | 5 | 0 | 0 | 0 | 2 |
| | 1 | 5 | 4 | 5 | 5 | 0 | 0 | 0 | 2 |
| 272 | 2 | 5 | 5 | 5 | 5 | 0 | 0.5 | 0 | 4.5 |
| | 1 | 5 | 5 | 5 | 5 | 0 | 0 | 0 | 2.5 |
| 273 | 2 | 5 | 5 | 5 | 5 | 0 | 0.5 | 0 | 4.5 |
| | 1 | 5 | 5 | 5 | 5 | 0 | 0 | 0 | 4.5 |
| 276 | 2 | 5 | 5 | 5 | 5 | 0 | 0 | | 2 |
| | 1 | 5 | 4 | 5 | 5 | 0 | 0 | | 1.5 |
| 279 | 2 | 5 | 5 | 5 | 5 | 0 | 0 | 1 | 2 |
| | 1 | 5 | 5 | 5 | 5 | 0 | 0 | 0 | 1 |
| 280 | 2 | 5 | 5 | 5 | 5 | 0 | 0.5 | 0 | 4 |
| | 1 | 5 | 5 | 5 | 5 | 0 | 0 | 0 | 2.5 |
| 281 | 2 | 5 | 5 | 5 | 5 | 0 | 0 | 0 | 2 |
| | 1 | 5 | 4.5 | 5 | 5 | 0 | 0 | 0 | 1 |
| 283 | 2 | 5 | 5 | 5 | 5 | 0 | 0 | 0 | 2 |
| | 1 | 5 | 5 | 5 | 5 | 0 | 0 | 0 | 1 |
| 285 | 2 | 5 | 5 | 5 | 5 | 0 | 0 | | 1.5 |
| | 1 | 5 | 5 | 5 | 5 | 0 | 0 | | 1 |
| 288 | 2 | 5 | 5 | 5 | 5 | 0 | 0 | | 0.5 |
| | 1 | 5 | 5 | 5 | 5 | 0 | 0 | | 0 |
| 296 | 2 | 5 | 2 | 5 | 5 | 0 | 0 | 0 | 0 |
| | 1 | 5 | 2 | 5 | 4.5 | 0 | 0 | 0 | 0 |
| 297 | 2 | 5 | 5 | 5 | 5 | 0 | 0 | 0 | 1.5 |
| | 1 | 5 | 5 | 2 | 5 | 0 | 0 | 0 | 1 |
| 309 | 2 | 5 | 4.5 | 5 | 5 | 0 | 0 | 0 | 2 |
| | 1 | 4.5 | 4 | 5 | 5 | 0 | 0 | 0 | 2 |
| 310 | 2 | 5 | 5 | 5 | 5 | 0 | 0 | 0 | 1.5 |
| | 1 | 5 | 4.5 | 5 | 4.5 | 0 | 0 | 0 | 1 |
| 312 | 2 | 5 | 5 | 5 | 5 | 0 | 0 | | 4.5 |
| | 1 | 5 | 5 | 5 | 5 | 0 | 0 | | 1 |
| 313 | 2 | 5 | 5 | 5 | 5 | 0 | 0 | | 3 |
| | 1 | 5 | 5 | 5 | 5 | 0 | 0 | | 0.5 |
| 315 | 2 | 5 | 5 | 5 | 5 | 0 | 0 | 0 | 4 |
| | 1 | 5 | 5 | 5 | 5 | 0 | 0 | 0 | 2.5 |
| 316 | 2 | 5 | 5 | 5 | 5 | 0 | 0 | 0 | 3 |
| | 1 | 5 | 5 | 5 | 5 | 0 | 0 | 0 | 1 |
| 319 | 2 | 5 | 5 | 5 | 5 | 0 | 0 | 0 | 2 |
| | 1 | 5 | 5 | 5 | 5 | 0 | 0 | 0 | 1 |
| 320 | 2 | 4 | 5 | 5 | 5 | 0 | 2 | | 1.5 |
| | 1 | 2 | 5 | 5 | 5 | 0 | 0 | 0 | 1 |
| 321 | 2 | 5 | 5 | 5 | 5 | 0 | 0 | 0 | |
| | 1 | 3 | 5 | 5 | 5 | 0 | 0 | 0 | 1 |
| 323 | 2 | 5 | 5 | 5 | 5 | 0 | 0 | 0 | 0.5 |
| | 1 | 5 | 5 | 5 | 5 | 0 | 0 | 0 | 0 |
| 324 | 2 | 5 | 5 | 5 | 5 | 0 | 0 | 0 | 0 |
| | 1 | 5 | 5 | 5 | 5 | 0 | 0 | 0 | 0 |
| 326 | 2 | 5 | 5 | 5 | | | 0 | | 1.5 |
| | 1 | 3 | 4.5 | 5 | | | 0 | | 0.5 |
| 327 | 2 | 5 | 5 | 5 | 5 | 0 | 0 | 0 | 0 |
| | 1 | 5 | 5 | 5 | 5 | 0 | 0 | 0 | 0 |
| 328 | 2 | 5 | 5 | 5 | 5 | 0 | 5 | 1.5 | 5 |
| | 1 | 5 | 5 | 5 | 5 | 0 | 1 | 0 | 0 |
| 330 | 2 | 5 | 5 | 5 | 5 | 0 | 0 | 0 | 2.5 |
| | 1 | 5 | 4 | 5 | 5 | 0 | 0 | 0 | 1 |
| 339 | 2 | 5 | 5 | 5 | 5 | 0 | 0 | 0 | 3 |
| | 1 | 5 | 3 | 5 | 5 | 0 | 0 | 0 | 2 |
| 340 | 2 | 5 | 4.5 | 5 | 5 | 0 | 0 | 0 | 1 |
| | 1 | 5 | 3 | 5 | 5 | 0 | 0 | 0 | 0.5 |
| 343 | 2 | 5 | 2.5 | 5 | 5 | 0 | 0 | 0 | 3 |
| | 1 | 5 | 1 | 5 | 5 | 0 | 0 | 0 | 0.5 |
| 344 | 2 | 5 | 5 | 5 | 5 | 0 | 0 | | 4 |
| | 1 | 5 | 5 | 4.5 | 5 | 0 | 0 | | 3 |
| 345 | 2 | 5 | 3.5 | 5 | 5 | 0 | 0 | | 4.5 |
| | 1 | 4.5 | 3 | 5 | 5 | 0 | 0 | | 3.5 |
| 348 | 2 | 5 | 5 | 5 | 5 | 0 | 0 | 0 | 3 |
| | 1 | 5 | 5 | 5 | 5 | 0 | 0 | 0 | 2 |
| 349 | 2 | 5 | 5 | 5 | 5 | 0 | 0 | 1 | 2 |
| | 1 | 5 | 3 | 5 | 5 | 0 | 0 | 0 | 0 |
| 360 | 2 | 5 | 5 | 5 | 5 | 0 | 0 | 0 | 1.5 |
| | 1 | 5 | 4.5 | 5 | 5 | 0 | 0 | 0 | 0.5 |
| 362 | 2 | 5 | 5 | 5 | 5 | 0 | 0 | 1 | 2 |
| | 1 | 4.5 | 4.5 | 4.5 | 2 | 0 | 0 | 0.5 | 0 |
| 363 | 2 | 5 | 4.5 | 5 | 5 | 0 | 0 | 0 | 1 |
| | 1 | | 3 | 5 | 4.5 | 0 | 0 | 0 | 0.5 |
| 365 | 2 | 5 | 5 | 5 | 5 | 0 | 0 | 1 | 2 |
| | 1 | 5 | 5 | 5 | 5 | 0 | 0 | 0 | 2 |
| 371 | 2 | 5 | 5 | 5 | 5 | 0 | 0 | 0 | 2.5 |
| | 1 | 5 | 4.5 | 5 | 5 | 0 | 0 | 0 | 1.5 |
| Comparative Compound (1) | 2 | 2 | 3 | 4 | 4 | 2 | 3 | 1 | 2 |
| | 1 | 1 | 1 | 3 | 2 | 1 | 2 | 1 | 2 |
| Comparative Compound (2) | 2 | 0 | 1 | 1 | 2 | 0 | 0 | 0 | 1 |
| | 1 | 0 | 0 | 0 | 1 | 0 | 0 | 0 | 0 |
| Comparative Compound (3) | 2 | 4 | 5 | 5 | 4 | 3 | 4 | 3 | 2 |
| | 1 | 2 | 5 | 2 | 3 | 2 | 3 | 2 | 2 |

Comparative Compound (1): [phenyl-O-phenyl-NHC(=O)N(Me)(OMe)]
(the compound described in Jap. Laid-Open Pat. Publn. No. 111542/77)

Comparative Compound (2): [phenyl-O-(pyridyl)-NHC(=O)N(Me)(OMe)]
(the compound described in Jap. Laid-Open Pat. Publn. No. 36456/81)

Comparative Compound (3): Cl-phenyl-O-phenyl-NHC(=O)N(Me)(Me)
(chloroxuron)

In Table 15 above and Table 16 given below, the names of the plants are indicated by letters A to J as follows:
A: cocklebur (*Xanthium canadense*)
B: blackjack (*Bidens pilosa*)
C: velvet leaf (*Abutilon theophrasti*)
D: jimsonweed (*Datura stramonium*)
E: wheat (*Triticum aestivum*)
F: corn (*Zea mays*)
G: rice (*Oryza sativa*)
H: soybean (*Glycine max*)

I: barnyard grass (*Echinochloa crus-galli*)
J: Pigweed (*Amaranthus retroflexus*).

TEST EXAMPLE 2

Herbicidal test by soil treatment

Porcelain pots (9 cm in diameter) were filled with sieved upland farm soil, and seeds of the plants indicated in Table 16 were sown and covered with the soil (1 cm). Immediately then, a predetermined amount of a wettable powder of each of the test compounds, prepared as in Formulation Example 1, was diluted with 1.5 ml of water, and the dispersion was uniformly sprayed onto the surface of the soil by a small atomizer. The plants were grown in a green house for 20 days after the soil treatment, and the herbicidal effect of each of the test compounds was examined and evaluated in accordance with the standards shown in Table 14. The results are shown in Table 16.

TABLE 16

| Test compound | Rate kg/ha | Herbicidal effect | | | |
|---|---|---|---|---|---|
| | | I | J | B | C |
| 7 | 5 | 5 | 5 | 5 | 5 |
| | 2.5 | 4.5 | 3.5 | 5 | 5 |
| 84 | 5 | 5 | 5 | 5 | 5 |
| | 2.5 | 3 | 5 | 4.5 | 5 |
| 85 | 5 | 2 | 5 | 5 | 5 |
| | 2.5 | 1 | 5 | 4.5 | 5 |
| 95 | 5 | 4.5 | 5 | 4.5 | 5 |
| | 2.5 | 1 | 5 | 3 | 5 |
| 96 | 5 | 5 | 5 | 5 | 5 |
| | 2.5 | 4.5 | 5 | 5 | 5 |
| 103 | 5 | 1 | 5 | 5 | 5 |
| | 2.5 | 0 | 5 | 4 | 5 |
| 105 | 5 | 0 | 5 | 5 | 5 |
| | 2.5 | 0 | 5 | 2 | 5 |
| 113 | 5 | 4 | 5 | 5 | 5 |
| | 2.5 | 1.5 | 4.5 | 3 | 4.5 |
| 132 | 5 | 5 | 5 | 5 | 5 |
| | 2.5 | 5 | 5 | 4.5 | 5 |
| 151 | 5 | 1 | 5 | 5 | 5 |
| | 2.5 | 0 | 5 | 5 | 4.5 |
| 169 | 5 | 5 | 5 | 5 | 5 |
| | 2.5 | 5 | 3 | 5 | 4 |
| 190 | 5 | 4 | 5 | 5 | 5 |
| | 2.5 | 2 | 5 | 5 | 5 |
| 191 | 5 | 4.5 | 5 | 5 | 5 |
| | 2.5 | 3 | 5 | 5 | 5 |
| 194 | 5 | 2 | 5 | 5 | 5 |
| | 2.5 | 0 | 5 | 5 | 5 |
| 310 | 5 | 0 | 5 | 5 | 5 |
| | 2.5 | 0 | 5 | 4.5 | 4.5 |
| 319 | 5 | 3.5 | 5 | 5 | 5 |
| | 2.5 | 0 | 5 | 5 | 4.5 |
| 365 | 5 | 1 | 5 | 5 | 5 |
| | 2.5 | 0 | 2 | 5 | 5 |

INDUSTRIAL UTILIZABILITY

The compounds of formula [I] of this invention are useful for controlling undesired vegetation in low dosages without substantial phytotoxicity on useful crops.

We claim:

1. A urea derivative represented by the following formula [I]

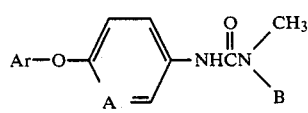

wherein
A represents the bond $$-C= \atop X$$

in which X is a hydrogen atom, a chlorine atom, a nitro group or a trifluoromethyl group;

B represents a hydrogen atom, a methyl group or a methoxy group; and

Ar represents one member selected from the group consisting of

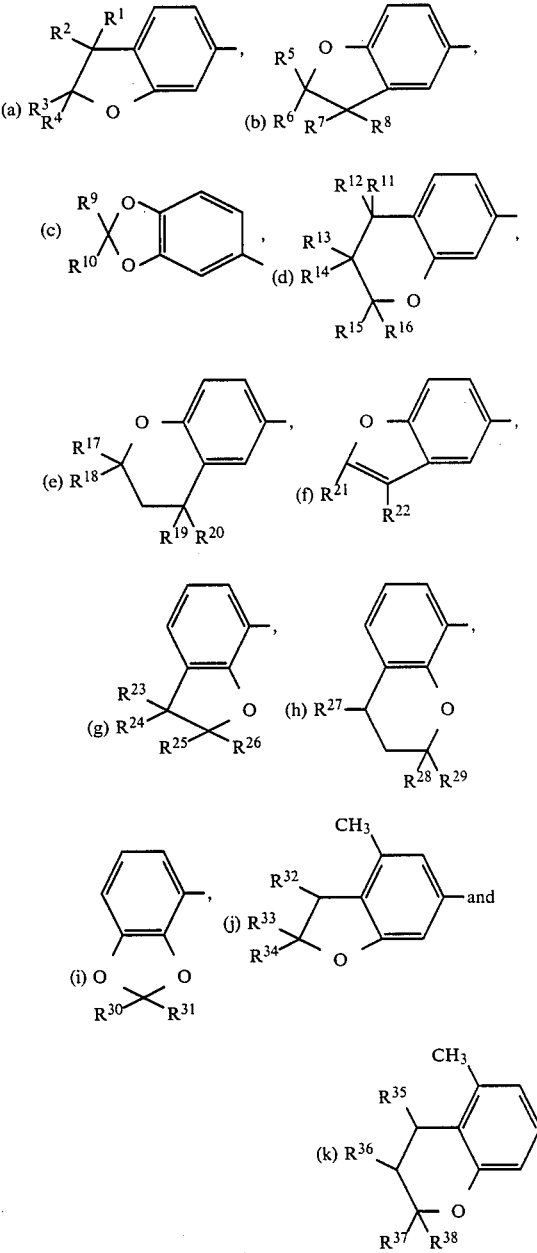

in which $R^1$ to $R^{38}$, independently from each other, represent a hydrogen atom, a lower alkyl group or a lower alkoxy group; $R^{16}$ may further represent a hydroxyl group; a pair of $R^2$ and $R^3$, and a pair of $R^6$ and $R^7$ each, taken together, may represent an alkylene linkage and may form a 5- or 6-membered ring together with the two adjacent carbon atoms to which they are bonded; a pair of $R^9$ and $R^{10}$, taken together, may represent an alkylene linkage and may form a 5- or 6-membered ring together with the carbon atom to which they are bonded; $R^{11}$ and $R^{12}$, taken together, may form an ethylenedioxy linkage $-O-(CH_2)_2-O-$, or $R^{11}$ and $R^{15}$, taken together, may form an alkylene linkage and form a 5- or 6-membered ring together with the carbon atoms to which they are bonded, or $R^{15}$ and $R^{16}$, taken together, may represent an alkylene linkage and form a 5- or 6-membered ring together with one carbon atom to which they are bonded, or $R^{14}$ and $R^{15}$, taken together, may form a dichloromethylene linkage.

2. The urea derivative of claim 1 wherein X is a hydrogen atom.

3. The urea derivative of claim 1 wherein X is a chlorine atom.

4. The urea derivative of claim 1 wherein X is a nitro group.

5. The urea derivative of claim 1 wherein X is a trifluoromethyl group.

6. The urea derivative represented by the formula [I] as set forth in claim 1 wherein Ar represents one member selected from the group (a).

7. The urea derivative represented by the formula [I] as set forth in claim 1 wherein Ar represents one member selected from the group (b).

8. The urea derivative represented by the formula [I] as set forth in claim 1 wherein Ar represents one member selected from the group (c).

9. The urea derivative represented by the formula [I] as set forth in claim 1 wherein Ar represents one member selected from the group (d).

10. The urea derivative represented by the formula [I] as set forth in claim 1 wherein Ar represents one member selected from the group (e).

11. The urea derivative represented by the formula [I] as set forth in claim 1 wherein Ar represents one member selected from the group (f).

12. The urea derivative represented by the formula [I] as set forth in claim 1 wherein Ar represents one member selected from the group (g).

13. The urea derivative represented by the formula [I] as set forth in claim 1 wherein Ar represents one member selected from the group (h).

14. The urea derivative represented by the formula [I] as set forth in claim 1 wherein Ar represents one member selected from the group (i).

15. The urea derivative represented by the formula [I] as set forth in claim 1 wherein Ar represents one member selected from the group (j).

16. The urea derivative represented by the formula [I] as set forth in claim 1 wherein Ar represents one member selected from the group (k).

17. A herbicidal composition comprising a herbicidally effective amount of at least one compound of formula [I] according to claim 1 and an agriculturally acceptable diluent or carrier.

18. The herbicidal composition of claim 17 wherein the amount of the compound of formula [I] is about 0.5 to about 70% by weight based on the weight of the composition.

19. The herbicidal composition of claim 17 which is in the form of granules or a dust and in which the amount of the compound of formula [I] is 0.5 to 20% by weight based on the weight of the composition.

20. The herbicidal composition of claim 17 which is in the form of an emulsifiable concentrate or wettable powder and in which the amount of the compound of formula [I] is 5 to 70% by weight based on the weight of the composition.

21. A method for controlling the growth of weeds, which comprises applying a herbicidally effective amount of at least one compound of formula [I] according to claim 1 to the weeds or the locus of such weeds.

22. The method for controlling the growth of weeds according to claim 21 which comprises applying from about 50 g to about 3 kg/hectare of at least one compound of formula [I] to the weeds or the locus of such weeds.

23. The method of claim 22 for controlling the growth of weeds in gramineous crops.

24. The method of claim 22 for controlling the growth of weeds in leguminous crops.

* * * * *

UNITED STATES PATENT AND TRADEMARK OFFICE
CERTIFICATE OF CORRECTION

PATENT NO. : 4,838,924
DATED : June 13, 1989
INVENTOR(S) : TETSUO TAKEMATSU ET AL.

It is certified that error appears in the above-identified patent and that said Letters Patent is hereby corrected as shown below:

In TABLE 4, in each of columns 33-34, 35-36, 37-38, 39-40, 41-42, 43-44, 45-46, 47-48, 49-50, 51-52, 53-54, 55-56, 57-58, 59-60, 61-62, 63-64 and 65-66, delete the column heading of the Table which reads "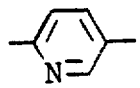"

and insert therefor

--  --.

In TABLE 12, columns 79-80, in the row for Precursor No. 2, in the column labelled "Synthesis method" correct the last structural formula to read:

-- 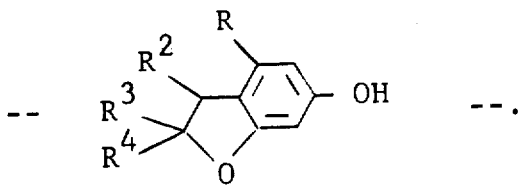 --.

UNITED STATES PATENT AND TRADEMARK OFFICE
CERTIFICATE OF CORRECTION

PATENT NO. : 4,838,924

DATED : June 13, 1989

INVENTOR(S) : TETSUO TEKAMATSU ET AL.

It is certified that error appears in the above-identified patent and that said Letters Patent is hereby corrected as shown below:

In TABLE 12, columns 81-82, in the row for Precursor No. 5, in the column labelled "Ar-OH", change the structural formula to read:

-- 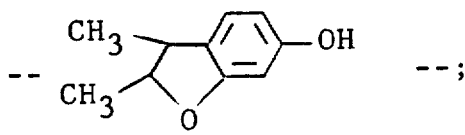 --;

still in the row for Precursor No. 5, in the column labelled "Synthesis method", delete " 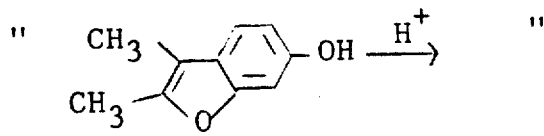 "

and insert therefor

-- 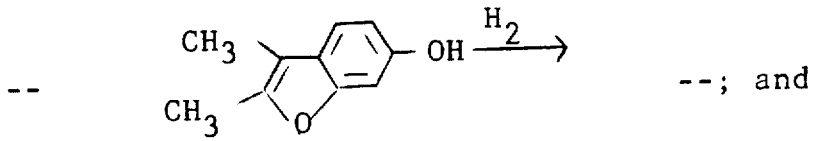 --; and

UNITED STATES PATENT AND TRADEMARK OFFICE
CERTIFICATE OF CORRECTION

PATENT NO. : 4,838,924
DATED : June 13, 1989
INVENTOR(S) : TETSUO TAKEMATSU ET AL.

It is certified that error appears in the above-identified patent and that said Letters Patent is hereby corrected as shown below:

in the row for Precursor No. 7, in the column labelled "Synthesis method", delete " 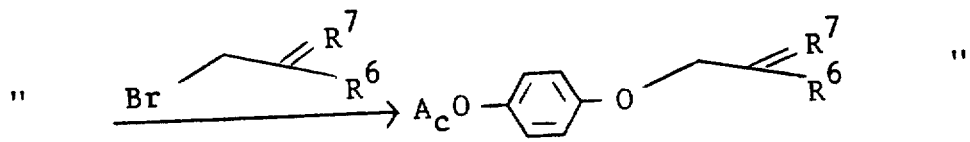 "

and insert therefor

-- 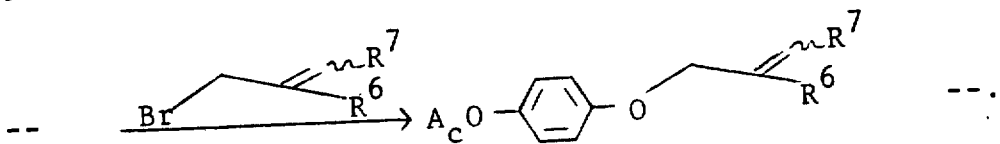 --.

In TABLE 12, columns 95-96, in the row for Precursor No. 24, in the column labelled "Synthesis method", change the last structural formula to read:

-- 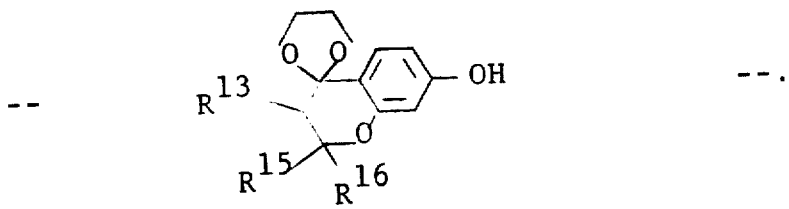 --.

UNITED STATES PATENT AND TRADEMARK OFFICE
CERTIFICATE OF CORRECTION

PATENT NO. : 4,838,924
DATED : June 13, 1989
INVENTOR(S) : TETSUO TAKEMATSU ET AL.

It is certified that error appears in the above-identified patent and that said Letters Patent is hereby corrected as shown below:

In TABLE 12, columns 97-98, in the row for Precursor No. 27, in the column labelled "Synthesis method" delete " 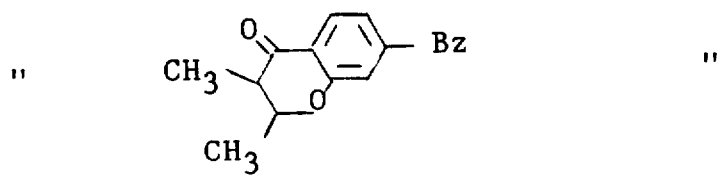 "

and insert therefor

-- 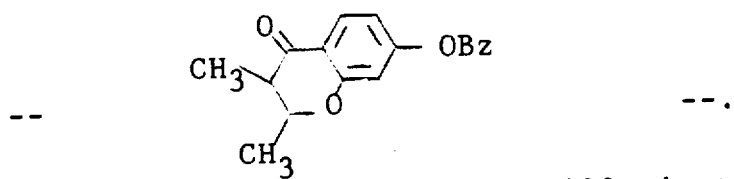 --.

In TABLE 12, columns 101-102, in the row for Precursor No. 32, in the column labelled "Synthesis method", delete "U.S. Pat. No. 4,003,919" and insert therefor -- 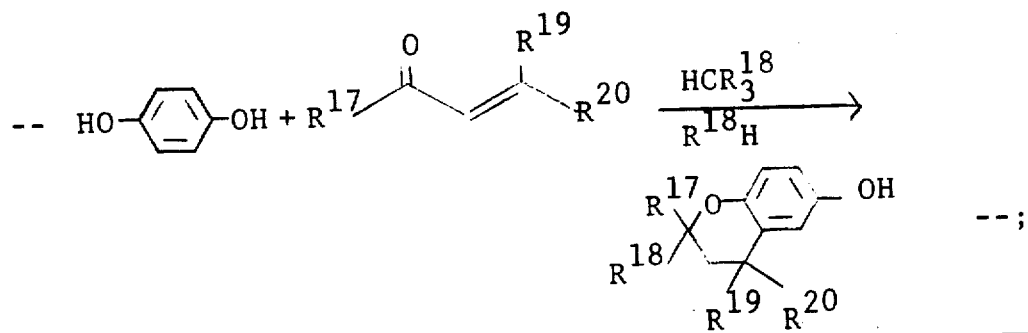 --;

UNITED STATES PATENT AND TRADEMARK OFFICE
CERTIFICATE OF CORRECTION

PATENT NO. : 4,838,924
DATED : June 13, 1989
INVENTOR(S) : TETSUO TAKEMATSU ET AL.

It is certified that error appears in the above-identified patent and that said Letters Patent is hereby corrected as shown below:

still in the row for Precursor No. 32, in the column labelled "Reference", insert --U.S. Patent No. 4,003,919--;

in the row between the rows for Precursor No. 32 and Precursor No. 33, delete the reaction equation in its entirety.

In TABLE 12, columns 103-104, in the row for Precursor No. 36, delete

" 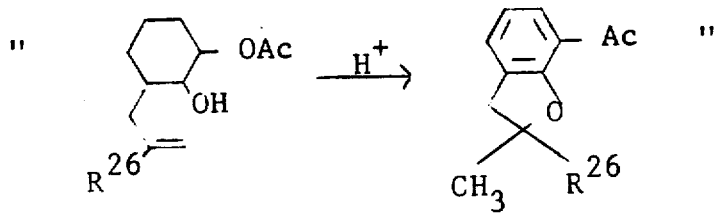 "

and insert therefor

-- 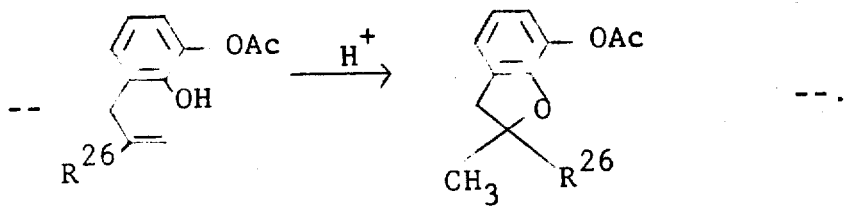 --.

UNITED STATES PATENT AND TRADEMARK OFFICE
CERTIFICATE OF CORRECTION

PATENT NO. : 4,838,924

DATED : June 13, 1989

INVENTOR(S) : TETSUO TAKEMATSU ET AL.

It is certified that error appears in the above-identified patent and that said Letters Patent is hereby corrected as shown below:

Column 113, line 49, delete "n-hexanetoluene" and insert therefor --n-hexane-toluene--.

Signed and Sealed this

Thirtieth Day of April, 1991

Attest:

HARRY F. MANBECK, JR.

Attesting Officer

Commissioner of Patents and Trademarks